United States Patent
Lenferink et al.

(10) Patent No.: US 10,487,153 B2
(45) Date of Patent: Nov. 26, 2019

(54) CARBONIC ANHYDRASE IX-SPECIFIC ANTIBODIES AND USES THEREOF

(71) Applicant: National Research Council of Canada, Ottawa (CA)

(72) Inventors: Anne E. G. Lenferink, Lorraine (CA); Maureen D. O'Connor, Beaconsfield (CA); Anne Marcil, Pierrefonds (CA); Yves Durocher, Montreal (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 15/580,713

(22) PCT Filed: Jun. 10, 2016

(86) PCT No.: PCT/IB2016/053448
§ 371 (c)(1),
(2) Date: Dec. 8, 2017

(87) PCT Pub. No.: WO2016/199097
PCT Pub. Date: Dec. 15, 2016

(65) Prior Publication Data
US 2018/0186893 A1 Jul. 5, 2018

Related U.S. Application Data

(60) Provisional application No. 62/173,405, filed on Jun. 10, 2015.

(51) Int. Cl.
| | |
|---|---|
| *C07K 16/40* | (2006.01) |
| *A61K 47/68* | (2017.01) |
| *G01N 33/53* | (2006.01) |
| *G01N 33/563* | (2006.01) |
| *G01N 33/574* | (2006.01) |
| *G01N 33/573* | (2006.01) |
| *A61K 51/10* | (2006.01) |
| *A61K 39/00* | (2006.01) |

(52) U.S. Cl.
CPC .......... *C07K 16/40* (2013.01); *A61K 47/6803* (2017.08); *A61K 47/6871* (2017.08); *A61K 51/1075* (2013.01); *G01N 33/573* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/567* (2013.01); *C07K 2317/76* (2013.01); *C07K 2317/92* (2013.01); *G01N 2333/988* (2013.01)

(58) Field of Classification Search
CPC ............................................................
C07K 16/40; C07K 2317/24; C07K 2317/56; C07K 2317/33; C07K 2317/34; C07K 2317/565; C07K 2317/567; C07K 2317/54; C07K 2317/55; C07K 317/567; C07K 2317/76; C07K 2317/92; A61K 47/6871; A61K 47/6803; A61K 51/1075; A61K 47/6807; A61K 47/6811; A61K 47/6929; A61K 47/6851; A61K 47/6813; A61K 2039/505; G01N 2333/988; G01N 33/53; G01N 33/563; G01N 33/574
See application file for complete search history.

(56) References Cited

U.S. PATENT DOCUMENTS

| | | | |
|---|---|---|---|
| 6,027,887 A | 2/2000 | Zavada et al. | |
| 6,297,041 B1 | 10/2001 | Zavada et al. | |
| 6,297,051 B1 | 10/2001 | Zavada et al. | |
| 7,910,100 B2 * | 3/2011 | Stuhmer | C07K 16/30 424/133.1 |
| 8,791,243 B2 | 7/2014 | Schenk et al. | |
| 2003/0049828 A1 | 3/2003 | Zavada et al. | |
| 2006/0188981 A1 | 8/2006 | Harris et al. | |
| 2006/0235203 A1 | 10/2006 | Zavada et al. | |
| 2008/0176268 A1 | 7/2008 | Zavada et al. | |
| 2008/0206765 A1 | 8/2008 | Harris et al. | |
| 2009/0162382 A1 | 6/2009 | Bernett et al. | |
| 2011/0150886 A1 * | 6/2011 | Caswell | A61K 39/39558 424/139.1 |
| 2011/0159583 A1 | 6/2011 | Harris et al. | |
| 2012/0177664 A1 * | 7/2012 | Yokoseki | C07K 16/18 424/172.1 |

FOREIGN PATENT DOCUMENTS

| | | |
|---|---|---|
| CA | 2763066 A1 | 5/2000 |
| EP | 2700652 A1 | 2/2014 |
| WO | WO 1988/08854 A1 | 11/1988 |
| WO | WO 1995/04069 A1 | 2/1995 |

(Continued)

OTHER PUBLICATIONS

Lloyd et al. Protein Engineering, Design & Selection 22:159-168 (Year: 2009).*

(Continued)

*Primary Examiner* — Phuong Huynh
(74) *Attorney, Agent, or Firm* — Wolf, Greenfield & Sacks, P.C.

(57) ABSTRACT

The present invention relates to isolated or purified antibodies or fragments thereof specific for Carbohydrate Anhydrase IX (CA-IX) and their use as therapeutic tools. Specifically, the present invention is directed to high-affinity Carbohydrate Anhydrase IX-specific antibodies and fragments thereof and their use as antibody-drug conjugates. Compositions for use in therapy as well as therapeutic methods are also described.

18 Claims, 26 Drawing Sheets

Specification includes a Sequence Listing.

(56) References Cited

FOREIGN PATENT DOCUMENTS

| WO | WO 2003/046560 A2 | 6/2003 |
|---|---|---|
| WO | WO 2003/048328 A2 | 6/2003 |
| WO | WO 2004/076670 A1 | 9/2004 |
| WO | WO 2007/065027 A2 | 6/2007 |
| WO | WO 2008/069864 A2 | 6/2008 |
| WO | WO 2008/091798 A2 | 7/2008 |
| WO | WO 2009/056342 A1 | 5/2009 |
| WO | WO 2011/139375 A1 | 11/2011 |
| WO | WO 2014/044686 A1 | 3/2014 |
| WO | WO 2014/128221 A1 | 8/2014 |

OTHER PUBLICATIONS

Edwards et al., J Mol Biol. 334(1): 103-118 (Year: 2003).*
Paul et al., Fundamental Immunology, (textbook), pp. 292-295 (Year: 1993).*
Rudikoff et al., PNAS 79: 1979-1983 (Year: 1982).*
Kussie et al., J. Immunol. 152: 146-152 (Year: 1994).*
Chen et al., EMBO J., 14: 2784-2794 (Year: 1995).*
Abdiche et al., Expanding the ProteOn XPR36 biosensor into a 36-ligand array expedites protein interaction analysis. Anal Biochem. Apr. 1, 2011;411 (1):139-51.
Ahlskog et al., Human monoclonal antibodies targeting carbonic anhydrase IX for the molecular imaging of hypoxic regions in solid tumours. Br J Cancer. Aug. 18, 2009;101(4):645-57. doi: 10.1038/sj.bjc.6605200. Epub Jul. 21, 2009.
Bao et al., In vivo imaging and quantification of carbonic anhydrase IX expression as an endogenous biomarker of tumor hypoxia. PLoS One. 2012;7(11):e50860. doi: 10.1371/journal.pone.0050860. Epub Nov. 30, 2012.
Bauer et al., Targeted therapy of renal cell carcinoma: synergistic activity of cG250-TNF and IFNg. Int J Cancer. Jul. 1, 2009;125(1):115-23. doi:10.1002/ijc.24359.
Bleumer et al., A phase II trial of chimeric monoclonal antibody G250 for advanced renal cell carcinoma patients. Br J Cancer. Mar. 8, 2004;90(5):985-90.
Brouwers et al., Interferons can upregulate the expression of the tumor associated antigen G250-MN/CA IX, a potential target for (radio)immunotherapy of renal cell carcinoma. Cancer Biother Radiopharm. Aug. 2003;18(4):539-47.
Brouwers et al., Optimization of radioimmunotherapy of renal cell carcinoma: labeling of monoclonal antibody cG250 with 131I, 90Y, 177Lu, or 186Re. J Nucl Med. Feb. 2004;45(2):327-37.
Chang et al., Human anti-CAIX antibodies mediate immune cell inhibition of renal cell carcinoma in vitro and in a humanized mouse model in vivo. Mol Cancer. Jun. 11, 2015;14:119. doi: 10.1186/s12943-015-0384-3.
Chia et al., Prognostic significance of a novel hypoxia-regulated marker, carbonic anhydrase IX, in invasive breast carcinoma. J Clin Oncol. Aug. 15, 2001;19(16):3660-8.
Chopra, [111In]-Labeled chimeric monoclonal antibody cG250 directed against carbonic anhydrase IX. Aug. 6, 2010[Updated Sep. 2, 2010]. In: Molecular Imaging and Contrast Agent Database (MICAD) [Internet]. Bethesda (MD): National Center for Biotechnology Information (US); 2004-2013.
Chopra, [111In]-Labeled divalent Fab fragment of chimeric monoclonal antibody cG250 directed against carbonic anhydrase IX. Aug. 11, 2010[Updated Sep. 2, 2010]. In: Molecular Imaging and Contrast Agent Database (MICAD) [Internet]. Bethesda (MD): National Center for Biotechnology Information (US); 2004-2013.
Chopra, [111In]-Labeled monovalent Fab fragment of chimeric monoclonal antibody cG250 directed against carbonic anhydrase IX. Aug. 11, 2010[Updated Sep. 2, 2010]. In: Molecular Imaging and Contrast Agent Database (MICAD) [Internet]. Bethesda (MD): National Center for Biotechnology Information (US); 2004-2013.
Chopra, 89Zr-Labeled N-suc-desferrioxamine-conjugated anti-carbonic anhydrase IX chimeric monoclonal antibody cG250-F(ab')2 fragments. Aug. 2, 2010[Updated Oct. 14, 2010]. In:

Molecular Imaging and Contrast Agent Database (MICAD) [Internet]. Bethesda (MD): National Center for Biotechnology Information (US); 2004-2013.
Chothia et al., Canonical structures for the hypervariable regions of immunoglobulins. J Mol Biol. Aug. 20, 1987;196(4):901-17.
Chrastina et al., Biodistribution and pharmacokinetics of 125I-labeled monoclonal antibody M75 specific for carbonic anhydrase IX, an intrinsic marker of hypoxia, in nude mice xenografted with human colorectal carcinoma. Int J Cancer. 2003;105(6):873-81.
Chrastina et al., Immunotargeting of human cervical carcinoma xenograft expressing CA IX tumor-associated antigen by 125I-labeled M75 monoclonal antibody. Neoplasma. 2003;50(1):1321.
Csaderova et al., The effect of carbonic anhydrase IX on focal contacts during cell spreading and migration. Front Physiol. Oct. 1, 2013;4:271. doi:10.3389/fphys.2013.00271. eCollection 2013.
De Kruif et al., Leucine zipper dimerized bivalent and bispecific scFv antibodies from a semi-synthetic antibody phage display library. J Biol Chem. Mar. 29, 1996;271 (13):7630-4.
Dereeper et al., Blast-Explorer helps you building datasets for phylogenetic analysis. BMC Evol Biol. Jan. 12, 2010;10:8.
Dereeper et al., Phylogeny.fr: robust phylogenetic analysis for the non-specialist. Nucleic Acids Res. Jul. 1, 2008 ;36(Web Server issue):W465-9. doi:10.1093/nar/gkn180. Epub Apr. 19, 2008.
Ditte et al., Phosphorylation of carbonic anhydrase IX controls its ability to mediate extracellular acidification in hypoxic tumors. Cancer Res. Dec. 15, 2011;71 (24):7558-67.
Dubois et al., Evaluation of hypoxia in an experimental rat tumour model by [(18)F]fluoromisonidazole PET and immunohistochemistry. Br J Cancer. Nov. 29, 2004;91(11):1947-54.
Edgar, Local homology recognition and distance measures in linear time using compressed amino acid alphabets. Nucleic Acids Res. Jan. 16, 2004;32(1):380-5.
Eisenberg et al., Analysis of membrane and surface protein sequences with the hydrophobic moment plot. J. Mol. Biol. 1984;179, 125-142.
Feldhaus et al., Flow-cytometric isolation of human antibodies from a nonimmune *Saccharomyces cerevisiae* surface display library. Nat Biotechnol. Feb. 2003;21(2):163-70.
Fenner et al., Rapid and reliable diagnostic algorithm for detection of Clostridium difficile. (2008) J. Clin. Microbiol. 46, 328-330.
Furjelova et al., Carbonic anhydrase IX: a promising diagnostic and prognostic biomarker in breast carcinoma. Acta Histochem. Jan. 2014;116(1):89-93. doi:10.1016/j.acthis.2013.05.009. Epub Jun. 29, 2013.
Genbank accession No. AGN91378. Trad et al. Aug. 31, 2014.
Gieling et al., Carbonic anhydrase IX as a target for metastatic disease. Bioorg Med Chem. Mar. 15, 2013;21(6):1470-6. doi:10.1016/j.bmc.2012.09.062. Epub Oct. 11, 2012.
Gietz et al., Improved method for high efficiency transformation of intact yeast cells. Nucleic Acids Res. Mar. 25, 1992;20(6):1425.
Gonzales et al., Minimizing the immunogenicity of antibodies for clinical application. Tumour Biol. Jan.-Feb. 2005;26(1):31-43.
Hulikova et al., Intact intracellular tail is critical for proper functioning of the tumor-associated, hypoxia-regulated carbonic anhydrase IX. FEBS Lett. Nov. 19, 2009;583(22):3563-8.
Hunakova et al., Expression of new prognostic markers, peripheral-type benzodiazepine receptor and carbonic anhydrase IX, in human breast and ovarian carcinoma cell lines. Neoplasma. 2007;54(6):541-8.
Jiang et al., Fusion expression of human renal cell carcinoma-associated antigen G250/MC/CA IX in prokaryotic expression system. J South Med University. 2007;27(3):307-309.
Jones et al., Replacing the complementarity-determining regions in a human antibody with those from a mouse. Nature. May 29-Jun. 4, 1986;321(6069):522-5.
Kabat et al., Identical V region amino acid sequences and segments of sequences in antibodies of different specificities. Relative contributions of VH and VL genes, minigenes, and complementarity-determining regions to binding of antibody-combining sites. J Immunol. 1991 ;147:1709-19.
Kral et al., Stabilization of antibody structure upon association to a human carbonic anhydrase IX epitope studied by X-ray crystallog-

(56) References Cited

OTHER PUBLICATIONS raphy, microcalorimetry, and molecular dynamics simulations. Proteins. May 15, 2008;71(3):1275-87.
Lam et al., G250: a carbonic anhydrase IX monoclonal antibody. Curr Oncol Rep. Mar. 2005;7(2):109-15.
Lawrentschuk et al., Investigation of hypoxia and carbonic anhydrase IX expression in a renal cell carcinoma xenograft model with oxygen tension measurements and $^{124}$I-cG250 PET/CT. Urol Oncol. Jul.-Aug. 2011;29(4):411-20. doi: 10.1016/j.urolonc.2009.03.028. Epub Jun. 12, 2009.
Lefranc et al., IMGT unique numbering for immunoglobulin and T cell receptor variable domains and Ig superfamily V-like domains. Dev Comp lmmunol. Jan. 2003;27(1):55-77. Review.
Leung, 177Lu-Benzyl-diethylenetriamine pentaacetic acid-anti-carbonic anhydrase IX small immunoprotein A3. Dec. 2, 2009 Dec 2 [Updated Jan. 12, 2010]. In: Molecular Imaging and Contrast Agent Database (MICAD) [Internet]. Bethesda (MD): National Center for Biotechnology Information (US); 2004-2013.
Li et al., Preliminary biological evaluation of $^{125}$I-labeled anti-carbonic anhydrase IX monoclonal antibody in the mice bearing HT-29 tumors. Nucl Med Commun. Dec. 2011;32(12):1190-3. doi: 10.1097/MNM.0b013e32834bf3e1.
Liao-Chan et al., Quantitative assessment of antibody internalization with novel nomoclonal antibodies against Alexa fluorophores. PLoS One. 015;10(4): e0124708. doi: 10.1371/journal.pone.0124 708.
Lou et al., Targeting tumor hypoxia: suppression of breast tumor growth and metastasis by novel carbonic anhydrase IX inhibitors. Cancer Res. May 1, 2011 ;71 (9):3364-76. Erratum in: Cancer Res. Jun. 15, 2011;71 (12):4325. Cancer Res. Jul. 1, 2011 ;71 (13):4733.
Musher et al., Detection of Clostridium difficile toxin: comparison of enzyme immunoassay results with results obtained by cytotoxicity assay. (2007) J. Clin. Microbial. 45, 2737-2739.
Neri et al., Interfering with pH regulation in tumours as a therapeutic strategy. Nat Rev Drug Discov. Sep. 16, 2011;10(10):767-77. doi: 10.1038/nrd3554.
Nicaise et al., (2004) Affinity transfer by CDR grafting on a nonimmunoglobulin scaffold. Protein Sci. 13(7): 1882-1891.
Nielsen et al., Targeting of bivalent anti-ErbB2 diabody antibody fragments to tumor cells is independent of the intrinsic antibody affinity. Cancer Res. Nov. 15, 2000;60(22):6434-40.
Oosterwijk et al., Immunohistochemical analysis of monoclonal antibodies to renal antigens. Application in the diagnosis of renal cell carcinoma. Am J Pathol. May 1986;123(2):301-9.
Oosterwijk et al., Antibody therapy in renal cell carcinoma. World J Ural. Apr. 2008;26(2):141-6. doi: 10.1007/s00345-008-0236-5. Epub Feb. 1, 2008.
Pacchiano et al., Inhibition of 13-carbonic anhydrases with ureido-substituted benzenesulfonamides. Bioorg Med Chem Lett. Jan. 1, 2011 ;21 (1):102-5. doi: 10.1016/j.bmcl.2010.11.064.
Padlan, A possible procedure for reducing the immunogenicity of antibody variable domains while preserving their ligand-binding properties. Mal lmmunol. 1991;28, 489-498.
Pastorekova et al., A novel quasiviral agent, MaTu, is a two-component system. Virology. Apr. 1992;187(2):620-6.
Pastorekova et al., Carbonic anhydrases: current state of the art, therapeutic applications and future prospects. J Enzyme lnhib Med Chem. Jun. 2004;19(3):199-229.
Perez-Sayans et al., Inhibition of V-ATPase and carbonic anhydrases as interference strategy with tumor acidification processes. Curr Pharm Des. 2012;18(10):1407-13.
Petrul et al., Therapeutic mechanism and efficacy of the antibody-drug conjugate BAY 79-4620 targeting human carbonic anhydrase 9. Mal Cancer Ther. Feb. 2012;11(2):340-9. doi: 10.1158/1535-7163.MCT-11-0523. EpubDec. 6, 2011.
Planche et al., (2008) Diagnosis of Clostridium difficile infection by toxin detection kits: a systematic review. Lancet Infect. Dis. 8, 777-784.
Queen et al., A humanized antibody that binds to the interleukin 2 receptor. Proc Natl Acad Sci U S A. Dec. 1989;86(24):10029-33.

Ridgway et al., 'Knobs-into-holes' engineering of antibody CH3 domains for heavy chain heterodimerization. (1996) Protein Eng. 9, 617-621.
Riechmann et al., Reshaping human antibodies for therapy. Nature. Mar. 24, 1988;332(6162):323-7.
Riesterer et al., Enhanced response to C225 of A431 tumor xenografts growing in irradiated tumor bed. Radiother Oncol. Sep. 2009;92(3):383-7. doi: 10.1016/j.radonc.2009.07.009. Epub Aug. 18, 2009.
Russmann et al., Evaluation of three rapid assays for detection of Clostridium difficile toxin A and toxin B in stool specimens. (2007) Eur. J. Clin. Microbial. Infect. Dis. 26, 115-119.
Shan, 125I-Labeled mouse anti-human carbonic anhydrase IX monoclonal antibody. May 3, 2012 [Updated May 30, 2012]. In: Molecular Imaging and Contrast Agent Database (MICAD) [Internet]. Bethesda (MD): National Center for Biotechnology Information (US); 2004-2013.
Sloan et al., Comparison of real-time PCR for detection of the tcdC gene with four toxin immunoassays and culture in diagnosis of Clostridium difficile infection. (2008) J. Clin. Microbial. 46, 1996-2001.
Stillebroer et al., Phase 1 radioimmunotherapy study with lutetium 177-labeled anti-carbonic anhydrase IX monoclonal antibody girentuximab in patients with advanced renal cell carcinoma. Eur Urol. Sep. 2013;64(3):478-85. doi:10.1016/j.eururo.2012.08.024. Epub Aug. 21, 2012.
Supuran, Diuretics: from classical carbonic anhydrase inhibitors to novel applications of the sulfonamides. Curr Pharm Des. 2008;14(7):641-8.
Surfus et al., Anti-renal-cell carcinoma chimeric antibody G250 facilitates antibody-dependent cellular cytotoxicity with in vitro and in vivo interleukin-2-activated effectors. J lmmunother Emphasis Tumor lmmunol. May 1996;19(3):184-91.
Svastova et al., Carbonic anhydrase IX interacts with bicarbonate transporters in lamellipodia and increases cell migration via its catalytic domain. J Biol Chem. Jan. 27, 2012;287(5):3392-402. doi: 10.1074/jbc.M111.286062. Epub Dec. 14, 2011.
Takacova et al., Hypoxia-inducible expression of the mouse carbonic anhydrase IX demonstrated by new monoclonal antibodies. Int J Oncol. Nov. 2007;31(5):1103-10.
Tempest et al., Reshaping a human monoclonal antibody to inhibit human respiratory syncytial virus infection in vivo. Biotechnology (N Y). Mar. 1991;9(3):266-71.
Thiry et al., Targeting tumor-associated carbonic anhydrase IX in cancer therapy. Trends Pharma col. Sci. Nov. 2006;27(11 ):566-73. Epub Sep. 25, 2006.
Tokarova et al., Feasibility and constraints of particle targeting using the antigen-antibody interaction. Nanoscale. Dec. 7, 2013;5(23):11490-8.
Tsurushita et al., (2005) Design of humanized antibodies: From anti-Tac to Zenapax. Methods 36, 69-83.
Turgeon et al., Six rapid tests for direct detection of Clostridium difficile and its toxins in fecal samples compared with the fibroblast cytotoxicity assay. (2003) J. Clin. Microbial. 41, 667-670.
Vidlickova et al., Apoptosis-induced ectodomain shedding of hypoxia-regulated carbonic anhydrase IX from tumor cells: a double-edged response to chemotherapy. BMC Cancer. Mar. 19, 2016;16:239. doi: 10.1186/s12885-016-2267-4.
Vissers et al., The renal cell carcinoma-associated antigen G250 encodes a human leukocyte antigen (HLA)-A2.1-restricted epitope recognized by cytotoxic T lymphocytes. Cancer Res. Nov. 1, 1999;59(21):5554-9.
Wykoff et al., Hypoxia-inducible expression of tumor-associated carbonic anhydrases. Cancer Res. Dec. 15, 2000;60(24):7075-83.
Zatovicova et al., Carbonic anhydrase IX as an anticancer therapy target: preclinical evaluation of internalizing monoclonal antibody directed to catalytic domain. Curr Pharm Des. 2010;16(29):3255-63.
Zatovicova et al., Ectodomain shedding of the hypoxia-induced carbonic anhydrase IX is a metalloprotease-dependent process regulated by TACE/ADAM17. Br J Cancer. Nov. 28, 2005;93(11):1267-76.
Zat'ovicová et al., Monoclonal antibodies generated in carbonic anhydrase IX-deficient mice recognize different domains of tumour-

(56) References Cited

OTHER PUBLICATIONS associated hypoxia-induced carbonic anhydrase IX. J Immunol Methods. Nov. 2003;282(1-2):117-34.
Zavada et al., Human tumour-associated cell adhesion protein MN/CA IX: identification of M75 epitope and of the region mediating cell adhesion. Br J Cancer. Jun. 2000;82(11):1808-13.
Zavadova et al., Carbonic anhydrase IX (CA IX) mediates tumor cell interactions with microenvironment. Oncol Rep. May 2005;13(5):977-82.
Zhang et al., A pentavalent single-domain antibody approach to tumor antigen discovery and the development of novel proteomics reagents. (2004b) J. Mol. Biol. 335, 49-56.
Zhu et al., COMBODY: one-5 domain antibody multimer with improved avidity. Immunol Cell Biol. Aug. 2010;88(6):667-75. doi: 10.1038/icb.2010.21. Epub Mar. 9, 2010.

\* cited by examiner

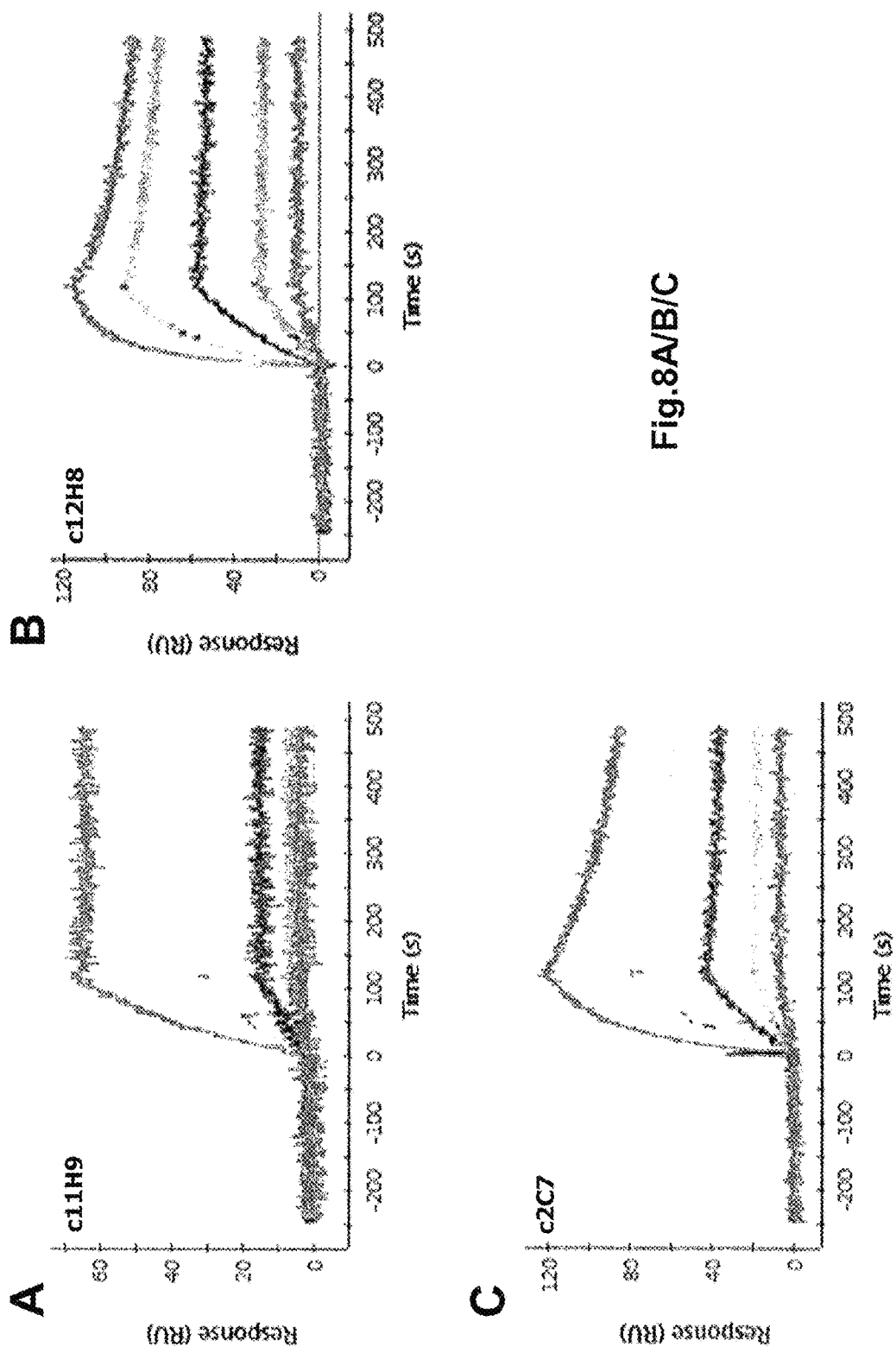
Fig.8A/B/C

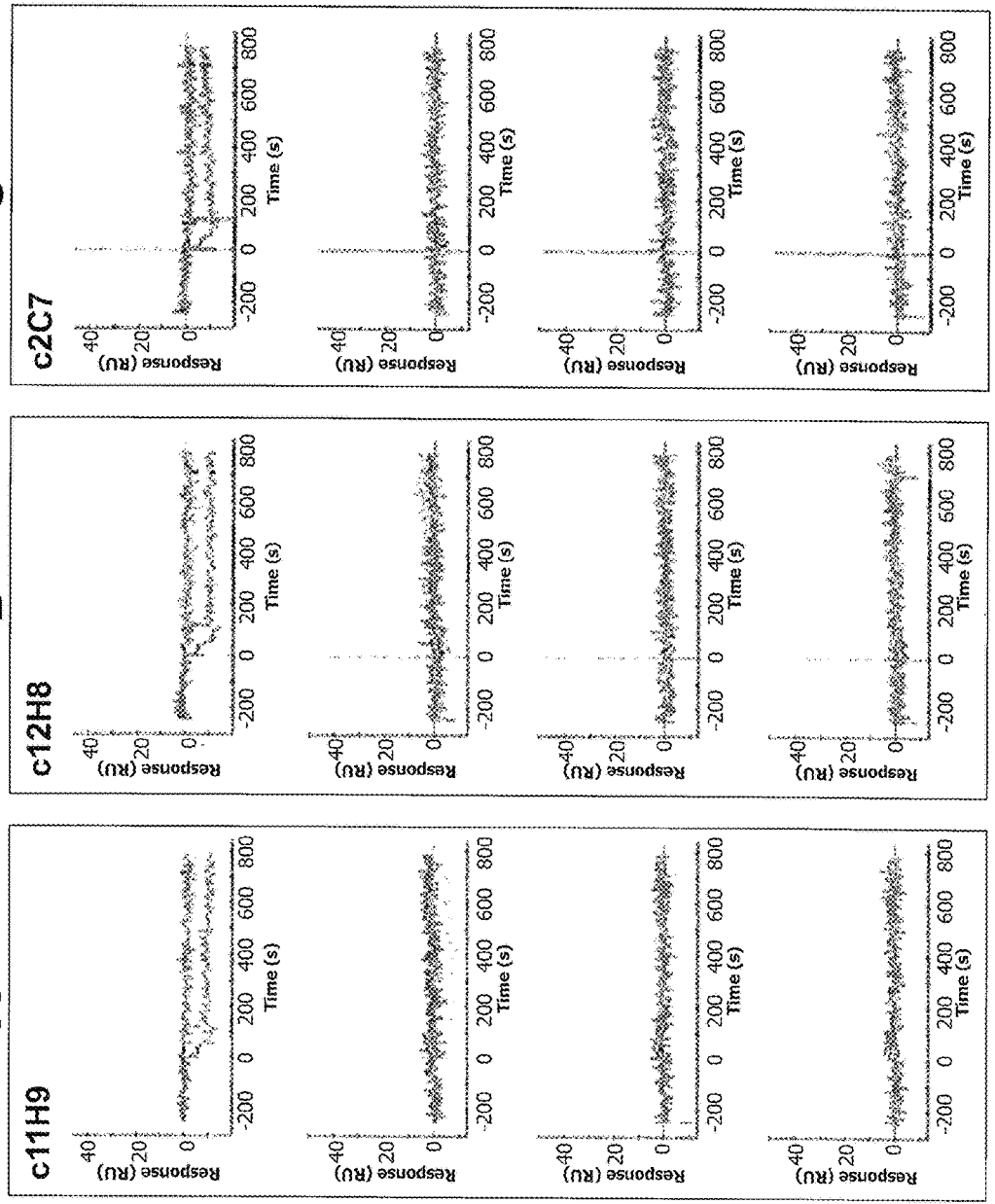

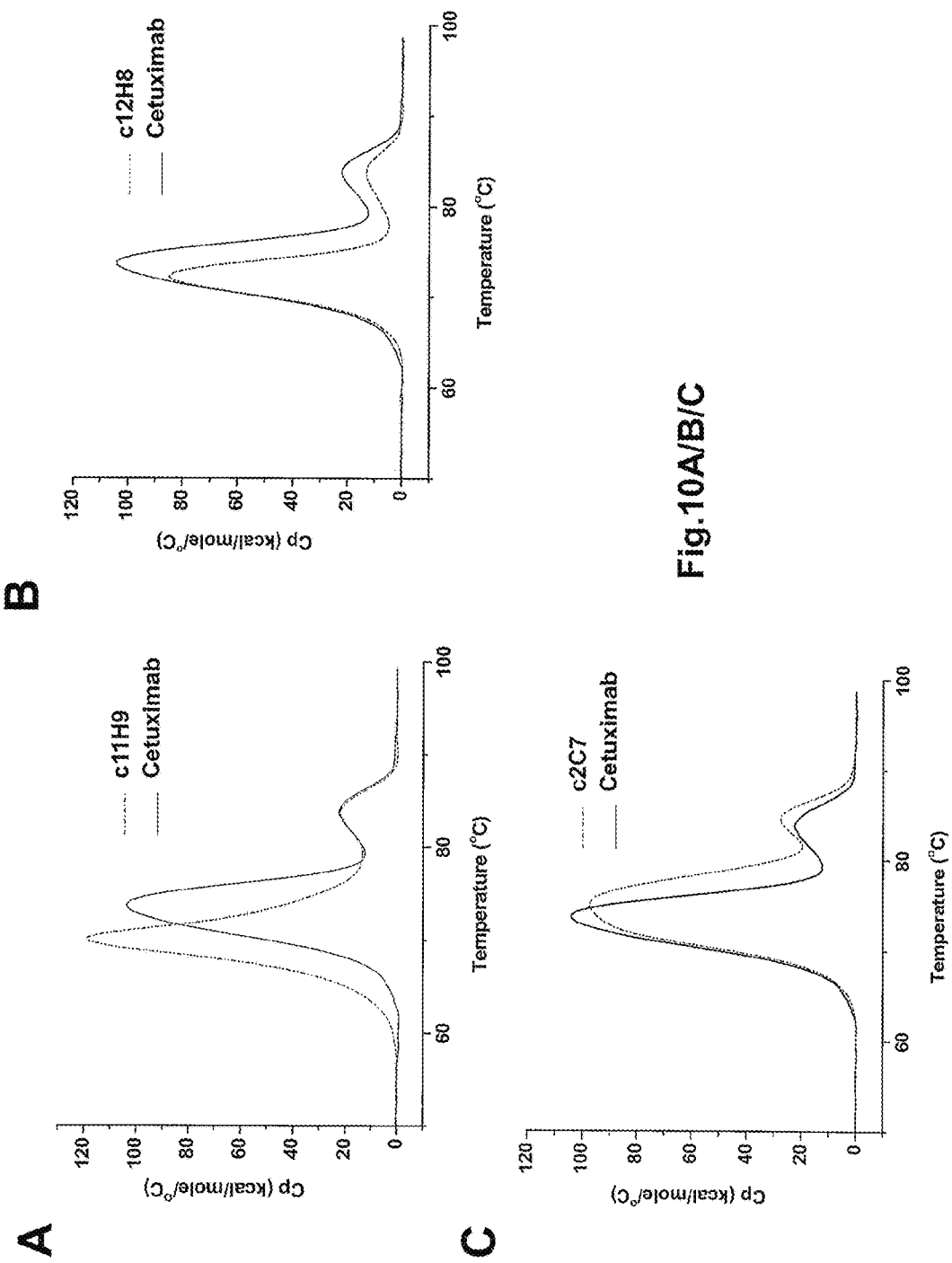
Fig.10A/B/C

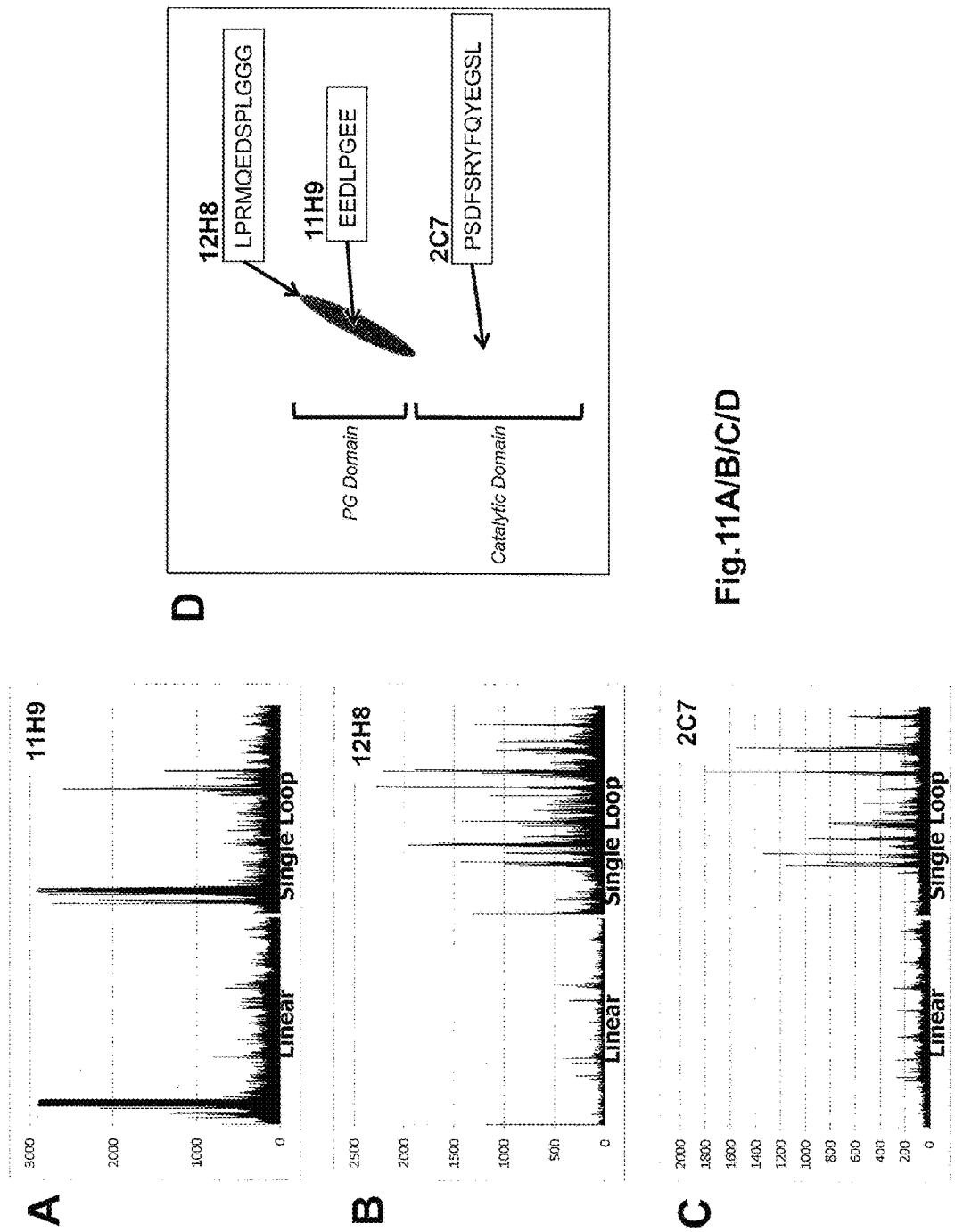
Fig.11A/B/C/D

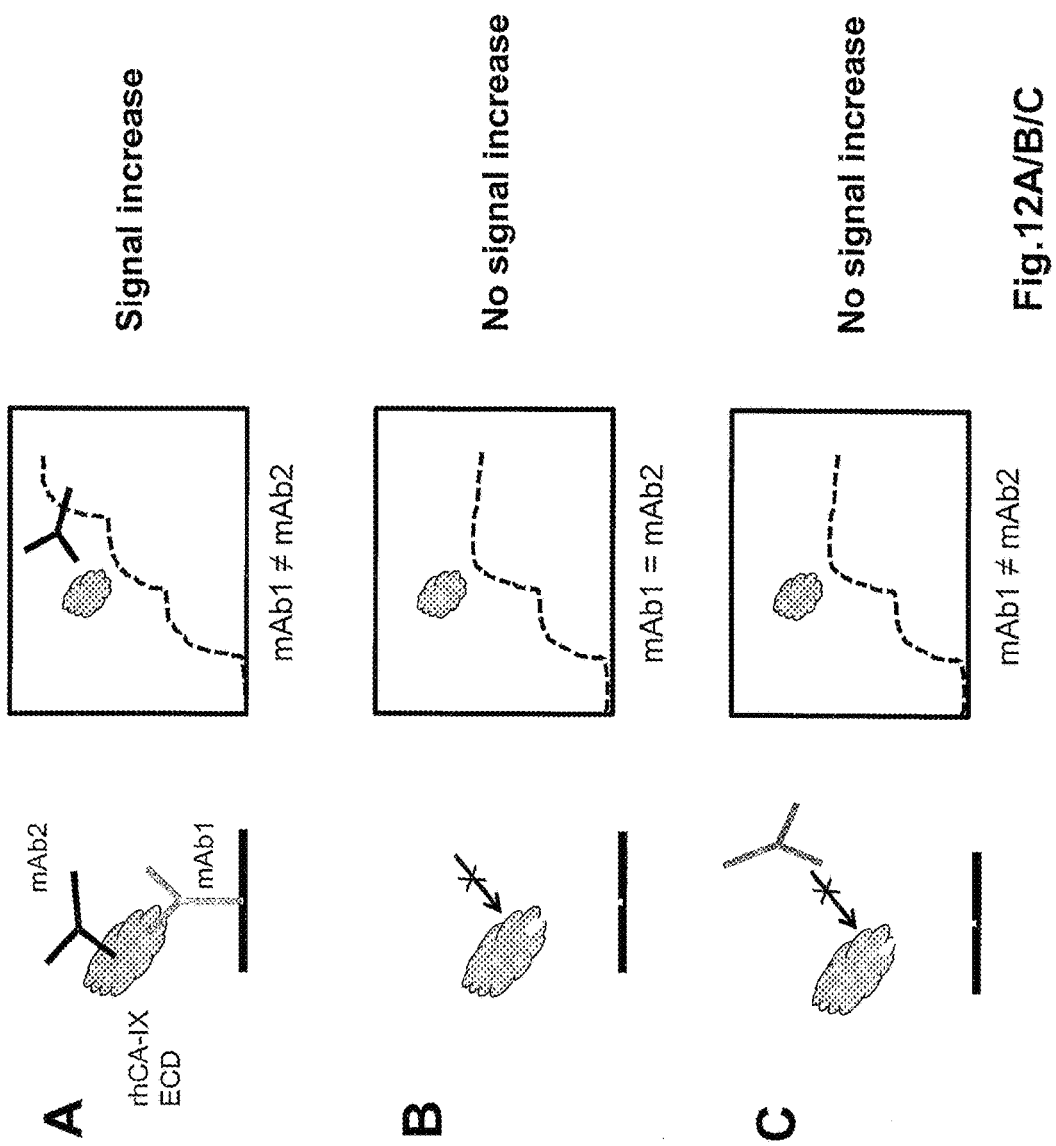
Fig.12A/B/C

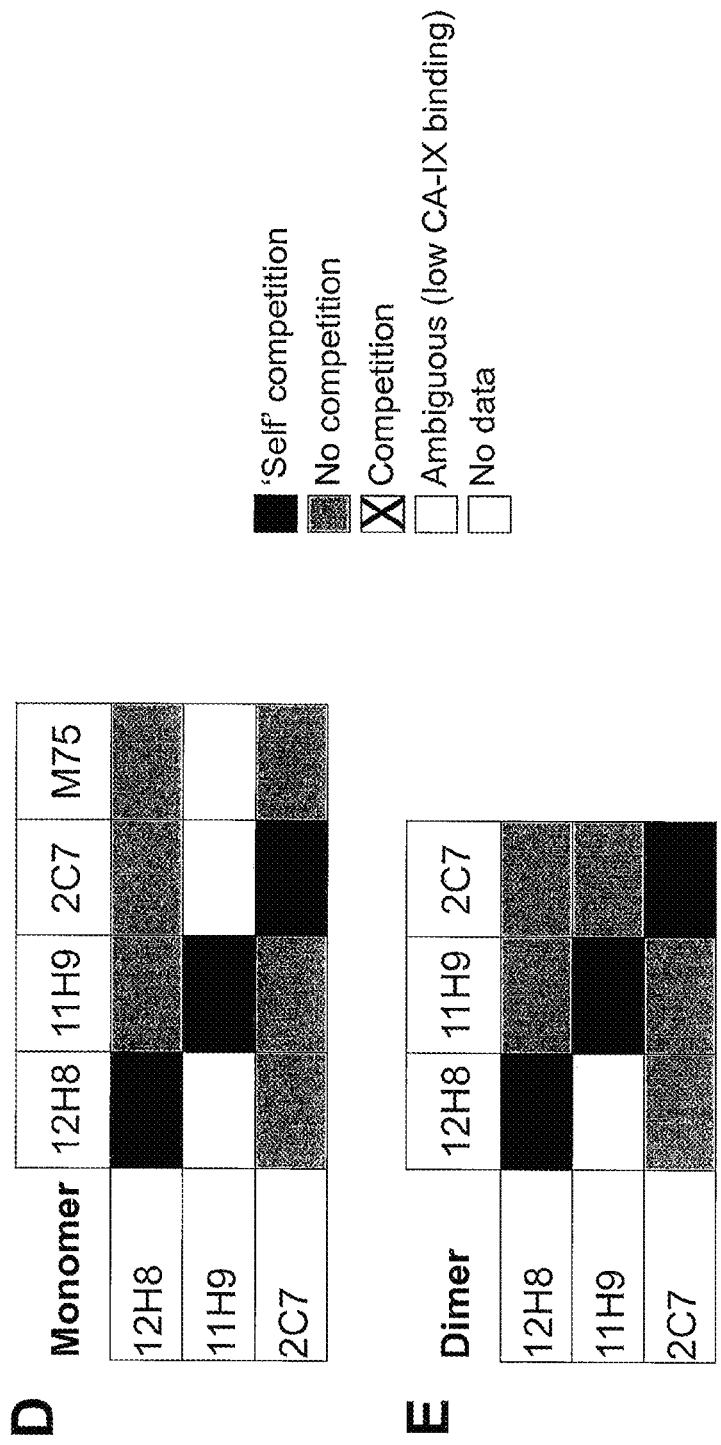
Fig.12D/E

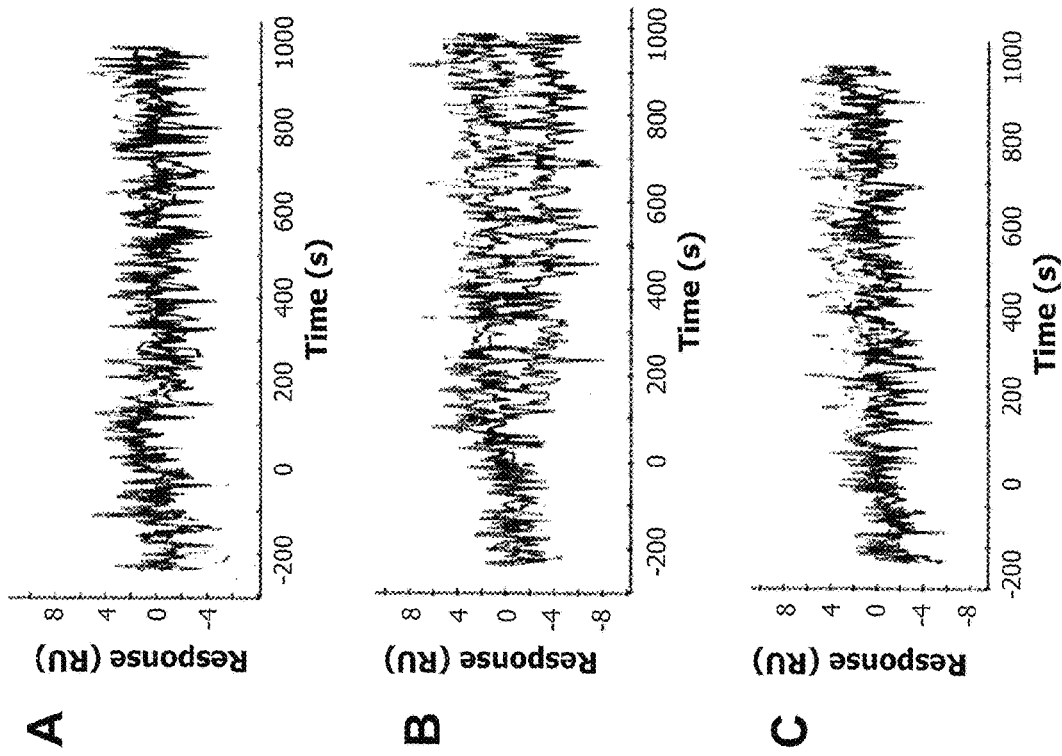
Fig.20A/B/C

CARBONIC ANHYDRASE IX-SPECIFIC ANTIBODIES AND USES THEREOF

RELATED APPLICATIONS

This application is a national stage filing under 35 U.S.C. § 371 of International Application No. PCT/IB2016/053448, filed Jun. 10, 2016, and claims the benefit under 35 U.S.C. § 119(e) of U.S. provisional application Ser. No. 62/173,405, filed Jun. 10, 2015, the entire contents of each of which is incorporated by reference herein in its entirety.

FIELD OF THE INVENTION

The present invention relates to Carbohydrate Anhydrase IX-specific antibodies, fragments thereof, and uses thereof. More specifically, the present invention relates to high-affinity Carbohydrate Anhydrase IX-specific antibodies and fragments thereof and their use as antibody-drug conjugates.

BACKGROUND OF THE INVENTION

Carbonic anhydrases (CA) are a family of 16 distinct but related metalloenzymes that catalyze the reversible hydration of carbon dioxide ($CO_2$) to bicarbonate ($HCO_3^-$) and protons ($H^+$) (Pastorekova et al., 2004; see FIG. 1). Members of the CA, with the exception of CA-IX and CA-XII, can be found in many normal human organs, tissues and subcellular compartments where they play an important role in the regulation of the extracellular and intracellular pH (pHe and pHi, respectively) and the secretion of electrolytes (Zatovicova et al., 2005; Thiry et al., 2006).

In addition to its pH-balancing activities, CA-IX has been shown to be involved in cell adhesion and migration (Svastova et al., 2011) and has been associated with cancer progression, metastasis and poor clinical outcome (Neri et al., 2011). CA-IX (also known as MN, P54/58N or Renal Cell Carcinoma (RCC)-associated protein G250) is a transmembrane protein with an extracellular catalytic site and an $NH_2$-terminal proteoglycan (PG)-like domain. The C-terminal intracellular portion of CA-IX is involved in the inside-out regulation of the extracellular catalytic domain through the phosphorylation of Thr-443 by protein kinase A (PKA) (Hulikova et al., 2009; Ditte et al., 2011). Expression of CA-IX is tightly controlled by hypoxia-inducible factor 1 alpha (HIF-1a). CA-IX is expressed on the surface of tumor cells located in pre-necrotic areas of tumors (Wykoff et al., 2000) where it is involved in promoting tumor cell survival, the accelerated degradation of the extracellular matrix (ECM) and metastasis.

CA-IX has a very selective expression pattern in normal tissue. The mucosa of the gall bladder and stomach express high levels of CA-IX. Low expression levels of CA-IX levels can be found in the intestinal epithelium, and even lower levels in pancreatic duct epithelium, male reproductive organs, and cells that line the body cavity. All other normal tissues do not express CA-IX. Cancerous tissues however, especially those of the cervix, kidney and lung, express high levels of CA-IX thus making CA-IX a very attractive therapeutic tumor target. While various small molecule inhibitors have been shown to effectively inhibit the catalytic activity of CA-IX (Supuran et al., 2008; Neri et al., 2011; Pacchiano et al., 2010; Lou et al., 2011), the lack of target specificity has been an ongoing challenge.

In order to address this issue and to confer specificity in targeting CA-IX, various antibodies have been raised against this important target.

One of the earliest monoclonal antibodies (mAb) raised against CA-IX is M75 (Pastorekova et al., 1992), which binds to CA-IX's PG-like domain. M75 has been predominately used as tool for CA-IX detection in vitro and in vivo (Chrastina et al., 2003a, 2003b; Zatovicova et al., 2010).

A second anti-CA-IX mAb, mAb G250 (Oosterwijk et al., 1986), was shown to interact with CA-IX's catalytic domain without however inhibiting its enzyme activity. A chimeric version of G250 (designated cG250) was developed as a therapeutic antibody (Surfus et al., 1996; Oosterwijk, 2008) with a mechanism of action that was shown to rely predominantly on an Antibody-Dependent Cellular Cytotoxicity (ADCC) response. cG250 does however not improve the disease-free survival rate of patients (>6-year span) compared to a placebo (Bleumer et al., 2004). Despite the lack of therapeutic potential of the cG250 antibody itself, the mAb continues to be developed for the treatment of cancer in combination with IL2 or IFN-α, as an imaging diagnostic agent and for in vitro diagnostics (IVD) immunohistochemistry (IHC) assays.

In addition, cG250 is also used as a vehicle for the delivery of radionuclides. Specifically, Brouwers et al. (2004) successfully used cG250 to shuttle $^{177}$Lu and $^{90}$Y into tumor cells, causing growth retardation of xenograft tumors. Clinical phase II/III studies with these labeled mAbs are currently underway (Stillebroer et al., 2012). Also in development are antibody-drug conjugates (ADC) based on cG250, however little is known their efficacy. Such antibody-drug conjugates are an attractive option in cancer therapy, as they combine the selective targeting ability of the antibody with the cell-killing capabilities of the cytotoxic drug.

In view of its specific tumor expression, CA-IX as a therapeutic target has become an active area of research. Although several antibodies have been identified showing enzyme inhibition, only one has been evaluated in vivo (VII/20 mAb; Zatovicova et al., 2010). Similarly, the use of these mAb for the delivery of cytotoxic agents or radionuclides to tumor cells expressing CA-IX has been an area of much investigative research. For example, Petrul et al. (2012) isolated the 3ee9 Fab, which was subsequently engineered into a mAb and further developed as an ADC by conjugation to monomethyl auristatin E. This ADC showed potent antitumor efficacy and a Phase I clinical trial to determine the maximal tolerated dose (MTD) was terminated early due to safety concerns.

While there is interest and research activity surrounding the use of CA-IX as a target for ADC, there is currently little certainty surrounding ongoing investigations involving these known antibodies. The ability of an antibody to function as an ADC is difficult to predict, and relies on design strategies, target biology and routing behaviour that go beyond its ability to be internalized by its specific target. Therefore, there remains a need in the art to develop further anti-CA-IX antibodies that have potential as ADC candidates. Needless to say such antibodies should display a high target affinity and specific while avoiding off-target effects, toxicity, and therapeutic resistance.

SUMMARY OF THE INVENTION

The present invention relates to Carbohydrate Anhydrase IX-specific antibodies, fragments thereof, and uses thereof. More specifically, the present invention relates to high-affinity Carbohydrate Anhydrase IX-specific antibodies and fragments thereof and their use as antibody-drug conjugates.

The present invention provides an isolated or purified antibody or fragment thereof, comprising
a) a light chain comprising a complementarity determining region (CDR) L1 sequence selected from the group consisting of:

```
                                 (SEQ ID NO: 1)
RASGNIHNYLA;

(SEQ ID NO: 7)
RSSQSLVHSNGNTYLH;
and (SEQ ID NO: 13)
KSSQSLLDSDGKTYLN,
``` a CDR L2 sequence selected from the group consisting of:

```
                                 (SEQ ID NO: 2)
NTITLAD;

(SEQ ID NO: 8)
KVSNRFS;
and (SEQ ID NO: 14)
LVSKLDS,
``` and
a CDR L3 sequence selected from the group consisting of:

```
QHFWNIPFT;         (SEQ ID NO: 3)

SQNTHVPPT;         (SEQ ID NO: 9)
and

CQGTHFPW,          (SEQ ID NO: 15)
``` and
a) a heavy chain comprising a complementarity determining region (CDR) H1 sequence selected from the group consisting of:

```
GFTFTSCYIH;        (SEQ ID NO: 4)

GFTFNTYAMY;        (SEQ ID NO: 10)
and

GYTFTNYGMN,        (SEQ ID NO: 16)
``` a CDR H2 sequence selected from the group consisting of:

```
WIYPGNGNTKYNEIFKG;      (SEQ ID NO: 5)

RIRSKSNNYAIYYADSVKD;    (SEQ ID NO: 11)
and

WINTYTGEPTYADDFKG,      (SEQ ID NO: 17)
``` and
a CDR H3 sequence selected from the group consisting of:

```
GDTTANTMDY;        (SEQ ID NO: 6)

GWDWFAY;           (SEQ ID NO: 12)
and

GGIATPTSY,         (SEQ ID NO: 18)
``` wherein the antibody or fragment thereof specifically binds the extracellular domain of Carbohydrate Anhydrase IX.

In a more specific example, the isolated or purified antibody or fragment thereof may be selected from the group consisting of:
a) a light chain comprising CDR L1 of sequence RASGNIHNYLA (SEQ ID NO:1), CDR L2 of sequence NTITLAD (SEQ ID NO:2), and CDR L3 of sequence QHFWNIPFT (SEQ ID NO:3); and a heavy chain comprising CDR H1 of sequence GFTFTSCYIH (SEQ ID NO:4), CDR H2 of sequence WIYPGNGNTKYNEIFKG (SEQ ID NO:5), and CDR H3 of sequence GDTTANTMDY (SEQ ID NO:6); and wherein the antibody or fragment thereof binds the catalytic domain of CA-IX;
b) a light chain comprising CDR L1 of sequence RSSQSLVHSNGNTYLH (SEQ ID NO:7), CDR L2 of sequence KVSNRFS (SEQ ID NO:8), CDRL3 of sequence SQNTHVPPT (SEQ ID NO:9); and a heavy chain comprising CDR H1 of sequence GFTFNTYAMY (SEQ ID NO:10), CDR H2 of sequence RIRSKSNNYAIYYADSVKD (SEQ ID NO:11), and CDR H3 of sequence GWDWFAY(SEQ ID NO:12); and wherein the antibody or fragment thereof binds the PG-like domain of CA-IX; and
c) a light chain comprising CDR L1 of sequence KSSQSLLDSDGKTYLN (SEQ ID NO:13), CDR L2 of sequence LVSKLDS (SEQ ID NO:14), CDRL3 of sequence CQGTHFPW (SEQ ID NO:15); and a heavy chain comprising CDR H1 of sequence GYTFTNYGMN (SEQ ID NO:16), CDR H2 of sequence WINTYTGEPTYADDFKG (SEQ ID NO:17), and CDR H3 of sequence GGIATPTSY (SEQ ID NO:18); and wherein the antibody or fragment thereof binds the PG-like domain of CA-IX.

In one embodiment, the isolated or purified antibody or fragment thereof may comprise
a) a variable light (VL) domain of sequence selected from the group consisting of:

```
                                           (SEQ ID NO: 19)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELK,
                                           (SEQ ID NO: 21)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQNTHVP

PTFGGGTKLEIK,
and
                                           (SEQ ID NO: 23)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCCQGTHFP

WTFGGGTKLEIK;
``` b) a variable heavy ($V_H$) domain of sequence selected from the group consisting of:

```
                                           (SEQ ID NO: 20)
QVQLQQSGPELVKPGASVRISCKASGFTFTSCYIHWMKQRPGQGLEWIGW

IYPGNGNTKYNEIFKGRATLTTDKSSTAYMQLSSLTSEDSAVYFCARGD

TTANTMDYWGQGTSVTVSS;
```

-continued (SEQ ID NO: 22)
EVQLVESGGRLVQPKGSLKLSCAASGFTFNTYAMYWIRQAPGKGLEWVAR

IRSKSNNYAIYYADSVKDRFTISRDDSQSMLYLQMNNLKTEDTAMYYCVR

GWDWFAYWGQGTPVTVSA;
and (SEQ ID NO: 24)
QIQLVQSGPELKKPGETVKISCKASGYTFTNYGMNWVQQAPGKGLKWMGW

INTYTGEPTYADDFKGRFAFSLETSASTAYLQINNLKNEDMATYFCARGG

IATPTSYWGQGTTLTVSS;

or c) a sequence substantially identical to the variable light (VL) domain of a) or the variable heavy (VH) domain of b) as described above.

The antibody or fragment thereof just defined specifically binds to the extracellular domain of CA-IX.

In specific, non-limiting examples, the isolated or purified antibody or fragment thereof of the present invention may comprise a) a variable light (V$_L$) domain of sequence (SEQ ID NO: 19)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELK and/or variable heavy (V$_H$) domain of sequence (SEQ ID NO: 20)
QVQLQQSGPELVKPGASVRISCKASGFTFTSCYIHWMKQRPGQGLEWIGW

IYPGNGNTKYNEIFKGRATLTTDKSSSTAYMQLSSLTSEDSAVYFCARGD

TTANTMDYWGQGTSVTVSS;

b) a variable light (V$_L$) domain of sequence (SEQ ID NO: 21)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQNTHVP

PTFGGGTKLEIK and/or variable heavy (V$_H$) domain of sequence (SEQ ID NO: 22)
EVQLVESGGRLVQPKGSLKLSCAASGFTFNTYAMYWIRQAPGKGLEWVAR

IRSKSNNYAIYYADSVKDRFTISRDDSQSMLYLQMNNLKTEDTAMYYCVR

GWDWFAYWGQGTPVTVSA;

c) a variable light (V$_L$) domain of sequence (SEQ ID NO: 23)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCCQGTHFP

WTFGGGTKLEIK and/or variable heavy (V$_H$) domain of sequence (SEQ ID NO: 24)
QIQLVQSGPELKKPGETVKISCKASGYTFTNYGMNWVQQAPGKGLKWMGW

INTYTGEPTYADDFKGRFAFSLETSASTAYLQINNLKNEDMATYFCARGG

IATPTSYWGQGTTLTVSS;

or a sequence substantially identical thereto.

The isolated or purified antibody or fragment thereof as described herein may exhibit a high degree of internalization, thus rendering it suitable as a delivery agent for the intracellular delivery of drugs or toxins.

The isolated or purified antibody or fragment thereof as described herein may a full-length IgG, Fv, scFv, Fab, or F(ab')$_2$; the antibody or fragment thereof may also comprise framework regions from IgA, IgD, IgE, IgG, or IgM. The isolated or purified antibody or fragment thereof of the present invention may be chimeric; for example, and without wishing to be limiting, such a chimeric antibody or fragment thereof may comprise the V$_L$ and V$_H$ domains from mouse and framework regions (constant domains) from human IgG1, more specifically human kappa 1 light chain and human IgG1 heavy chain In a yet more specific non-limiting example, the isolated or purified antibody or fragment thereof of the present invention may comprise a) a variable light (V$_L$) domain comprising the sequence (SEQ ID NO: 25)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC and variable heavy (V$_H$) domain comprising the sequence (SEQ ID NO: 26)
QVQLQQSGPELVKPGASVRISCKASGFTFTSCYIHWMKQRPGQGLEWIGW

IYPGNGNTKYNEIFKGRATLTTDKSSSTAYMQLSSLTSEDSAVYFCARGD

TTANTMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG;

b) a variable light (V$_L$) domain comprising the sequence (SEQ ID NO: 27)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQNTHVP

PTFGGGTKLEIKRTVAAPSVFIFPPSDEQLKSGTASVVCLLNNFYPREAK

-continued

VQWKVDNALQSGNSQESVTEQDSKDSTYSLSSTLTLSKADYEKHKVYACE

VTHQGLSSPVTKSFNRGEC and variable heavy (V$_H$) domain comprising the sequence (SEQ ID NO: 28)
EVQLVESGGRLVQPKGSLKLSCAASGFTFNTYAMYWIRQAPGKGLEWVAR

IRSKSNNYAIYYADSVKDRFTISRDDSQSMLYLQMNNLKTEDTAMYYCVR

GWDWFAYWGQGTPVTVSAASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG;

c) a variable light (V$_L$) domain comprising the sequence (SEQ ID NO: 29)
DVVMTQTPLTLSVTIGQPASISCKSSQSLLDSDGKTYLNWLLQRPGQSPKR

LIYLVSKLDSGVPDRFTGSGSGTDFTLKISRVEAEDLGVYYCCQGTHFPWT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC and variable heavy (V$_H$) domain comprising the sequence (SEQ ID NO: 30)
QIQLVQSGPELKKPGETVKISCKASGYTFTNYGMNWVQQAPGKGLKWMGW

INTYTGEPTYADDFKGRFAFSLETSASTAYLQINNLKNEDMATYFCARGG

IATPTSYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG;

or a sequence substantially identical thereto.

The present invention also provides a nucleic acid molecule encoding the isolated or purified antibody or fragment thereof as described herein. A vector comprising the nucleic acid molecule as just described is also provided.

The isolated or purified antibody or fragment thereof as described herein may be immobilized onto a surface, or may be linked to a cargo molecule. The cargo molecule may be a detectable agent, a therapeutic agent, a drug, a peptide, an enzyme, a growth factor, a cytokine, a receptor trap, an antibody or fragment thereof (e.g., IgG, scFv, Fab, V$_H$H, etc) a chemical compound, a carbohydrate moiety, DNA-based molecules (anti-sense oligonucleotide, microRNA, siRNA, plasmid), a cytotoxic agent, viral vector (adeno-, lenti-, retro-), one or more liposomes or nanocarriers loaded with any of the previously recited types of cargo molecules, or one or more nanoparticle, nanowire, nanotube, or quantum dots. In a specific, non-limiting example, the cargo molecule is a cytotoxic agent.

Additionally, the present invention provides a composition comprising one or more than one isolated or purified antibody or fragment thereof as described herein and a pharmaceutically-acceptable carrier, diluent, or excipient.

An in vitro method of detecting CA-IX is also provided, the method comprising
 a) contacting a tissue sample with one or more than one isolated or purified antibody or fragment thereof as described herein linked to a detectable agent; and
 b) detecting the detectable agent linked to the antibody or fragment thereof bound to CA-IX in the tissue sample.

In the method described above, the method may detect CA-IX in circulating cells and the sample may be a serum sample. In the method as described, the step of detecting (step b) may be performed using optical imaging, immunohistochemistry, molecular diagnostic imaging, ELISA, or other suitable method.

The present invention further provides an in vivo method of detecting CA-IX expression in a subject, comprising:
 a) administering one or more than one isolated or purified antibody or fragment thereof as described herein linked to a detectable agent to the subject; and
 b) detecting the detectable agent linked to the antibody or fragment thereof bound to CA-IX.

In the method described just described, the step of detecting (step b)) is performed using PET, SPECT, fluorescence imaging, or any other suitable method.

The present invention additionally provides a method of transporting a molecule of interest into cells expressing CA-IX. The method may comprise administering one or more than one isolated or purified antibody or fragment thereof as described herein linked to the molecule of interest to a subject. Once administered, the one or more than one isolated or purified antibody or fragment thereof delivers the molecule of interest to cells expressing CA-IX in the subject. The molecule of interest may be any suitable molecule, for example a molecule selected from the group consisting of a detectable agent, a therapeutic agent, a drug, a peptide, an enzyme, a growth factor, a cytokine, a receptor trap, an antibody or fragment thereof (e.g., IgG, scFv, Fab, V$_H$H, etc) a chemical compound, a carbohydrate moiety, DNA-based molecules (anti-sense oligonucleotide, microRNA, siRNA, plasmid), a cytotoxic agent, viral vector (adeno-, lenti-, retro-), one or more liposomes loaded with any of the previously recited types of cargo molecules, or one or more nanoparticle, nanowire, nanotube, or quantum dots. In a non-limiting example, the molecule of interest is a cytotoxic agent.

Presently, three novel antibodies (11H9, 12H8 and 2C7) have been identified that specifically bind human CA-IX. Two of the monoclonal antibodies (11H9 and 2C7) were shown to have a slight preference for the recombinant human CA-IX dimer over the monomer, while mAb 12H8 binds the rhCA-IX ECD dimer. The antibodies were also engineered as chimeric antibodies using the human IgG1 heavy chain. The resulting recombinantly-expressed chimeric antibodies (c11H9, c12H8 and c2C7) behaved similarly to the hybridoma-expressed mAb. SPR experiments showed that all three chimeric mAb have a relative slow off-rate, showing binding characteristics similar to the original mAb. The anti-CA-IX mAb also showed no inhibition of the enzyme activity of rhCA-IX ECD. The minimal epitopes of the antibodies were determined by epitope mapping using Yeast Surface Display. The minimal epitope for c12H8 was determined to be LPRMQEDSP (SEQ ID NO:52; corresponding to aa 40-48 of CA-IX); and that of c11H9 was determined to be EDLPGEED (SEQ ID NO:53; corresponding to aa 81-88 and aa 87-94 of CA-IX. It was also shown that mAb 12H8, 11 H9 and 2C7 were either equal to or better than the M75 mAb (a known antibody) in reducing cell viability. Chimeric (c) 11H9, c12H8 and c2C7 antibodies were similarly tested and shown to retain the ADC potential of their respective monoclonal versions. Additionally, ADC assays using non-conjugated chimeric antibodies and chimeric antibodies conjugated to DM1 (c11H9-DM1, c12H8-DM1 and c2C7-DM1) were performed. Results showed the specificity of c11H9-DM1, c12H8-DM1 and c2C7-DM1 in terms of killing the cells, whereas the unconjugated antibodies had no effect.

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 8 shows SPR sensorgrams for the recombinantly expressed and purified chimeric mAb c11H9 (FIG. 8A), c12H8 (FIG. 8B) and c2C7 (FIG. 8C). An anti-human Fc antibody was directly immobilized onto the chip surface via amine coupling chemistry. This immobilized antibody was used to capture mAbs on the. Purified rhCA-IX ECD dimer was flowed at various concentrations over the captured mAbs and kinetic rate constants for association and dissociation measured to determine the binding constant $K_D$.

FIG. 9 shows the real-time SPR binding of the recombinantly expressed c11H9 (FIG. 9A), c12H8 (FIG. 9B) and c2C7 (FIG. 9C) to rhCA-IV, rhCA-XII, rhCA-XIV, and rmCA-IX. Data indicate that c11H9, c12H8 and c2C7 are specific for the hCA-IX, as no binding was detected against other relevant human and murine CA forms tested.

FIG. 10 shows the results of thermostability experiments using the DSC for recombinantly expressed c11H9 (FIG. 10A), c12H8 (FIG. 10A), and c2C7 (FIG. 10A), shown in dashed lines in comparison the anti-HER2 therapeutic antibody Cetuximab, in solid line. The thermostability of the c12H8 and c2C7 is similar to that of Cetuximab, whereas c11H9 is slightly less thermostable.

FIG. 11 shows results of Epitope mapping of the hybridoma-derived mAb 11H9 (FIG. 11A), 12H8 (FIG. 11B) and 2C7 (FIG. 11C) using the PepScan technology (pepscan.com). The data indicates that mAb 11H9 binds to peptides presented either as a linear or single loop peptide, whereas mAb 12H8 and 2C7 preferably bind to single loop peptides. Further analysis indicates that mAb 11H9 and 12H8 bind to distinct epitopes in the PG domain, whereas the data for mAb 2C7 implies that it binds to the catalytic domain (inconclusive). FIG. 11D is a schematic summary of the location of the binding epitopes of 11H8, 12H8 and 2C7 based on the results of FIGS. 11 A, B, and C respectively.

FIGS. 12 A, B and C are schematic representations of the principle of the epitope binning assay for hybridoma-derived 11H9, 12H8 and 2C7 mAb by Surface Plasmon Resonance (SPR). FIGS. 12 D and E are a color-coded 'checker board' representation of the results, showing that mAb 11H9, 12H8, and 2C7 do not compete for binding (see legend) when either using the rhCA-IX ECD monomer or dimer.

FIG. 14A is a graph showing that the rhCA-IX ECD (mixture) is catalytically active and can be fully inhibited by 10 µM Acetozolamide. FIG. 14B is a bar graph showing that none of 11H9, 12H8, and 2C7 mAb can inhibit the rhCA-IX ECD enzyme activity; the dotted line indicates 100% CA-IX catalytic activity. Displayed are the average values+SEM of a duplicate experiment.

FIG. 17A shows experiments done at 10 nM while FIG. 17B shows experiments done at 1 and 10 nM. The tested anti-CA-IX mAb cause reduced cell viability similar to the M75 mAb control; the upper dotted line indicates 100% viability in the non-treated cells, whereas the lower dotted line indicates the cell viability in the M75 mAb treated cells. Non-treated (CTL) and secondary Ab-treated (mAb-Zap) cells were used as negative controls. Displayed are the average values+/−SEM of a triplicate experiment.

FIG. 18A shows experiments done using the surrogate ADC assay in which the antibodies are decorated with a secondary antibody that is conjugated to Saporin. Non-treated (CTL) and secondary Ab-treated (mAb-Zap) cells were used as negative controls. FIG. 18B shows the results of experiments done using the recombinantly expressed 'naked' antibodies c2C7, c11H9 and c12H8, which all serve as negative controls, and the mertansine (DM1) conjugated recombinantly expressed c2C7, c11H9 and c12H8 antibodies. The surrogate ADC assay (A) and the ADC assay (B) give very similar $IC_{50}$ results DM1 conjugation renders the c11H9, c12H8 and c2C7 mAb into functional ADC. In both assays the average values+/−SEM of a triplicate experiment are displayed.

FIG. 20 shows results of the evaluation of cross-reactivity of CA-IX antibodies to CA-XII extracellular domain (ECD). SPR measurements using 100 nM of human CA-XII extracellular domain (ECD) showed no binding to c2C7 (FIG. 20 A), c11H9 (FIG. 20 B), or c12H8 (FIG. 20 C) antibodies.

DETAILED DESCRIPTION OF THE INVENTION

Figure 1:
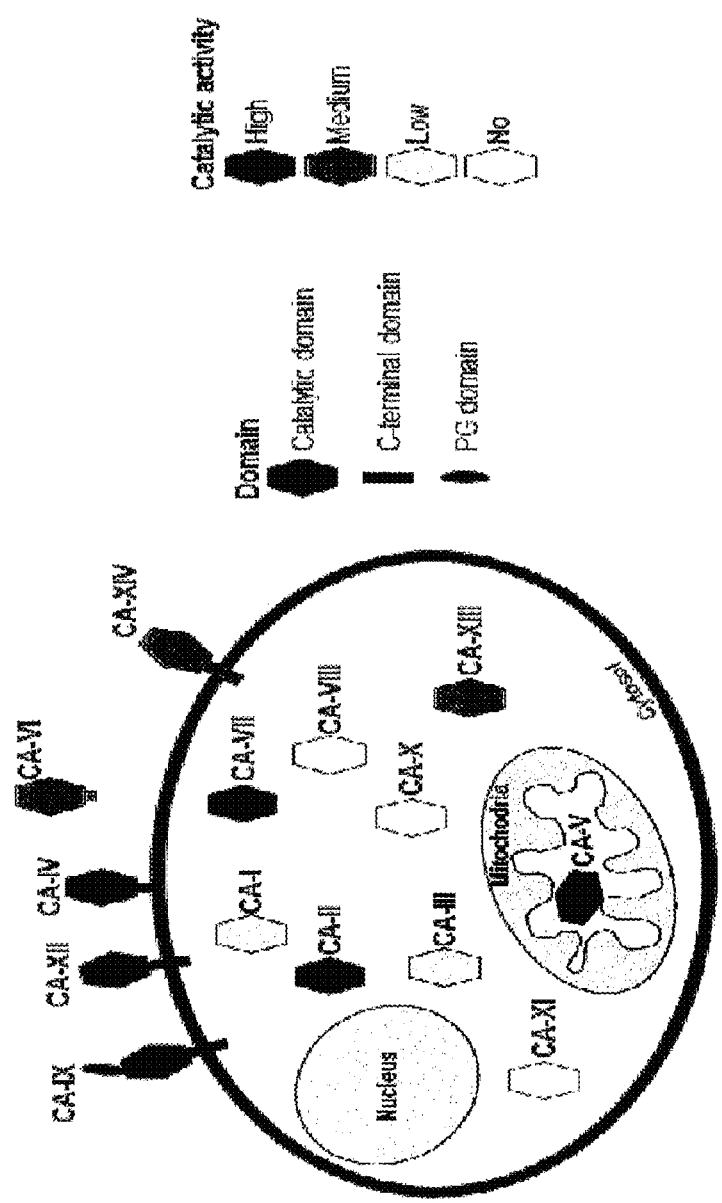
FIG. 1 is a schematic diagram showing the domains, subcellular localization and catalytic activity of the human (h) carbonic anhydrase (CA) family. The cytoplasmic and mitochondrial hCA-I, -II, -III, -VII, -VIII, -X, -XI and -XIII are composed of only a catalytic domain; the secreted hCA-VI has a short C-terminal domain; and the membrane-associated hCA-IV, -VI, -IX, -XII, and -XIV have a transmembrane anchor and, except hCA-IV, also a cytoplasmic tail. hCA-IX is the only member of the CA family with a N-terminal proteoglycan (PG) sequence, which is involved in the cell-cell adhesion process. This figure was adapted from Pastorekova et al., 2004.

The present invention relates to Carbohydrate Anhydrase IX-specific antibodies, fragments thereof, and uses thereof. More specifically, the present invention relates to high-affinity Carbohydrate Anhydrase IX-specific antibodies and fragments thereof and their use as antibody-drug conjugates.

The present invention provides an isolated or purified antibody or fragment thereof, comprising
a) a light chain comprising a complementarity determining region (CDR) L1 sequence selected from the group consisting of:

```
                                    (SEQ ID NO: 1)
    RASGNIHNYLA;

(SEQ ID NO: 7)
    RSSQSLVHSNGNTYLH;
    and (SEQ ID NO: 13)
    KSSQSLLDSDGKTYLN, (SEQ ID NO: 14)
    LVSKLDS,
``` and
a CDR L3 sequence selected from the group consisting of:

```
                                    (SEQ ID NO: 3)
    QHFWNIPFT;

(SEQ ID NO: 9)
    SQNTHVPPT;
    and (SEQ ID NO: 15)
    CQGTHFPW,
``` and
b) a heavy chain comprising a complementarity determining region (CDR) H1 sequence selected from the group consisting of:

```
                                    (SEQ ID NO: 4)
    GFTFTSCYIH;

(SEQ ID NO: 10)
    GFTFNTYAMY;
    and (SEQ ID NO: 16)
    GYTFTNYGMN,
``` a CDR H2 sequence selected from the group consisting of:

```
                                    (SEQ ID NO: 5)
    WIYPGNGNTKYNEIFKG;

(SEQ ID NO: 11)
    RIRSKSNNYAIYYADSVKD;
    and (SEQ ID NO: 17)
    WINTYTGEPTYADDFKG,
``` and
a CDR H3 sequence selected from the group consisting of:

```
                                    (SEQ ID NO: 6)
    GDTTANTMDY;

(SEQ ID NO: 12)
    GWDWFAY;
```

-continued and

GGIATPTSY, (SEQ ID NO: 18)

wherein the antibody or fragment thereof specifically binds the extracellular domain of Carbohydrate Anhydrase IX.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. As these individual schemes define CDR and hypervariable loop regions that are adjacent or overlapping, those of skill in the antibody art often utilize the terms "CDR" and "hypervariable loop" interchangeably, and they may be so used herein. A more recent scheme is the IMGT numbering system (Lefranc et al., 2003), which was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 129) and of the CDR (CDR1: 27 to 38, CDR2: 56 to 65; and CDR3: 105 to 117) is provided.

The CDR/loops are referred to herein according to the Kabat scheme for all CDR. The CDR of the antibodies of the present invention are referred to herein as CDR L1, L2, L3 for CDR in the light chain, and CDR H1, H2, H3 for CDR in the heavy chain.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, and multivalent presentations of any of these. Antibody fragments such as those just described may require linker sequences, disulfide bonds, or other type of covalent bond to link different portions of the fragments; those of skill in the art will be familiar with various approaches.

The antibody or fragment thereof of the present invention specifically binds to the extracellular domain of human (h) Carbonic Anhydrase (CA) IX (Genbank Accession no. NC_000009.12). CA-IX is a metalloenzyme that catalyzes the reversible hydration of carbon dioxide to bicarbonate and protons (FIG. 1). CA-IX is a transmembrane protein with an extracellular catalytic site and an $NH_2$-terminal proteoglycan (PG)-like domain. An antibody and a fragment thereof "specifically binds" CA-IX if it binds CA-IX with an equilibrium dissociation constant ($K_D$, i.e., a ratio of $K_d/K_a$, $K_d$ and $K_a$ are the dissociation rate and the association rate, respectively) less than $10^{-5}$ M (e.g., less than $10^{-6}$ M, $10^{-7}$ M, $10^{-8}$ M, $10^{-9}$ M, $10^{-10}$ M, $10^{-11}$ M, $10^{-12}$ M, or $10^{-13}$M), while not significantly binding other components present in a test sample (e.g., with a $K_D$ that is at least 10 times, such as 50 times or 100 times, more than $K_D$ for binding CA-IX). Affinities of an antibody and a fragment thereof disclosed herein and CA-IX can be readily determined using the method described in Example 5 of the present disclosure.

The antibody or fragment thereof as described herein should exhibit a high degree of internalization. Without wishing to be bound by theory, the antibodies or fragments thereof presently described bind to the extracellular domain of CA-IX. The antibodies or fragments thereof are then internalized by the cell and delivered into subcellular organelles, including endosomes and lysosomes. The antibody or fragment thereof as described herein may also reduce cell viability. Antibody internalization may be measured by any appropriate methods known in the art, including antibody internalization assays offered by Life Technologies, Zap Antibody Internalization Kit by Advanced targeting Systems, and/or quantitative assessment described in Liao-Chan et al., 2015.

The terms "antibody" and "antibody fragment" ("fragment thereof") are as defined above. As previously stated, the antibody or fragment thereof may be from any source, human, mouse, or other; may be any isotype, including IgA, IgD, IgE, IgG, and IgM; and may be any type of fragment, including but not limited to Fv, scFv, Fab, and F(ab')$_2$.

In a more specific embodiment, the present invention provides an isolated or purified antibody or fragment thereof selected from the group consisting of:

a) a light chain comprising CDR L1 of sequence RASGNIH-NYLA (SEQ ID NO:1), CDR L2 of sequence NTITLAD (SEQ ID NO:2), and CDR L3 of sequence QHFWNIPFT (SEQ ID NO:3); and a heavy chain comprising CDR H1 of sequence GFTFTSCYIH (SEQ ID NO:4), CDR H2 of sequence WIYPGNGNTKYNEIFKG (SEQ ID NO:5), and CDR H3 of sequence GDTTANTMDY (SEQ ID NO:6); and wherein the antibody or fragment thereof binds the catalytic domain of CA-IX;

b) a light chain comprising CDR L1 of sequence RSSQS-LVHSNGNTYLH (SEQ ID NO:7), CDR L2 of sequence KVSNRFS (SEQ ID NO:8), CDRL3 of sequence SQNTHVPPT (SEQ ID NO:9); and a heavy chain comprising CDR H1 of sequence GFTFNTYAMY (SEQ ID NO:10), CDR H2 of sequence RIRSKSNNYAIYYADS- VKD (SEQ ID NO:11), and CDR H3 of sequence GWD-WFAY(SEQ ID NO:12); and wherein the antibody or fragment thereof binds the PG-like domain of CA-IX (the epitope may be EEDLPGEE); and c) a light chain comprising CDR L1 of sequence KSSQSLLDSDGKTYLN (SEQ ID NO:13), CDR L2 of sequence LVSKLDS (SEQ ID NO:14), CDRL3 of sequence CQGTHFPW (SEQ ID NO:15); and a heavy chain comprising CDR H1 of sequence GYTFTNYGMN (SEQ ID NO:16), CDR H2 of sequence WINTYT-GEPTYADDFKG (SEQ ID NO:17), and CDR H3 of sequence GGIATPTSY (SEQ ID NO:18); and wherein the antibody or fragment thereof binds the PG-like domain of CA-IX (the epitope may be LPRMQEDSPLGGG).

In one embodiment, the isolated or purified antibody or fragment thereof may comprise a) a variable light (VL) domain of sequence selected from the group consisting of:

```
                                          (SEQ ID NO: 19)
DIQMTQSPASLSASVGETVTITCRASGNIHNYLAWYQQKQGKSPQLLVYN
TITLADGVPSRFSGSGSGTQYSLKINSLQPEDFGSYYCQHFWNIPFTFGA
GTKLELK, (SEQ ID NO: 21)
DVVMTQTPLSLPVSLGDQASISCRSSQSLVHSNGNTYLHWYLQKPGQSPK
WYKVSNRFSGVPDRFSGSGSGTDFTLKISRVEAEDLGVYFCSQNTHVPPT
FGGGTKLEIK,
and (SEQ ID NO: 23)
DVVMTQTPLTLSVTIGQPASISCKSSQSLLDSDGKTYLNWLLQRPGQSPK
RLIYLVSKLDSGVPDRFTGSGSGTDFTLKISRVEAEDLGVYYCCQGTHFP
WTFGGGTKLEIK;
``` b) a variable heavy (V$_H$) domain of sequence selected from the group consisting of:

```
                                          (SEQ ID NO: 20)
QVQLQQSGPELVKPGASVRISCKASGFTFTSCYIHWMKQRPGQGLEWIGW
IYPGNGNTKYNEIFKGRATLTTDKSSSTAYMQLSSLTSEDSAVYFCARGD
TTANTMDYWGQGTSVTVSS;

(SEQ ID NO: 22)
EVQLVESGGRLVQPKGSLKLSCAASGFTFNTYAMYWIRQAPGKGLEWVAR
IRSKSNNYAIYYADSVKDRFTISRDDSQSMLYLQMNNLKTEDTAMYYCVR
GWDWFAYWGQGTPVTVSA;
and (SEQ ID NO: 24)
QIQLVQSGPELKKPGETVKISCKASGYTFTNYGMNWVQQAPGKGLKWMGW
INTYTGEPTYADDFKGRFAFSLETSASTAYLQINNLKNEDMATYFCARGG
IATPTSYWGQGTTLTVSS;
``` or c) a sequence substantially identical to the variable light (VL) domain of a) or the variable heavy (VH) domain of b) as described above.

The antibody or fragment thereof just defined specifically binds to the extracellular domain of CA-IX.

In specific, non-limiting examples, the isolated or purified antibody or fragment thereof of the present invention may comprise a) a variable light (V$_L$) domain of sequence

```
                                          (SEQ ID NO: 19)
DIQMTQSPASLSASVGETVTITCRASGNIHNYLAWYQQKQGKSPQLLVYN
TITLADGVPSRFSGSGSGTQYSLKINSLQPEDFGSYYCQHFWNIPFTFGA
GTKLELK
``` and/or variable heavy (V$_H$) domain of sequence

```
                                          (SEQ ID NO: 20)
QVQLQQSGPELVKPGASVRISCKASGFTFTSCYIHWMKQRPGQGLEWIGW
IYPGNGNTKYNEIFKGRATLTTDKSSSTAYMQLSSLTSEDSAVYFCARGD
TTANTMDYWGQGTSVTVSS;
``` b) a variable light (V$_L$) domain of sequence

```
                                          (SEQ ID NO: 21)
DVVMTQTPLSLPVSLGDQASISCRSSQSLVHSNGNTYLHWYLQKPGQSPK
WYKVSNRFSGVPDRFSGSGSGTDFTLKISRVEAEDLGVYFCSQNTHVPPT
FGGGTKLEIK
``` and/or variable heavy (V$_H$) domain of sequence

```
                                          (SEQ ID NO: 22)
EVQLVESGGRLVQPKGSLKLSCAASGFTFNTYAMYWIRQAPGKGLEWVAR
IRSKSNNYAIYYADSVKDRFTISRDDSQSMLYLQMNNLKTEDTAMYYCVR
GWDWFAYWGQGTPVTVSA;
``` c) a variable light (V$_L$) domain of sequence

```
                                          (SEQ ID NO: 23)
DVVMTQTPLTLSVTIGQPASISCKSSQSLLDSDGKTYLNWLLQRPGQSPK
RLIYLVSKLDSGVPDRFTGSGSGTDFTLKISRVEAEDLGVYYCCQGTHFP
WTFGGGTKLEIK
``` and/or variable heavy (V$_H$) domain of sequence

```
                                          (SEQ ID NO: 24)
QIQLVQSGPELKKPGETVKISCKASGYTFTNYGMNWVQQAPGKGLKWMGW
INTYTGEPTYADDFKGRFAFSLETSASTAYLQINNLKNEDMATYFCARGG
IATPTSYWGQGTTLTVSS;
``` or a sequence substantially identical thereto.

In a yet more specific example, the isolated or purified antibody specific for CA-IX may comprise:

a) a variable light (V$_L$) domain comprising the sequence

```
                                          (SEQ ID NO: 25)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
``` and variable heavy (V$_H$) domain comprising the sequence

```
                                          (SEQ ID NO: 26)
QVQLQQSGPELVKPGASVRISCKASGFTFTSCYIHWMKQRPGQGLEWIGW

IYPGNGNTKYNEIFKGRATLTTDKSSSTAYMQLSSLTSEDSAVYFCARGD

TTANTMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG;
``` b) a variable light (V$_L$) domain comprising the sequence (SEQ ID NO: 27)
DVVMTQTPLSLPVSLGDQASISCRSSQSLVHSNGNTYLHWYLQKPGQSPK

WYKVSNRFSGVPDRFSGSGSGTDFTLKISRVEAEDLGVYFCSQNTHVPPT

FGGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC and variable heavy (V$_H$) domain comprising the sequence (SEQ ID NO: 28)
EVQLVESGGRLVQPKGSLKLSCAASGFTFNTYAMYWIRQAPGKGLEWVARI

RSKSNNYAIYYADSVKDRFTISRDDSQSMLYLQMNNLKTEDTAMYYCVRGW

DWFAYWGQGTPVTVSAASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLY

SKLTVDKSRWQQGNVFSCSVMHEALHNHYTQKSLSLSPG;

c) a variable light (V$_L$) domain comprising the sequence (SEQ ID NO: 29)
DVVMTQTPLTLSVTIGQPASISCKSSQSLLDSDGKTYLNWLLQRPGQSPKR

LIYLVSKLDSGVPDRFTGSGSGTDFTLKISRVEAEDLGVYYCCQGTHFPVV

TFGGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEVTH

QGLSSPVTKSFNRGEC and variable heavy (V$_H$) domain comprising the sequence (SEQ ID NO: 30)
QIQLVQSGPELKKPGETVKISCKASGYTFTNYGMNWVQQAPGKGLKWMGWI

NTYTGEPTYADDFKGRFAFSLETSASTAYLQINNLKNEDMATYFCARGGIA

TPTSYWGQGTTLTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLY

SKLTVDKSRWQQGNVFSCSVMHEALHNHYTQKSLSLSPG;

or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the antibody or fragment thereof while maintaining the CDR sequences listed above and the overall structure of the antibody or fragment; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage there between, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence at least 95%, 98% or 99% identical to that of the antibodies described herein.

The present invention further encompasses an antibody or fragment thereof that is chimeric (or chimerized), veneered, or humanized. The antibody or fragment thereof may be chimeric, in that the antibody or fragment thereof is a combination of protein sequences originating from more than one species. As is known to those of skill in the art, a chimeric antibody is produced by combining genetic material from a nonhuman source (for example but not limited to a mouse) with genetic material from a human. For example and without wishing to be limiting, human constant domains can be fused to mouse $V_H$ and $V_L$ sequences (see Gonzales et al 2005). Veneering, also referred to in the art as "variable region resurfacing", of antibodies involves replacing solvent-exposed residues in the framework region of the native antibody or fragment thereof with the amino acid residues in their human counterpart (Padlan, 1991; Gonzales et al 2005); thus, buried non-humanized residues, which may be important for CDR conformation, are preserved while the potential for immunological reaction against solvent-exposed regions is minimized. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In this process, one or more than one of the CDR defined herein may be fused or grafted to a human variable region ($V_H$, or $V_L$), to other human antibody (IgA, IgD, IgE, IgG, and IgM), to human antibody fragment framework regions (Fv, scFv, Fab), or to human proteins of similar size and nature onto which CDR can be grafted (Nicaise et al, 2004). In such a case, the conformation of said one or more than one hypervariable loop is likely preserved, and the affinity and specificity of the sdAb for its target (i.e., Axl) is likely minimally affected. As is known by those of skill in the art, it may be necessary to incorporate certain native amino acid residues into the human framework in order to retain binding and specificity. Humanization by CDR grafting is known in the art (for example, see Tsurushita et al, 2005; Jones et al, 1986; Tempest et al, 1991; Riechmann et al, 1988; Queen et al, 1989; reviewed in Gonzales et al, 2005—see also references cited therein), and thus persons of skill would be amply familiar with methods of preparing such humanized antibody or fragments thereof.

The present invention thus provides an isolated or purified antibody or fragment thereof specific for CA-IX may be a chimeric antibody comprising the variable domain as defined above linked to human IgG1 constant domains. For example, and without wishing to be limiting in any manner, the human IgG1 constant domains may comprise a human kappa 1 light chain constant domain and human IgG1 heavy chain constant domains.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, $His_5$, $His_6$, or $His_8G$), or a combination thereof. In another example, the signal peptide may be MVLQTQVFISLLLWISGAYG (SEQ ID NO:31) or MDWTWRILFLVAAATGTHA (SEQ ID NO:32). In a further example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or fragment thereof of the present invention may also be in a multivalent display format, also referred to herein as multivalent presentation. Multimerization may be achieved by any suitable method known in the art. For example, and without wishing to be limiting in any manner, multimerization may be achieved using self-assembly molecules such as those described in Zhang et al (2004a; 2004b) and WO2003/046560. The described method produces pentabodies by expressing a fusion protein comprising the antibody or fragment thereof of the present invention and the pentamerization domain of the B-subunit of an $AB_5$ toxin family (Merritt & Hol, 1995); the pentamerization domain assembles into a pentamer. A multimer may also be formed using the multimerization domains described by Zhu et al. (2010); this form, referred to herein as a "combody" form, is a fusion of the antibody or fragment of the present invention with a coiled-coil peptide resulting in a multimeric molecule (Zhu et al., 2010). Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996).

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody. For example, and without wishing to be limiting in any manner, the antibody or fragments thereof may be presented in a bi-specific antibody.

The invention also encompasses the antibody or fragment thereof as described above linked to a cargo molecule. The cargo molecule may be any suitable molecule. For example, and without wishing to be limiting in any manner, the cargo molecule may be a detectable agent, a therapeutic agent, a drug, a peptide, an enzyme, a growth factor, a cytokine, a receptor trap, an antibody or fragment thereof (e.g., IgG, scFv, Fab, $V_HH$, $V_H$, $V_L$, etc) a chemical compound, a carbohydrate moiety, DNA-based molecules (anti-sense oligonucleotide, microRNA, siRNA, plasmid), a cytotoxic agent, viral vector (adeno-, lenti-, retro-), one or more liposomes or nanocarriers loaded with any of the previously recited types of cargo molecules, or one or more nanoparticle, nanowire, nanotube, or quantum dots. The antibody or fragment thereof may be linked to the cargo molecule using any method known in the art (recombinant technology, chemical conjugation, etc.).

In one non-limiting example, the cargo molecule may be a detectable label, a radioisotope, a paramagnetic label such as gadolinium or iron oxide, a fluorophore, a fluorescent agent, Near Infra-Red (NIR) fluorochrome or dye such as Cy5.5, an echogenic microbubble, an affinity label (for example biotin, avidin, etc), a detectable protein-based molecule, nucleotide, quantum dot, nanoparticle, nanowire, or nanotube or any other suitable agent that may be detected by imaging methods. In a specific, non-limiting example, the anti-CA-IX or fragment thereof may be linked to a near infrared fluorescence (NIRF) imaging dye, for example and not wishing to be limiting Cy5.5, Alexa680, Dylight680, or Dylight800.

In another specific, non-limiting embodiment, the antibody or fragment thereof as described herein is linked to a drug, thus providing an antibody-drug conjugate (ADC). The drug may be any type of drug, for example but not limited to a cytotoxic agent. The cytotoxic agent may include, but is not limited to anti-microtubule agents (such as taxanes, maytansines and auristatins), DNA damaging agents (such as calicheamicin and duocarmydin), RNA polymerase inhibitors (such as alpha-amantin), and other potent cytotoxic drugs (such as anthracyclines). As is known to those of skill in the art, the antibody-drug conjugate allows for targeted delivery of a drug, thus limiting systemic exposure. In this construct, the antibody or fragment thereof as described herein binds to the extracellular domain of CA-IX; the drug linked to the antibody or fragment thereof is thus internalized. Upon internalization the cytotoxic agent is released within the target cells upon degradation of the human CA-IX antibody-DM1 complex in lysosomes. Depending on the intracellular concentration of the cytotoxic agent accumulated in cancer cells, rapid apoptosis occurs.

The cargo molecule as described herein may be linked, also referred to herein as "conjugated", to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. When conjugating the cargo molecule to the antibody or fragment thereof, a suitable linker may be used. Methods for linking an antibody or fragment thereof to a cargo molecule such as a therapeutic or detectable agent would be well-known to a person of skill in the art.

The present invention also encompasses nucleic acid sequences encoding the molecules as described herein. Given the degeneracy of the genetic code, a number of nucleotide sequences would have the effect of encoding the desired polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces. A purified antibody or fragment thereof immobilized onto a surface may be used in a variety of methods, including diagnostic methods.

Thus, the present invention further provides an in vitro method of detecting CA-IX, comprising contacting a tissue sample with one or more than one isolated or purified antibody or fragment thereof of the present invention linked to a detectable agent. The CA-IX-antibody complex can then be detected using detection and/or imaging technologies known in the art. The tissue sample in the method as just described may be any suitable tissue sample, for example but not limited to a serum sample, a vascular tissue sample, or a tumour tissue sample; the tissue sample may be from a human or animal subject. The step of contacting is done under suitable conditions, known to those skilled in the art, for formation of a complex between the antibody or fragment thereof and CA-IX. The step of detecting may be accomplished by any suitable method known in the art, for example, but not limited to optical imaging, immunohistochemistry, molecular diagnostic imaging, ELISA, or other suitable method. For example, and without wishing to be limiting in any manner, the isolated or purified antibody or fragment thereof linked to a detectable agent may be used in immunoassays (IA) including, but not limited to enzyme IA (EIA), ELISA, "rapid antigen capture", "rapid chromatographic IA", and "rapid EIA". (For example, see Planche et al, 2008; Sloan et al, 2008; Rüssmann et al, 2007; Musher et al, 2007; Turgeon et al, 2003; Fenner et al, 2008). In a specific, non-limiting embodiment, the in vitro method is for detection of CA-IX in circulating cells and the tissue sample is a serum sample.

The present invention also provides an in vivo method of detecting CA-IX expression in a subject. The method comprises administering one or more than one isolated or purified antibody or fragment thereof as described herein linked to a detectable agent to the subject, then detecting the labelled antibody or fragment thereof bound to CA-IX. The step of detecting may comprise any suitable method known in the art, for example, but not limited to PET, SPECT, or fluorescence imaging, or any other suitable method. The method as just described may be useful in detecting the expression of CA-IX in tissues, for example but not limited to tumor tissues.

The in vivo detection step in the methods described above may be whole body imaging for diagnostic purposes or local imaging at specific sites, such as but not limited to sites of solid tumor growth, in a quantitative manner to assess the progression of disease or host response to a treatment regimen. The detection step in the methods as described above may be immunohistochemistry, or a non-invasive (molecular) diagnostic imaging technology including, but not limited to:

Optical imaging;
Positron emission tomography (PET), wherein the detectable agent is an isotope such as $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized;
Single photon emission computed tomography (SPECT), wherein the detectable agent is a radiotracer such as $^{99m}$Tc, $^{111}$In, $^{123}$I, $^{201}$Tl, $^{133}$Xe, depending on the specific application;
Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques.
Contrast-Enhanced Ultrasonography (CEUS) or ultrasound, wherein the detectable agent is at least one acoustically active and gas-filled microbubble. Ultrasound is a widespread technology for the screening and early detection of human diseases. It is less expensive than MRI or scintigraphy and safer than molecular imaging modalities such as radionuclide imaging because it does not involve radiation.

The present invention further provides a method of transporting a molecule of interest into cells expressing CA-IX. The method comprises administering the molecule linked to an antibody or fragment thereof as described herein to a subject. The molecule may be any desired molecule, including the cargo molecules, as previously described; the molecule may be "linked" to the antibody or fragment thereof using any suitable method, including, but not limited to conjugation or expression as a fusion protein. The administration may be by any suitable method, for example parenteral administration, including but not limited to intravenous (iv), subcutaneous (sc), and intramuscular (im) administration. In this method, the antibody or fragment thereof of the present invention delivers the desired molecule to cells in a targeted fashion.

The present invention also encompasses a composition comprising one or more than one isolated or purified antibody or fragment thereof as described herein. The composition may comprise a single antibody or fragment as described above, or may be a mixture of antibodies or fragments. Furthermore, in a composition comprising a mixture of antibodies or fragments of the present invention, the antibodies may have the same specificity, or may differ in their specificities; for example, and without wishing to be limiting in any manner, the composition may comprise antibodies or fragments thereof specific to CA-IX (same or different epitope). The composition may also comprise one or more than one antibody or fragments of the present invention linked to one or more than one cargo molecule. For example, and without wishing to be limiting in any manner, the composition may comprise one or more than one ADC in accordance with the present invention.

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The present invention will be further illustrated in the following examples. However, it is to be understood that these examples are for illustrative purposes only and should not be used to limit the scope of the present invention in any manner.

Example 1: Production and Purification of rhCA-IX ECD

A 416 amino acid long recombinant fragment of the extracellular domain of human (h) CA-IX with a C-terminal His-tag was prepared. The sequence of the recombinant fragment is shown in SEQ ID NO:33.

Construct.

Figure 2:
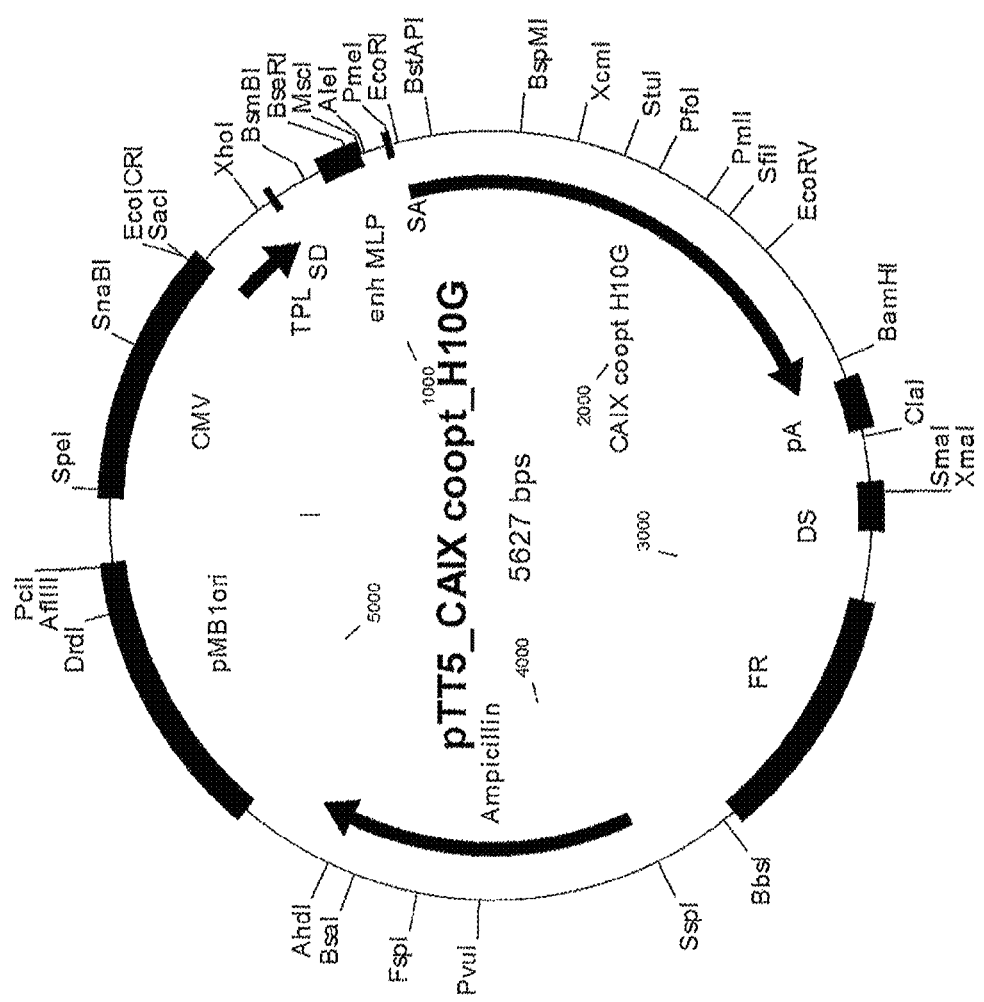
FIG. 2 is a schematic diagram of the construct containing the synthetic hCA-IX ECD with an N-terminal His-tag.

A PTT5 construct containing a synthetic recombinant fragment of the extracellular domain (ECD) of hCA-IX linked to a C-terminal His-tag was synthesized by GeneART. A schematic of the plasmid construct is shown in FIG. 2.

Transient Transfection.

2 and 50 mL transfections of the plasmid DNA into CHO cells were prepared. The day before the transfection, CHO-3E7 cells were diluted to $0.7 \times 10^6$ cells/ml in complete growth medium (FreeStyle™ F17 media (Invitrogen) supplemented with L-glutamine (Hyclone) 4 mM final and Kolliphor® P188 0.1% final) and grown in shaker flasks (agitation rate of 100 rpm) at 37° C., 5% $CO_2$ in a humidified incubator. At the time of transfection, the cell density was between $1.7 \times 10^6$ and $2.2 \times 10^6$ cells/mL and viability was greater than 97%. The requisite number of cells was transferred to a sterile flask and antibiotics/antimycotics 100× solution (Hyclone #SV30079) were added. For each transfection, a 2.0 ml cell suspension was transferred to a 6-well plate. The DNA-PEI mixture was prepared by a multi-step process that is outlined briefly: a master mix of AKTdd pTT22 (constitutively active mutant of AKT) and ssDNA (0.33 μg AKTdd pTT22+0.77 μg ssDNA/2 ml transfection) in complete cell culture media was prepared and added to labelled 1.5 ml tubes. Appropriate quantities of plasmid DNA (pTT5_CAIX coopt_H10G) were added to each tube such that the final volume, including the master mix, is 100 μl. Finally, 20 μl of PEI Pro™ (polyethtleneimine from Polyplus-transfection #115-375), diluted to 0.055 mg/ml was added to the tubes containing DNA. The DNA mixture was vortexed and allowed to incubate for 3-10 minutes, after which the DNA-PEI mixture was added to the cells in the six-well plates. The contents of the plates were mixed with gentle swirling and incubated at 37° C., 5% $CO_2$ humidified incubator. 55 μl of 40% Tryptone N1 (Organotechnie) 1% final and 5.5 μl of VPA (Valproic acid sodium salt from Sigma) 0.5 mM final was added 4-24 h post-transfection and the cells were incubated for another 6 days at 32° C. The same protocol was followed for 50 ml transfections, except that all quantities were increased proportionately and transfections were carried out in a 250 ml shake flasks.

Harvest.

For 2 ml transfections, the transfected cell population was transferred to a 1.5 ml tube. The cells were removed by centrifugation at 1500 g for 10 minutes and the supernatant was transferred to a new tube. For 50 ml transfections, the transfected cell population was transferred to a 50 ml tube and the cells were removed by centrifugation at 250 g for 10 minutes. The supernatant was filtered using a Millipore steriflip unit (Millipore).

Purification.

The filtered culture supernatant was passed through a 1 ml protein A MabSelect SuRe resin (GE Healthcare) column. Five (5) bed volumes PBS D-PBS pH 7.4 w/o Ca, w/o Mg (Hyclone) were added to remove unbound material. The protein was eluted with 1 ml of 100 mM Na Citrate pH 3.0 and the eluate was neutralized with 1 M Tris, pH 9. Buffer exchange into PBS was carried out using dilution and filtration using Ultracel 10K centrifuge filters.

Figure 3:
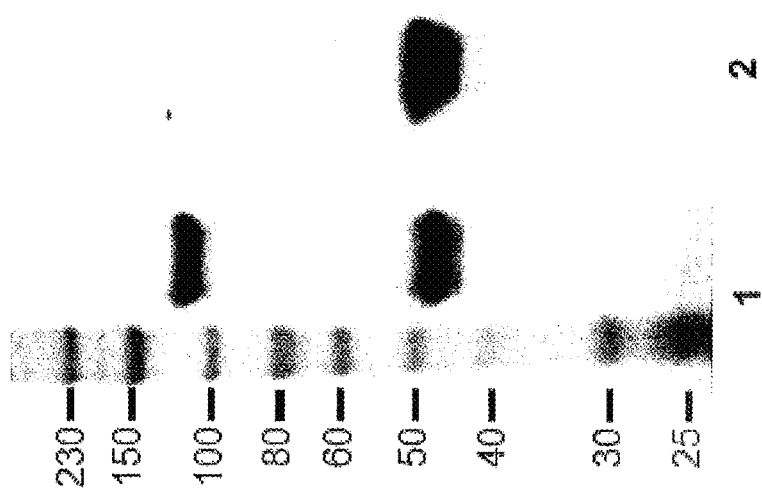
FIG. 3 shows a Coomassie Brilliant Blue stained SDS-PAGE of the NRC-produced rhCA-IX extracellular domain (ECD) under reducing (lane 2) and non-reducing (lane 1) conditions. The disulphide-bonded dimer rhCA-IX dimer has a molecular weight of ~110 kDa, whereas the monomer and the reduced dimer are ~48 kDa.

The rhCA-IX ECD was expressed in CHO cells, purified by Ni-agarose and verified by Sodium Dodecyl Sulfate PolyAcrylamide Gel Electrophoresis (SDS-PAGE) under non-reducing and reducing conditions (FIG. 3). The protein was shown to be a 50/50 mixture of rhCA-IX ECD monomer (~48 kDa) and dimer (~110 kDa).

Figure 4A:
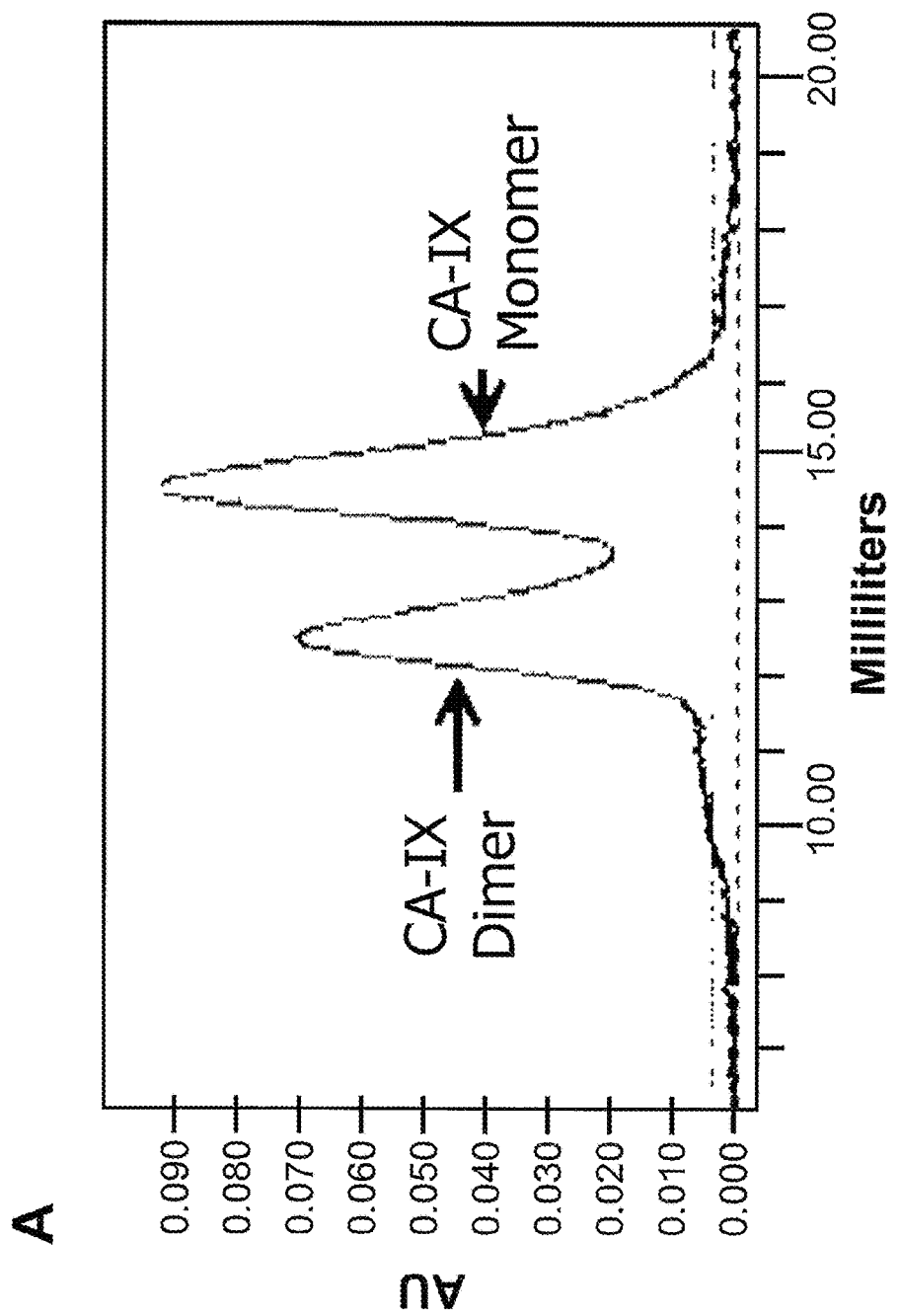
FIG. 4A is the SEC profiles of the hCA-IX ECD produced in CHO cells, showing the presence of monomers and dimers. Monomer and dimer containing fractions were re-evaluated by SEC after storage for 2 weeks at 4° C.
Figure 4B:
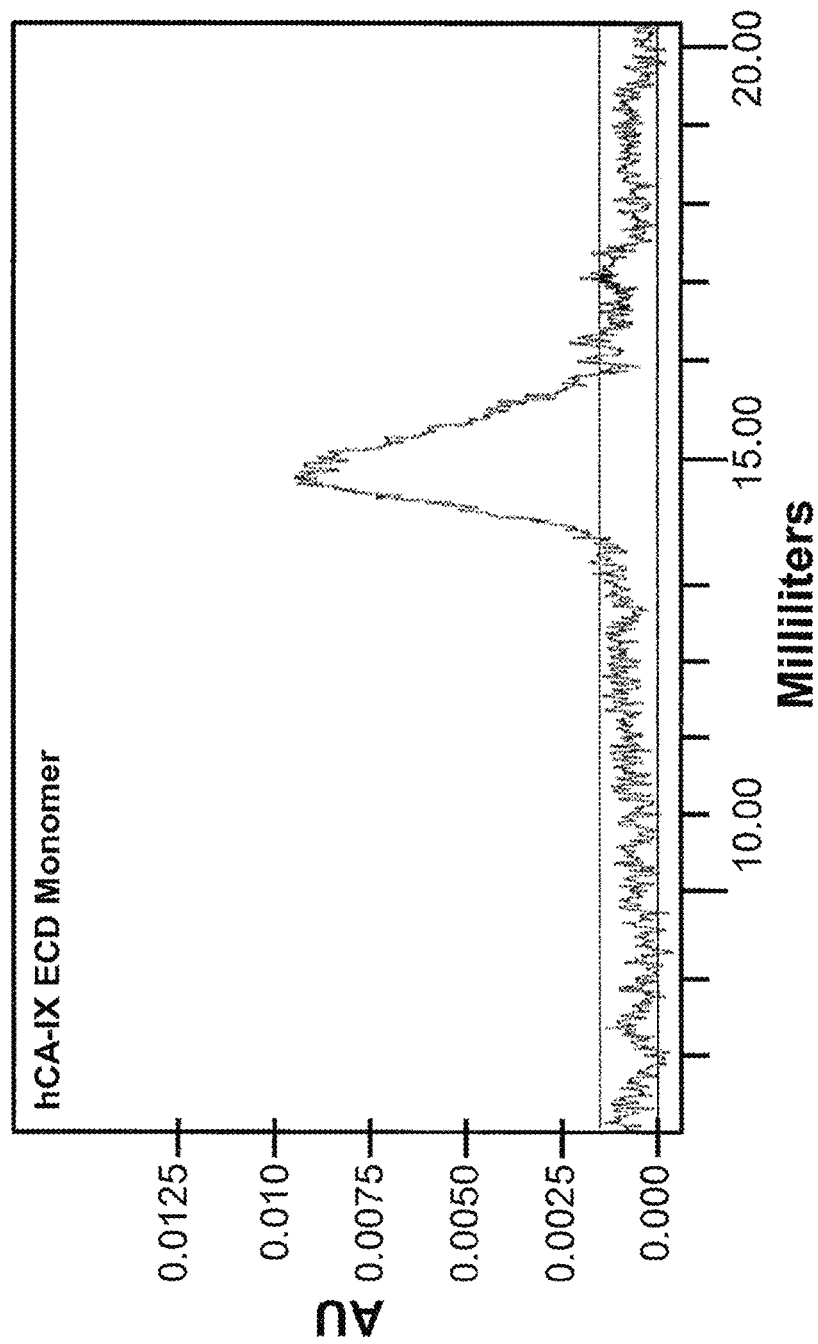
(FIGS. 4B and 4C, respectively).
Figure 4C:
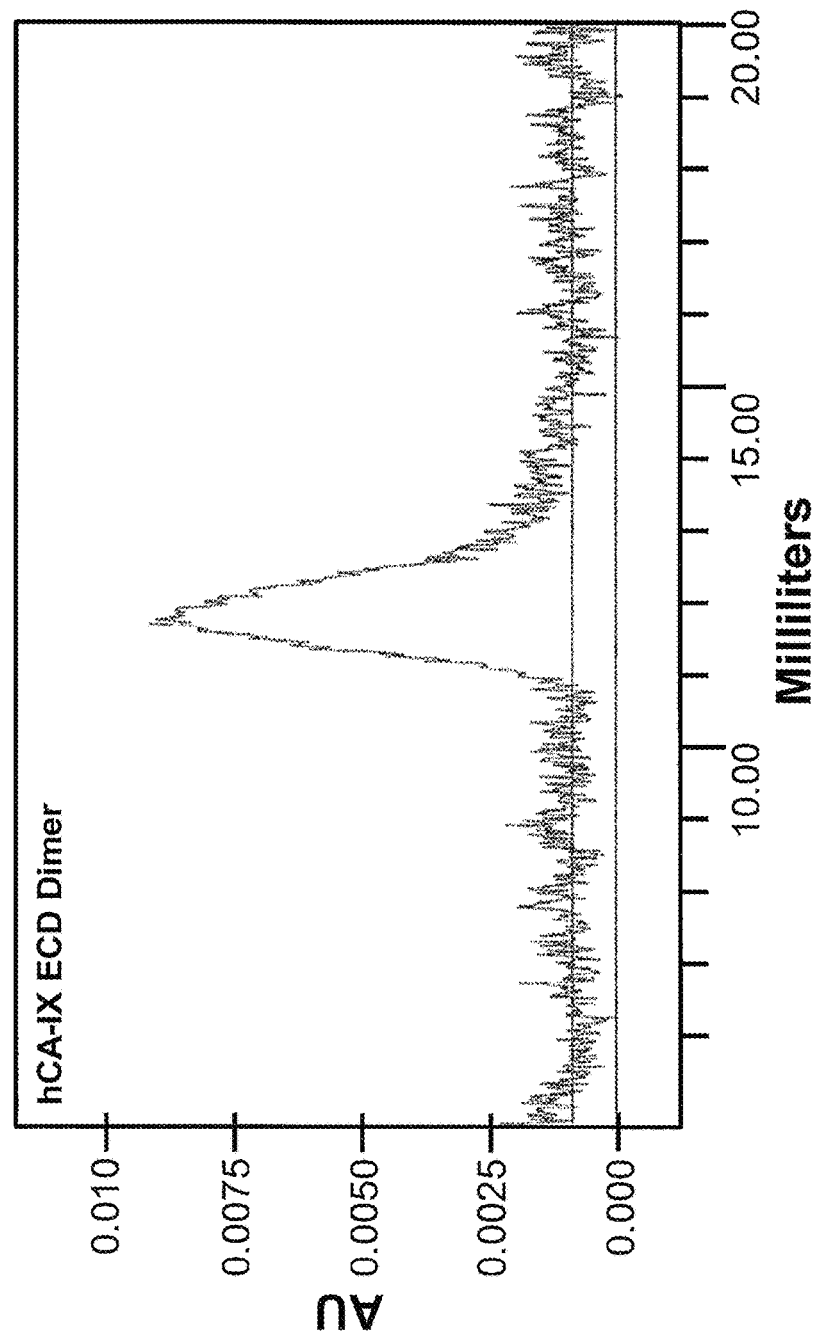
Figure 4D:
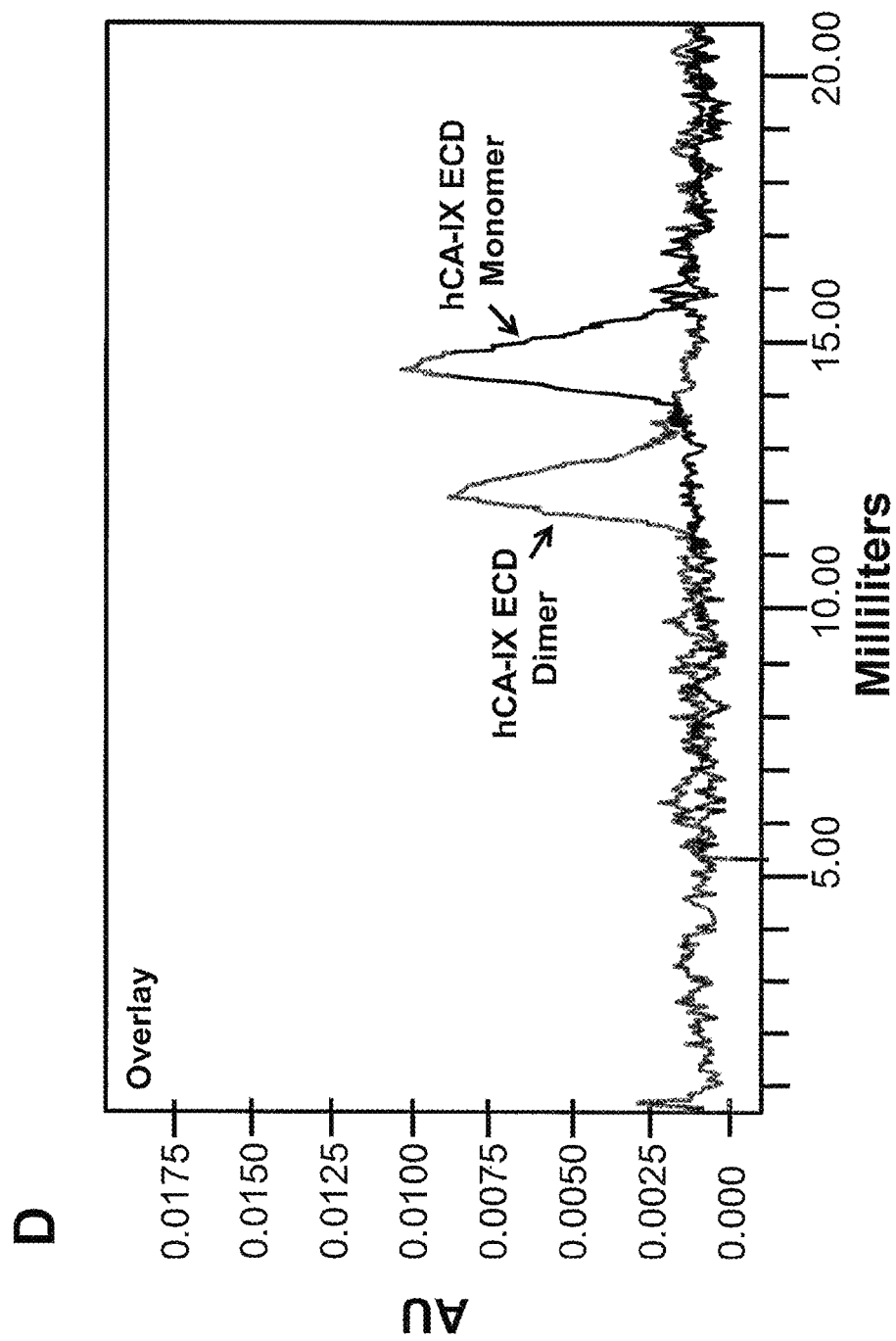
FIG. 4D shows an overlay of FIG. 4B and FIG. 4C.

The rhCA-IX ECD monomer/dimer was further purified by size exclusion chromatography (SEC) of the protein mixture (FIG. 4A). Fractions with the highest protein concentration were selected and kept at 4° C. for several weeks. Prior to further biophysical characterization measurements, samples were reanalyzed by SEC (FIGS. 4B-D). The results of this evaluation showed that both the monomer and dimer are stable upon storage.

Example 2: Generation of Anti-CA-IX Antibodies

To produce antibodies that target the extracellular domain of hCA-IX, mice were immunized with the rhCA-IX ECD obtained in Example 1. Hybridomas were generated and conditioned medium was evaluated for mAb binding to the rhCA-IX ECD protein.

Immunizations.

6-week old A/J mice were bled (pre-immune serum) and immunized i.p. and s.c. with 33 µg of rhCA-IX monomer/dimer mixture in incomplete Freund adjuvant, as part of a 3-protein multiplexed immunization mixture. Three weeks later, a second injection of 33 µg of rhCA-IX protein in PBS was done and mice were bled 7-10 days later. The serum titer was measured by ELISA. Three to eight months later, a final i.p. booster injection using 33 µg of rhCA-IX protein in PBS was done 4 days prior to fusion experiment.

Fusion of the Harvested Spleen Cells.

All manipulations were done under sterile conditions. Spleen cells were harvested from immunized mice in IMDM (Hy-Clone) and fused to NS0 myeloma cell line using PEG fusion protocol. To this end, spleen cells and myeloma cells were washed in IMDM, counted in RBC lysing buffer (Sigma) and mixed together at a 5:1 ratio. Pelleted cells were fused together by adding 1 ml of a 50% solution of PEG 4000 (EMD-Millipore) in PBS preheated at 37° C. drop-wise over one minute, and incubated at 37° C. for an additional 90 sec. The reaction was stopped by addition of 30 ml of IMDM at 22° C. over 2 min. After a 10 min incubation, freshly fused cells were spun at 233×g for 10 min. Cells were washed once in IMDM supplemented with 10% heat inactivated FBS (Sigma), and suspended at a concentration of $2\times10^5$ input myeloma cells per ml in HAT selection medium (IMDM containing 20% heat inactivated FBS, penicillin-streptomycin (Sigma), 1 ng/ml mouse IL-6 (Biosource), HAT media supplement (Sigma) and L-glutamine) and incubated at 37° C., 5% $CO_2$. The next day, hybridoma cells were washed and suspended at a concentration of $2\times10^5$ input myeloma cells per ml in semi-solid medium D (StemCell) supplemented with 5% heat inactivated FBS, 1 ng/ml mouse IL-6 and 10 µg/ml FITC-Fab'2 Goat anti-mouse IgG (H+L) (Jackson). The cell mixture was plated in Petri dish (Genetix) and further incubated for 6-7 days at 37° C., 5% $CO_2$. Secretor clones were then transferred using a mammalian cell clone picker (ClonepixFL, Molecular Devices) into sterile 96-well plates (Costar) containing 200 µl of IMDM supplemented with 20% heat inactivated FBS, penicillin-streptomycin (Sigma), 1 ng/ml mouse IL-6 (Biosource), HT media supplement (Sigma) and L-glutamine and incubated for 2-3 days at 37° C., 5% $CO_2$.

Hybridoma selection. Hybridoma supernatant were screened by ELISA to detect specific Binders.

To this end, 96-well half-area plates (Costar) were coated with 25 µl of CA-IX at 5 µg/ml in PBS and incubated overnight at 4° C. Microplates were washed 3 times with PBS, blocked with PBS-BSA 1%, and 25 µl of hybridoma supernatant were added and incubated at 37° C., 5% $CO_2$ for 2 hours. Plates were washed 4 times with PBS-Tween 20 0.05% and incubated for 1 h at 37° C., 5% $CO_2$ with 25 µl of secondary antibody alkaline phosphatase conjugated F(ab)'$_2$ goat anti-mouse IgG (H+L) (Jackson Immunoresearch) diluted 1/3000 in blocking buffer. After 4 washes with PBS-Tween 20 0.05%, 25 µl of a 1 mg/ml pNPP substrate solution was added and further incubated for one hour at 37° C. $OD_{405}$ nm measurements were taken using a microplate reader (Spectramax 340 PC, Molecular Devices).

From 2 fusions of mouse spleen cells, 51 CA-IX mAb producing hybridomas were identified from which conditioned medium (CM) was collected and evaluated for binding to the rhCA-IX ECD protein by ELISA. Results for the selected clones are shown in Table 1.

TABLE 1

Evaluation of the CM collected from mAb-producing hybridomas by ELISA (rhCA-IX ECD).

| Fusion | Clone | Species | Isotype | ELISA on protein |
|---|---|---|---|---|
| F101 | 11H9 | mouse | IgG2A, κ | +++ |
| F101 | 12H8 | mouse | IgG1, κ | +++ |
| F117 | 2C7 | mouse | IgG1, κ | +++ |

All mAb were then purified via Protein A spin column, dialyzed twice against PBS and concentrated using an Amicon filter (cut-off MW 30,000). The final concentration of the antibody solutions was determined by absorbance (280 nm). Results for clones 11H9, 12H8 and 2C7 are shown in Table 2.

TABLE 2

Hybridoma mAb concentration by nanodrop after Protein A purification.

| Fusion | Clone | volume (uL) | Concentration (µg/uL) | Produced (µg/15 mL) |
|---|---|---|---|---|
| F101 | 11H9 | 350 | 0.14 | 49 |
| F101 | 12H8 | 170 | 0.2 | 34 |
| F117 | 2C7 | 200 | 1.99 | 398 |

Example 3: Characterization of Anti-CA-IX mAb

The anti-CA-IX monoclonal antibodies obtained in Example 2 were characterized using Western blot and Reverse Phase Protein Array (RPPA).

Figure 5:
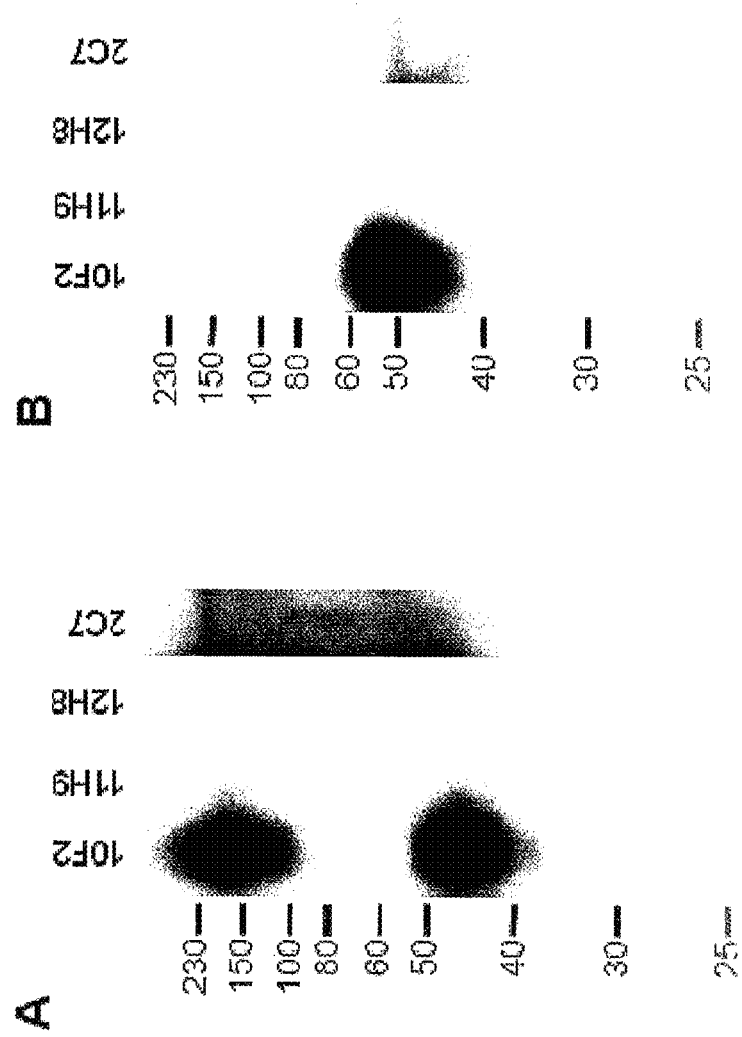
FIG. 5 shows Western blots of non-purified hybridoma derived CA-IX mAbs (undiluted CM), evaluated for binding to the purified CA-IX ECD antigen. mAb 11H9, 12H8 and 2C7 failed to bind to rhCA-IX ECD under both non-reducing (FIG. 5A) and reducing conditions (FIG. 5B). Anti-hCA-IX mAb 10F2 is shown as a positive control.

Western Blot 1.6 µg of purified rhCA-IX ECD (as was used for the immunization) was resolved by SDS-PAGE (10%) under reducing conditions. Nitrocellulose membranes were prepared and probed with the individual CA-IX Abs either non-purified CM (200 µL) or purified at a concentration of 5 µg/mL. Immunoreactive bands were visualized by chemiluminescence (Perkin-Elmer). The analysis of the non-purified mAb 11H9, 12H8 or 2C7 indicated that these mAb did not detect rhCA-IX ECD under either one of these conditions (FIG. 5), however after purification the 12H8 mAb was able to detect the rhCA-IX under both reducing and non-reducing conditions.

Reverse Phase Protein Array (RPPA).

Proteins were spotted in duplicate using a Genetix QArray2 contact printer with SMP3 split pins (ArrayIt) on 16 pads nitrocellulose slides (Whatman FAST) using a two pins configuration to print two identical proteins simultaneously. Each of the 16 pads was printed with an identical array of 182 spots (13×14) of both native and denatured in the same array, but using distinct printing parameters on the robot. Printing was done at 20° C. and 60% constant humidity. The source plate containing native proteins was kept at about 12° C. on the robot's chilling device and the plate with denatured proteins was kept at 22° C. during printing to avoid any SDS precipitation. Once printed, the slides were stored for one hour at room temperature in a desiccator at 5 to 10% humidity, to dry the spotted proteins.

Each array was simultaneously probed with a hybridoma supernatant (secreted mAb, Example 2) and an anti-GFP antibody to normalize for the spotted protein volume. Slides were assembled in the 16-well incubation chambers (Whatman) and in the multi-slide frame (Whatman) that is a reusable holder for up to four slides. In this assembly, a liquid-tight well was created on top of each individual array pad. To block nonspecific binding, 100 µl of blocking solution (1×PBS/3% BSA/0.1% Tween20) was added to each well. Each chamber was sealed with aluminum tape to prevent evaporation and incubated (1 h, RT) with gentle agitation. The nitrocellulose pads were never allowed to dry from this step on. mAb were prepared by mixing 30 µl of each crude hybridoma supernatant with 30 µl of incubation solution (1×PBS/2% BSA/0.05% Tween20/Rabbit anti-GFP-AlexaFluor555 (0.9 µg/ml)). Blocking solution was aspired and replaced by the diluted mAb solution, incubation chambers were sealed with aluminum tape, and incubated while protected from light (2 h RT, 130 rpm shaking). mAb solutions were removed, wells were washed three times with 100 µl washing solution (1×PBS/0.1% Tween20), and the chambers were dismantled. At this point, slides were washed three times 5 minutes in 1×PBS/0.1% Tween20 followed by one 5 minutes wash in 1×PBS. After the last wash, excess liquid was removed without letting the nitrocellulose dry. To detect the mAb bound to their antigen, 270 µl of the secondary antibody Cy5-conjugated AffiniPure F(ab')$_2$ fragment donkey anti-mouse IgG (H+L) (1 µg/ml in 1×PBS/2% BSA/0.05% Tween20, was added. The slide was then covered with a plastic cover-slip and incubated protected from light in a high humidity chamber (RT) for 45 minutes, with shaking (100 rpm). The slides were then washed (as described above) and dried by centrifugation in a vertical position.

Slides were scanned with a ScanArray Gx microarray scanner for Cy5 fluorescence (Ex=649 nm, Em=670 nm) and AF555 (Ex=555 nm, Em=565 nm). Scanned images were quantified using the QuantArray software. mAb affinities for antigens were calculated using NRC proprietary software using a four-step normalization process:

- The quantified signal of both fluorophores Cy5 and AF555 was subtracted with local background signal of each spot.
- Bad spots (with AF555 intensity lower than 33% of average) were excluded.
- To normalize for the total amount of protein in each spot, the Cy5 (anti-mouse IgG) signal was divided by the AF555 (anti-GFP spiked-in normalizer) signal.
- Duplicate spots were averaged. To normalize for 'slide-to-slide' signal intensity variations, the binding intensity of each mAb was divided by the median of the entire slide mAb binding intensities to native proteins.

The result is the mAb binding affinity in fluorescence unit (FU) above median. Antibody-antigen binding was considered specific when the binding affinity value was at least 2 times above the binding affinities standard deviation of all spotted proteins.

The RPPA results (Table 3) showed 1) the specificity of these mAb for rhCA-IX (i.e. no other proteins were detected in the protein mixture), and 2) that all three mAb bind to both native and denatured rhCA-IX ECD. mAb 11H9 and 12H8 bind slightly better to the native protein, whereas mAb 2C7 seems to have a slight increased preference for the denatured protein.

TABLE 3

RPPA results showing the rhCA-IX ECD binding specificity of mAbs 11H9, 12H8 and 2C7

| | Purified Antigen | | |
|---|---|---|---|
| Clone | Native (A) | Denatured (B) | Ratio (A)/(B) (Possibly epitope related) |
| 11H9 | 119.58 | 85.82 | 1.39 |
| 12H8 | 158.01 | 142.32 | 1.11 |
| 2C7 | 178.94 | 208.4 | 0.86 |

| | Antigen in protein mixture | | | |
|---|---|---|---|---|
| Clone | Native (C) | Denatured (D) | mAb binding specificity | mAb concentration in hybridoma CM (µg/ml) |
| 11H9 | 57.83 | 8.33 | rhCA-IX ECD | 4.64 |
| 12H8 | 50.26 | 4.15 | rhCA-IX ECD | 2.52 |
| 2C7 | 44.18 | 3.68 | rhCA-IX ECD | 20.6 |

Example 4: Generation of Chimeric Anti-CA-IX Antibodies

To facilitate large scale production of mAb and to ensure consistency in production, mAb were recombinantly expressed in CHO cells.

Antibody Sequencing:

The $V_H$ and $V_L$ mAb 11H9, 12H8 and 2C7 were sequenced and found to be as follows:

2C7 $V_L$—SEQ ID NO:19
2C7 $V_H$—SEQ ID NO:20
11H9 $V_L$—SEQ ID NO:21
11H9 $V_H$—SEQ ID NO:22
12H8 $V_L$—SEQ ID NO:23
12H8 $V_H$—SEQ ID NO:24

The $V_L$ and $V_H$ sequences were cloned into a human kappa1 light chain and human IgG1 heavy chain frameworks (constant domains), respectively, in the pTT5 vector by Genscript (Piscataway N.J., USA), thereby generating chimeric (c) mAb. The sequences for the chimeric antibodies were as follows:

c2C7 Light chain—SEQ ID NO:25
c2C7 Heavy chain—SEQ ID NO:26
c1H9 Light chain—SEQ ID NO:27
c1H9 Heavy chain—SEQ ID NO:28
c12H8 Light chain—SEQ ID NO:29
c12H8 Heavy chain—SEQ ID NO:30

In addition, all light chain sequences comprised a signal sequence MVLQTQVFISLLLWISGAYG (SEQ ID NO:31) at the N-terminus, while heavy chain sequences comprised the signal sequence MDVVTWRILFLVAAATGTHA (SEQ ID NO:32) at the N-terminus.

Figure 6:
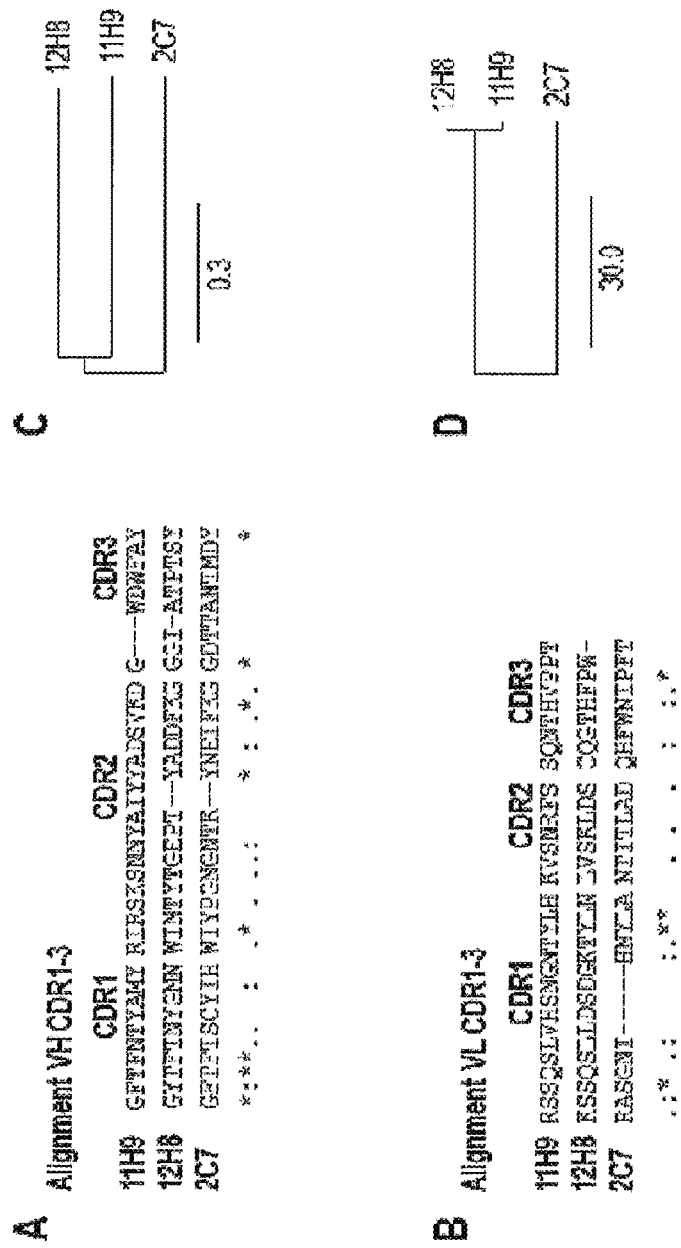
FIG. 6 shows the sequence alignment for CDR 1-3 of mAb 11H9, 12H8, 2C7 $V_H$ (FIG. 6A, SEQ ID NOs: 10-12, 16-18, and 4-6, respectively) and $V_L$ (FIG. 6B; SEQ ID NOs: 7-9, 13-15, and 1-3, respectively) regions and the corresponding phylogenetic tree (FIGS. 6C and 6D, respectively). Consensus symbols: * (asterisk)=single, fully conserved residue: (colon)=conservation between groups of strongly similar properties; scoring>0.5 (Gonnet PAM 250 matrix). (period)=conservation between groups of weakly similar properties; scoring=<0.5 (Gonnet PAM 250 matrix) (Dereeper et al., 2008 and 2010; Edgar, 2004)

CDR regions (Table 4) were also analyzed for a consensus binding sequence by reconstructing a phylogenetic tree (FIG. 6) of the CDR 1-3 regions of the $V_H$ and $V_L$ chains using web-based software (Dereeper A et al., 2008; phylogeny.lirmm.fr/phylo_cgi/index.cgi). The results of this analysis indicated that the CDR regions of both the $V_L$ and $V_H$ regions of mAb 11H9 and 12H8 are more similar to each other than to that of mAb 2C7.

TABLE 4

CDR region sequences for mAb 11H9, 12H8 and 2C7.

| mAb | | Light Chain CDR | | Heavy Chain CDR |
|---|---|---|---|---|
| 2C7 | L1 | RASGNIHNYLA (SEQ ID NO: 1) | H1 | GFTFTSCYIH (SEQ ID NO: 4) |
|  | L2 | NTITLAD (SEQ ID NO: 2) | H2 | WIYPGNGNTKYNEIFKG (SEQ ID NO: 5) |
|  | L3 | QHFWNIPFT (SEQ ID NO: 3) | H3 | GDTTANTMDY (SEQ ID NO: 6) |
| 11H9 | L1 | RSSQSLVHSNGNTYLH (SEQ ID NO: 7) | H1 | GFTFNTYAMY (SEQ ID NO: 10) |
|  | L2 | KVSN RFS (SEQ ID NO: 8) | H2 | RIRSKSNNYAIYYADSVKD (SEQ ID NO: 11) |
|  | L3 | SQNTHVPPT (SEQ ID NO: 9) | H3 | GWDWFAY (SEQ ID NO: 12) |
| 12HD8 | L1 | KSSQSLLDSDGKTYLN (SEQ ID NO: 13) | H1 | GYTFTNYGMN (SEQ ID NO: 16) |
|  | L2 | LVSKLDS (SEQ ID NO: 14) | H2 | WINTYTGEPTYADDFKG (SEQ ID NO: 17) |
|  | L3 | CQGTHFPW (SEQ ID NO: 15) | H3 | GGIATPTSY (SEQ ID NO: 18) |

Figure 7:
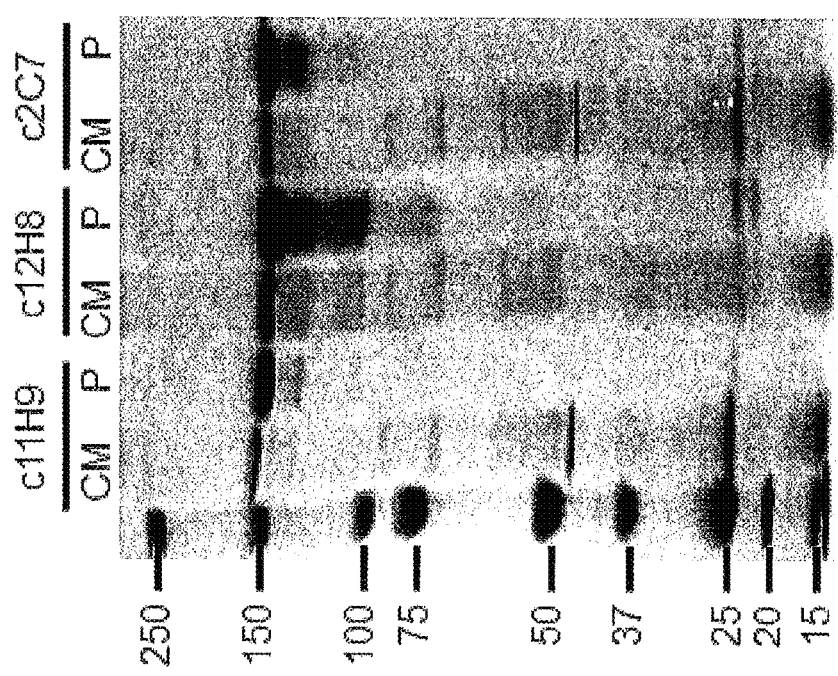
FIG. 7 shows a SDS-PAGE of the recombinantly expressed c11H9, c12H8 and c2C7 mAbs (human IgG1 framework) expressed in CHO cells using a 1:1 $V_L$:$V_H$ ratio in the small-scale (50 mL) expression experiment. Conditioned medium was harvested on day 7, ProtA purified, and quantitated. Both the conditioned medium (CM) and ProtA purified chimeric mAb (P) were evaluated.

Recombinant Antibody Production and Purification:

Chimeric mAb expression was validated through a 2 mL expression scout, where CHO cells were transiently transfected with $V_L$- and $V_H$-containing constructs (1:1 ratio); conditioned medium (CM) was harvested on day 7, and mAb expression levels were evaluated by SDS-PAGE (data not shown). The chimeric (c) 11H9, c12H8 and c2C7 mAb expressed well and a small-scale production (50 mL) was initiated by transiently transfecting CHO cells with the same construct ratio. Conditioned medium (CM) was harvested on day 7, chimeric mAb were purified (ProtA), quantitated, and evaluated by SDS-PAGE. Results are shown in Table 5 and FIG. 7. The data show that all three chimeric mAbs are well expressed by the transiently transfected CHO cells. To distinguish these recombinant antibodies expressed in the human IgG1 framework from the hybridoma derived antibodies, a 'c' for 'chimeric' is added to the ID of these mAbs.

TABLE 5

Recombinant c11H9, c12H8 and c2C7 concentration from 50 mL CHO scout culture by nanodrop after Protein A purification.

| Clone | Frame work | Isotype | volume (uL) | Conc (μg/uL) | Produced (μg/50 mL) |
|---|---|---|---|---|---|
| c11H9 | human | IgG1 | ~500 | 1.461 | 730 |
| c12H8 | human | IgG1 | ~500 | 5.285 | 2642.5 |
| c2C7 | human | IgG1 | ~500 | 2.184 | 1092 |

Example 5: Biophysical Characterization of Anti-CA-IX Antibodies

The anti-CA-IX antibodies obtained in Examples 2 and 4 were characterized using Surface Plasmon Resonance (SPR). The chimeric antibodies of Example 4 were also analyzed for CA cross-reactivity and by Differential Scanning Calorimetry (DSC).

Surface Plasmon Resonance (SPR):

SPR experiments were carried out by capturing the CA-IX mAb (Example 2) from the CM with an anti-mouse Fc antibody immobilized on the chip surface via amine coupling, after which 60 nM rhCA-IX EDC mixture, rhCA-IX EDC monomer, or dimer (Example 1) were flowed over the mAb surface to measure association (binding) followed by flowing running buffer to measure dissociation of any complex formed. All SPR assays were carried out using a BioRad ProteOn XPR36 instrument (Bio-Rad Laboratories (Canada) Ltd. (Mississauga, ON)) with PBST running buffer at a temperature of 25° C. The polyclonal goat anti-mouse Fc (Jackson Immuno Research Laboratories Inc.) capture surface was generated using a GLC sensorchip activated by a 1:10 dilution of the standard BioRad sNHS/EDC solutions injected for 140 s at 100 μL/min in the analyte (horizontal) direction. Immediately after the activation, a 10 μg/mL solution of anti-human Fc antibody in 10 mM NaOAc pH 4.5 was injected in the analyte (horizontal) direction at a flow rate of 25 μL/min until approximately 4000 resonance units (RUs) were immobilized. Remaining active groups were quenched by a 140 s injection of 1M ethanolamine at 100 μL/min in the horizontal direction; this also ensures mock-activated interspots are created for blank referencing.

The screening of the chimeric antibody variants (Example 4) for binding to the rhCA-IX antigen targets occurred in two steps: an indirect capture of the antibody variants onto the anti-human Fc antibody surface in the ligand direction followed by the simultaneous injection of 5 concentrations of purified rhCA-IX antigen (Example 1) and one buffer blank for double referencing in the analyte direction. The change in response due to binding was measured during this antigen injection phase followed by injection of running buffer to measure dissociation of the complex formed. Firstly, one buffer injection for 30 s at 100 μL/min in the ligand direction was used to stabilize the baseline. For each antibody variant capture, non-purified variants in cell-culture media were diluted to 4% in PBST. One to five variants or controls were simultaneously injected in individual ligand channels for 240 s at flow 25 μL/min. This resulted in a capture of approximately 400 to 600 RUs onto the anti-human Fc surface. The first ligand channel was left empty to use as a blank control if required. This capture step was immediately followed by two buffer injections in the analyte direction to stabilize the baseline. Then 60 nM, 20 nM, 6.7 nM, 2.2 nM and 0.74 nM rhCA-IX antigen along with a buffer blank was simultaneously injected at 50 μL/min for 120 s with a 300 s dissociation phase.

For both mAb and chimaeric antibodies, the captured antibody surfaces were regenerated by an 18 s pulse of 0.85% phosphoric acid for 18 s at 100 μL/min to prepare for the next injection cycle. Sensorgrams were aligned and double-referenced using the buffer blank injection and inter-spots, and the resulting sensorgrams were analyzed using ProteOn Manager software v3.1. The double-referenced sensorgrams were fit to the 1:1 binding model to determine the rate constants for association and dissociation ($k_a$ and $k_d$) and the corresponding affinity ($K_D$).

Results are shown in Table 6. mAb 11H9 and 2C7 have a slight preference for the rhCA-IX dimer over the monomer. No data could be obtained for mAb 12H8 when using the monomer, however this mAb binds to the rhCA-IX ECD dimer in a similar manner as mAb 11H9 and 2C7.

To verify that the recombinantly-expressed chimeric antibodies behave similarly to the hybridoma-expressed mAb, SPR antigen-binding experiments were carried out by capturing the c11H9, c12H8 and c2C7 mAb with a goat anti-human Fc antibody surface immobilized on the chip surface. Results are shown in FIG. 8 and Table 6. All three chimeric mAb (c11H8, c12H9 and c2C7) have a relative slow off-rate, confirming similar binding characteristics compared to the original mAb.

TABLE 6

Overview SPR results of purified hybridoma-derived mAb 11H9, 12H8, and 2C7 and the CHO expressed recombinant chimeric Ab c11H9, c12H8 and c2C7 using hCA-IX ECD monomer and/or dimer preps.

| Clone | mAb capture levels | $k_a$ | $k_d$ | $K_D$ |
|---|---|---|---|---|
| Hybridoma-derived mAb | | | | |
| rhCA-IX ECD Mixture (Monomer + Dimer) | | | | |
| 11H9 | 300 | $2.63 \times 10^5$ | $4.84 \times 10^{-4}$ | $1.84 \times 10^{-9}$ |
| 12H8 | 125 | $1.13 \times 10^6$ | $9.70 \times 10^{-12}$ | $8.60 \times 10^{-18}$ |
| 2C7 | 675 | $6.74 \times 10^5$ | $1.17 \times 10^{-3}$ | $1.73 \times 10^{-9}$ |
| rhCA-IX ECD Monomer | | | | |
| 11H9 | 300 | $2.88 \times 10^5$ | $1.65 \times 10^{-3}$ | $5.72 \times 10^{-9}$ |
| 12H8 | 125 | — | Biphasic | |
| 2C7 | 675 | $1.29 \times 10^6$ | $2.59 \times 10^{-3}$ | $3.20 \times 10^{-9}$ |
| rhCA-IX ECD Dimer | | | | |
| 11H9 | 300 | $3.42 \times 10^5$ | $5.84 \times 10^{-5}$ | $1.71 \times 10^{-10}$ |
| 12H8 | 125 | $2.27 \times 10^6$ | $3.22 \times 10^{-4}$ | $1.43 \times 10^{-10}$ |
| 2C7 | 675 | $9.67 \times 10^5$ | $1.36 \times 10^{-3}$ | $1.41 \times 10^{-9}$ |
| Recombinantly expressed Abs | | | | |
| rhCA-IX ECD Dimer | | | | |
| c11H9 | 400 | $1.46 \times 10^5$ | $3.12 \times 10^{-5}$ | $2.14 \times 10^{-10}$ |
| c12H8 | 350 | $5.88 \times 10^5$ | $5.76 \times 10^{-4}$ | $9.79 \times 10^{-10}$ |
| c2C7 | 380 | $2.96 \times 10^5$ | $8.90 \times 10^{-4}$ | $3.01 \times 10^{-9}$ |

Cross-Reactivity Determination by SPR:

To evaluate the cross-reactivity of c11H9, c12H8, and c2C7 to other hCA, binding of the chimeric antibodies to rhCA-IV, rhCA-XII and rhCA-XIV as well as to recombinant murine (rm)CA-IX was measured by SPR by indirect capture (as described previously). CA proteins for the analyte injection were purchased from Sino Biologics Inc.; the proteins were reconstituted as recommended by the manufacturer and diluted to 100 nM in SPR running buffer for binding analysis. The results, shown in FIG. 9, indicate that c11H9, c12H8 and c2C7 are specific for the hCA-IX, as no binding was detected against rhCA-IV, rhCA-XII and rhCA-XIV, or rmCA-IX at the concentration of 100 nM tested.

Differential Scanning Calorimetry (DSC):

To determine the thermostability of c11H9, c12H8 and c2C7, a DSC was performed using a MicroCal auto-VP DSC. Briefly, the stability of 0.125 mg/mL solutions of c11H9, c12H8, and c2C7 in PBS were monitored at a scan rate of 90° C./hour between 25° C. and 100° C. Melting temperatures ($T_m$) were determined from the integrated thermograms using Origin 7 software. The anti-HER1 antibody Cetuximab was used as a positive control. Results are shown in FIG. 10. c12H8 and c2C7 display a thermostability similar to Cetuximab, whereas c11H9 seems slightly less stable than c12H8 and c2C7.

Example 6: Epitope Mapping

The monoclonal antibodies of Example 2 and/or the chimeric antibodies of Example 4 were used to perform various methods of epitope mapping.

Pepscan:

Epitope mapping services were provided by Pepscan (Lelystad, The Netherlands; pepscan.com). CLIPS™ technology (Chemical Linkage of Peptides onto Scaffolds) was used to gain insight into the binding epitope. The method is based on the chemical linkage of homocysteines that flank synthetic peptides (15 aa long) covering the entire hCA-IX protein, in addition to a synthetic scaffold containing a benzyl-bromide group (Timmerman et al., 2009). The purified mAb of Example 2 were screened against peptides in a 'linear' and single 'cycle' format.

The peptide binding results for 11H9, 12H8 and 2C7 are shown in FIG. 11A, B, C. 12H8 and 2C9 preferred binding to the 'cycle' peptide whereas 11H9 did not display such preference. Results also showed that 11H9 and 12H8 bind to non-overlapping epitopes EEDLPGEE (SEQ ID NO:34) and LPRMQEDSPLGGG (SEQ ID NO:35), respectively, in the unstructured PG domain. For 2C7, signals were detected for epitopes in the catalytic domain, though they were too weak to determine a specific binding epitope. However, when combined with the yeast-surface display data (see below) showing sensitivity to reduction, a putative epitope for mAb 2C7 can be identified in the structured catalytic domain: PSDFSRYFQYEGSL (SEQ ID NO:36). See FIG. 11D.

Epitope Binning by SPR:

To evaluate whether mAb belong to the same class, SPR epitope binning experiments were carried out with purified hybridoma-derived mouse monoclonal 11H9, 12H8 and 2C7 (Example 2), as well as recombinantly CHO expressed c11H9, c12H8 and c2C7 (Example 3). Antibodies were directly immobilized on the chips surface ('mAb1'), after which either the rhCA-IX ECD monomer or dimer was flowed, followed by flowing the same antibody ('mAb2'); these methods are described in Abdiche et al. (2011). All experiments were performed on a ProteOn XPR36 biosensor at 25° C. using PBST as running buffer (PBS with 0.05% v/v Tween20). GLM sensor chips and coupling reagents (10 mM sodium acetate, pH 4.5, sulfo-N-hydroxysuccinimide (SNHS), 1-ethyl-3-(3-dimethylaminporpyl)-carbodiimide hydrochloride (EDC), and ethanolamine) were purchased from BioRad, Inc (Hercules, Calif.).

Creating Antibodies Array—

Antibodies (Mab1) were immobilized on the GLM chip surface at 30 µl/min. The activation reagents (at stock concentration of 0.4M EDC and 0.1M SNHS in water) were diluted 20-fold each in water. The top (A1) horizontal channel (the Analyte channel in the Proteon control software) was activated for 3 min with the diluted activation reagents. Next, c11H9, c12H8, and c2C7 were each diluted to 20 µg/ml in 10 mM acetate pH4.5 and injected for 3 min in separate vertical (L1 to L6) channels (the Ligand channel in the Proteon control software), followed with a 3 min injection of ethanolamine to block the reactive spots. The multi-channel module (MCM) was then rotated and another 3 min injection of ethanolamine was done on the activated horizontal channel (A1). This four-step 'activation-binding-and-2× deactivation' procedure was then repeated on each of the horizontal channels (A2 to A6).

Sandwich Epitope Binning—

The two-step sandwich epitope binning was done at 30 µl/min in the analyte orientation. 100 nM CA-IX antigen was injected for 3 min, immediately followed by a 3 min injection of Mab2 at 100 nM. Immobilized mAb (mAb1) surfaces were regenerated by a 18 s injection of 0.85% phosphoric acid at 100 µl/min. This two-step injection (CA-IX-mAb2) was repeated for each individual Mab2 with monomer and dimer CA-IX. Each mAb were also tested simultaneously and used as Mab1 (immobilized on the chip) and mAb2 (in solution). To monitor the CA-IX dissociation from the immobilized Mab1 PBST was injected instead of mAb2.

Results are shown in FIG. 12B. The data shows that none of the antibodies compete for binding to either the rhCA-IX ECD monomer or dimer, indicating that these three mAb bind to distinct, non-overlapping CA-IX epitopes.

Epitope Mapping by Yeast Surface Display (YSD):

The hCA-IX ectodomain (ECD) and fragments thereof were expressed and covalently displayed on the surface of yeast cells (Feldhaus et al., 2003). The hCA-IX fragments covering the entire hCA-IX ECD (FIG. 13A) or the PG domain alone (FIG. 13B) were expressed as fusion proteins (Aga2-HA-(CA-IX)-MYC (pPNL6 vector) or (CA-IX)-Aga2-MYC (pPNL200 vector)) on the yeast cell surface. The YSD vectors (pPNL6 and pPNL200) were from The Pacific Northwest National Laboratory, USA. The displayed CA-IX fragments were used to map the amino acid sequences to which 11H9, 12H8, and 2C7 bind. The binding of the mAb to yeast cells was performed using a whole yeast cell ELISA. The amount of properly displayed fusion protein was measured by probing with an anti-MYC antibody, followed by an HRP-conjugated secondary antibody. The anti-MYC signal was then used to normalize the binding signal for c11H9, c12H8, and c2C7. For determination of linear versus conformational epitopes, yeast cells with displayed CA-IX fragments were heated at 80° C. for 30 min, then chilled on ice for 20 min prior to labeling with antibodies. The binding of mAb to denatured yeast cells was normalized to the anti-MYC signal. The ratio of normalized anti-CA-IX signals of each mAb on native versus denatured hCA-IX peptide was thus indicative of the conformational nature of the epitope. In the native hCA-IX experiments, the commercial M75 mAb was used as a positive control; the epitope of this mAb is known (Zavada et al., 2000) and is located in the hCA-IX PG domain.

Tables 7 (native hCA-IX ECD) and 8 (denatured hCA-IX ECD) show that the binding epitopes for c11H9 and c12H8 are located in hCA-IX's PG domain (as is that for M75), whereas c2C7 binds to an epitope in the catalytic domain, thereby confirming the PepScan observations. This data set also indicates that the c11H9 and c12H8 epitopes are likely to be unstructured, whereas that of the c2C7 mAb is probably structured, given the observation that binding is lost to the denatured hCA-IX protein fragments.

TABLE 7

Results of the epitope mapping experiments by YSD of c11H9, c12H8 and c2C7 on native peptides covering the hCA-IX ECD. Anti-CA-IX antibody binding intensity is normalized on CA-IX_MYC expression on cells. −, no binding; +, binding.

| Clone | YSD vector | Fused protein | CA-IX Fragment | CA-IX amino acids | CA-IX Domain | Anti-hCA-IX antibody binding intensity | | | |
|---|---|---|---|---|---|---|---|---|---|
| | | | | | | c11H9 | c12H8 | c2C7 | M75 control |
| 1A | PNL6 | Aga2-HA-CA9-MYC | 1 | 53-111 | PG | + | − | − | ++ |
| 2B | PNL6 | Aga2-HA-CA9-MYC | 2 | 38-136 | +PG+ | ++ | ++ | − | ++ |
| 3A | PNL6 | Aga2-HA-CA9-MYC | 3 | 1-136 | SP+PG+ | +++ | + | − | ++++ |
| 4A | PNL6 | Aga2-HA-CA9-MYC | 4 | 135-391 | CA | − | − | ++ | − |
| 5A | PNL6 | Aga2-HA-CA9-MYC | 5 | 112-391 | +CA | − | − | +++ | − |
| 6B | PNL6 | Aga2-HA-CA9-MYC | 6 | 135-414 | CA+ | − | − | +++ | − |
| 7B | PNL6 | Aga2-HA-CA9-MYC | 7 | 112-414 | +CA+ | − | − | +++ | − |
| 8B | PNL6 | Aga2-HA-CA9-MYC | 8 | 38-414 | +PG+CA+ | +++ | +++ | + | +++ |
| 9A | PNL6 | Aga2-HA-CA9-MYC | 9 | 1-414 | SP+PG+CA+ | ++++ | ++ | Low level display of CA-IX | ++++ |
| 11B | PNL6 | Aga2-HA-X-MYC | Plasmid Ctrl | Neg Ctrl | — | − | − | − | − |
| EBY 100 | No-plasmid | None | Strain Ctrl | Neg Ctrl | — | − | − | − | − |
| 12B | PNL200 | CA9-Aga2-MYC | 1 | 53-111 | PG | ++ | − | − | ND |
| 13A | PNL200 | CA9-Aga2-MYC | 2 | 38-136 | +PG+ | ++ | +++ | − | ND |
| 14A | PNL200 | CA9-Aga2-MYC | 3 | 1-136 | SP+PG+ | ++++ | + | − | ND |
| 15B | PNL200 | CA9-Aga2-MYC | 4 | 135-391 | CA | − | − | + | ND |
| 16B | PNL200 | CA9-Aga2-MYC | 5 | 112-391 | +CA | − | − | + | ND |
| 17B | PNL200 | CA9-Aga2-MYC | 6 | 135-414 | CA+ | − | − | +++++ | ND |
| 18A | PNL200 | CA9-Aga2-MYC | 7 | 112-414 | +CA+ | − | − | +++++ | ND |
| 19B | PNL200 | CA9-Aga2-MYC | 8 | 38-414 | +PG+CA+ | ++++ | ++++ | +++++ | ND |

TABLE 7-continued

Results of the epitope mapping experiments by YSD of c11H9, c12H8 and c2C7 on native peptides covering the hCA-IX ECD. Anti-CA-IX antibody binding intensity is normalized on CA-IX_MYC expression on cells. −, no binding; +, binding.

| Clone | YSD vector | Fused protein | CA-IX Fragment | CA-IX amino acids | CA-IX Domain | Anti-hCA-IX antibody binding intensity | | | |
|---|---|---|---|---|---|---|---|---|---|
| | | | | | | c11H9 | c12H8 | c2C7 | M75 control |
| 20A | PNL200 | CA9-Aga2-MYC | 9 | 1-414 | SP+PG+CA+ | Low level display of CA-IX | Low level display of CA-IX | Low level display of CA-IX | ND |
| 22A | PNL200 | X-Aga2-MYC | Plasmid Ctrl | Neg Ctrl | — | − | − | − | ND |
| EBY 100 | No plasmid | None | Strain Ctrl | Neg Ctrl | — | − | − | − | ND |

TABLE 8

Results of the epitope mapping experiments by YSD of c11H9, c12H8 and c2C7 on denatured peptides covering the hCA-IX ECD. Anti-CA-IX antibody binding intensity is normalized on CA-IX_MYC expression on cells. −, no binding; +, binding.

| Clone | YSD vector | Fused protein | hCA-IX Fragment | hCA-IX amino acids | hCA-IX Domain | Anti-hCA-IX antibody binding intensity | | | |
|---|---|---|---|---|---|---|---|---|---|
| | | | | | | c11H9 | c12H8 | c2C7 | M75 control |
| 1A | PNL6 | Aga2-HA-CA9-MYC | 1 | 53-111 | PG | ++++ | + | − | ND |
| 2B | PNL6 | Aga2-HA-CA9-MYC | 2 | 38-136 | +PG+ | ++++ | ++++ | − | ND |
| 3A | PNL6 | Aga2-HA-CA9-MYC | 3 | 1-136 | SP+PG+ | ++++++ | + | − | ND |
| 4A | PNL6 | Aga2-HA-CA9-MYC | 4 | 135-391 | CA | − | − | − | ND |
| 5A | PNL6 | Aga2-HA-CA9-MYC | 5 | 112-391 | +CA | − | − | − | ND |
| 6B | PNL6 | Aga2-HA-CA9-MYC | 6 | 135-414 | CA+ | − | − | − | ND |
| 7B | PNL6 | Aga2-HA-CA9-MYC | 7 | 112-414 | +CA+ | − | − | − | ND |
| 8B | PNL6 | Aga2-HA-CA9-MYC | 8 | 38-414 | +PG+CA+ | +++++ | ++++ | − | ND |
| 9A | PNL6 | Aga2-HA-CA9-MYC | 9 | 1-414 | SP+PG+CA+ | Low level display of CA-IX | Low level display of CA-IX | − | ND |
| 11B | PNL6 | Aga2-HA-X-MYC | Plasmid Ctrl | Neg Ctrl | — | − | − | − | ND |
| EBY 100 | No-plasmid | None | Strain Ctrl | Neg Ctrl | — | − | − | − | ND |
| 12B | PNL200 | CA9-Aga2-MYC | 1 | 53-111 | PG | ++++++ | − | − | ND |
| 13A | PNL200 | CA9-Aga2-MYC | 2 | 38-136 | +PG+ | +++ | ++ | − | ND |
| 14A | PNL200 | CA9-Aga2-MYC | 3 | 1-136 | SP+PG+ | ++++++ | − | − | ND |
| 15B | PNL200 | CA9-Aga2-MYC | 4 | 135-391 | CA | − | − | − | ND |
| 16B | PNL200 | CA9-Aga2-MYC | 5 | 112-391 | +CA | − | − | − | ND |
| 17B | PNL200 | CA9-Aga2-MYC | 6 | 135-414 | CA+ | − | − | − | ND |
| 18A | PNL200 | CA9-Aga2-MYC | 7 | 112-414 | +CA+ | − | − | − | ND |
| 19B | PNL200 | CA9-Aga2-MYC | 8 | 38-414 | +PG+CA+ | ++++++ | ++++ | − | ND |
| 20A | PNL200 | CA9-Aga2-MYC | 9 | 1-414 | SP+PG+CA+ | Low level display of CA-IX | Low level display of CA-IX | − | ND |
| 22A | PNL200 | X-Aga2-MYC | Plasmid Ctrl | Neg Ctrl | — | − | − | − | ND |
| EBY 100 | No-plasmid | None | Strain Ctrl | Neg Ctrl | — | − | − | − | ND |

For higher resolution mapping of the epitopes in the hCA-IX PG domain, tiling peptides of 15 amino acid (aa) residues (with a 5 aa overlap) encompassing aa 37-140 of the native hCA-IX PG domain (Tables 9 and 10) were prepared. Corresponding DNA sequences were PCR-amplified, cloned into pPNL6 using GAP repair (Gietz et al., 1992), and displayed on the yeast surface.

TABLE 9

Figure 13:
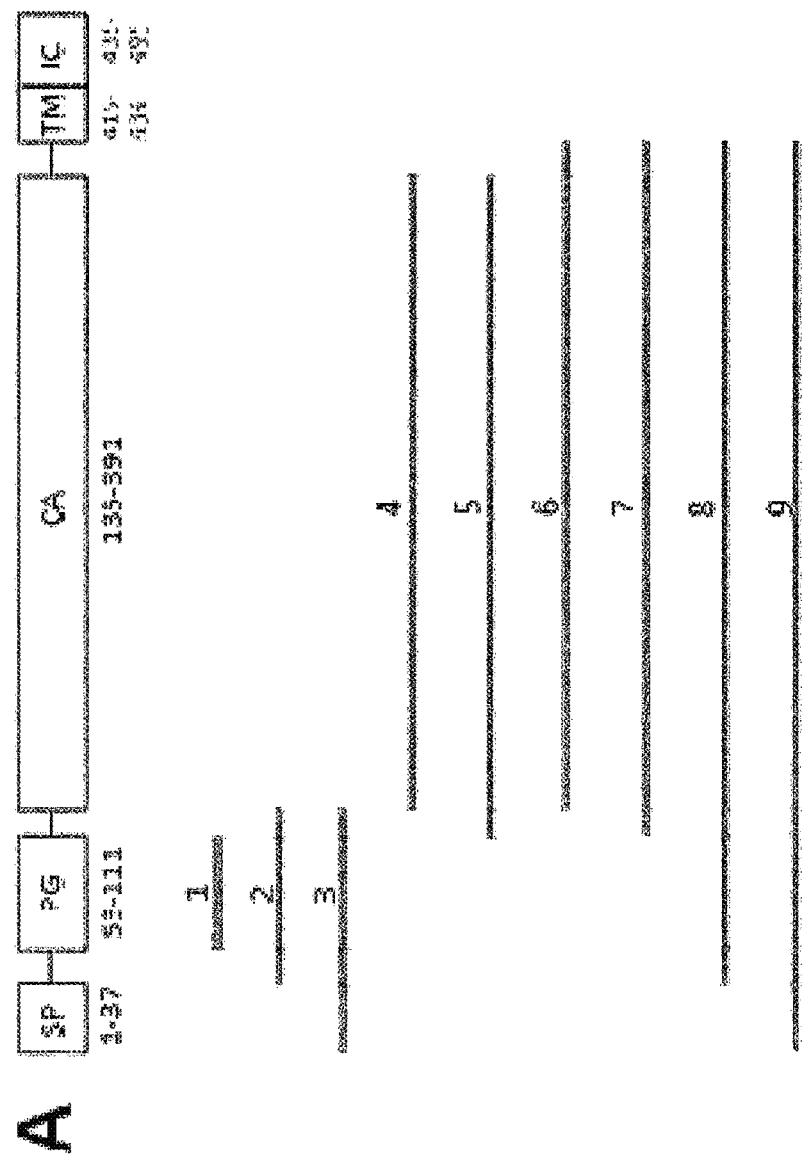
FIG. 13A shows the nine (9) peptides covering the entire hCA-IX expressed on the yeast cell surface membrane to map the binding epitope of the recombinantly-expressed c11H9, c12H8, and c2C7 mAb. Fine mapping using fourteen (14) peptides covering the hCA-IX PG domain (FIG. 13B) was only further used to identify specific peptide binding epitopes of these mAb.
Figure 13:
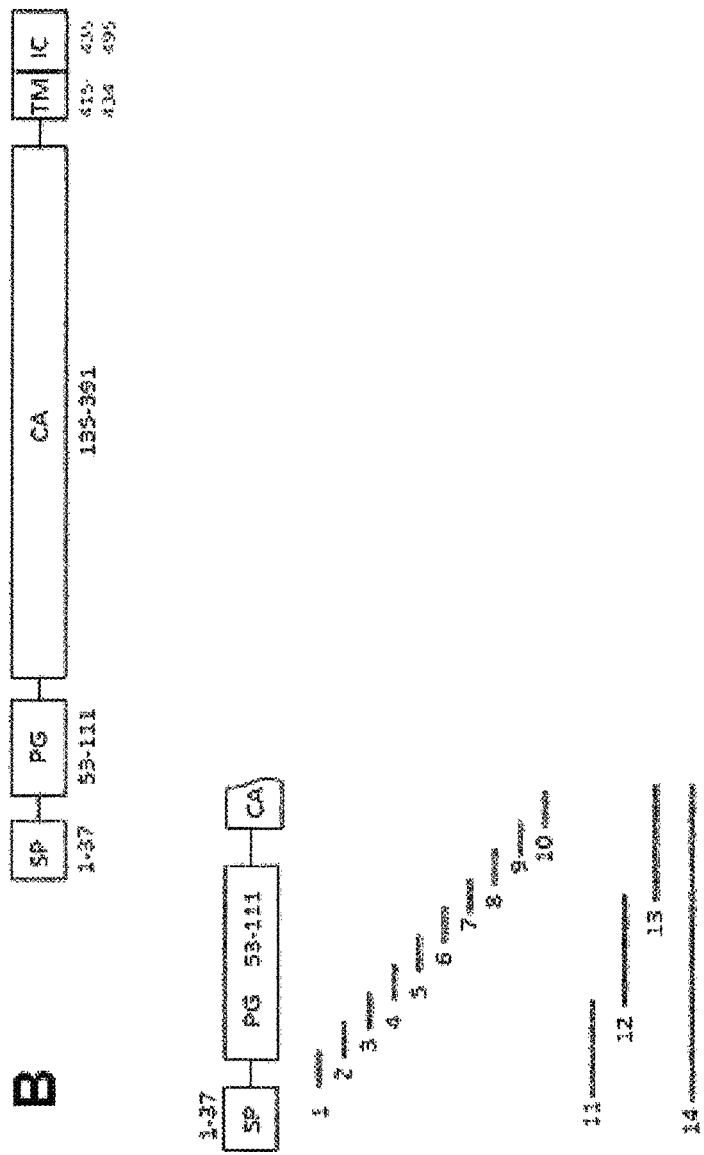

Amino acid sequence of 15 amino acid tiling peptides encompassing amino acids 37-140 of the entire hCA-IX (see FIG. 13B).

| Fragment # | hCA-IX amino acids | amino acid sequence | SEQ ID NO: |
|---|---|---|---|
| 1 | 37-51 | PQRLPRMQEDSPLGG | 38 |
| 2 | 47-61 | SPLGGGSSGEDDPLG | 39 |
| 3 | 57-71 | DDPLGEEDLPSEEDS | 40 |
| 4 | 67-81 | SEEDSPREEDPPGEE | 41 |
| 5 | 77-91 | PPGEEDLPGEEDLPG | 42 |
| 6 | 87-101 | EDLPGEEDLPEVKPK | 43 |
| 7 | 97-111 | EVKPKSEEEGSLKLE | 44 |
| 8 | 107-121 | SLKLEDLPTVEAPGD | 45 |
| 9 | 117-131 | EAPGDPQEPQNNAHR | 46 |
| 10 | 126-140 | QNNAHRDKEGDDQSH | 47 |
| 11 | 37-71 | PQRLPRMQEDSPLGGGSSGEDDPLGEEDLPSEEDS | 48 |
| 12 | 67-111 | SEEDSPREEDPPGEEDLPGEEDLPEVKPKSEEEGSLKLE | 49 |
| 13 | 107-140 | SLKLEDLPTVEAPGDPQEPQNNAHRDKEGDDQSH | 50 |
| 14 | 37-140 | PQRLPRMQEDSPLGGGSSGEDDPLGEEDLPSEEDSPREEDPPGEEDLPGEEDLPEVKPKSEEEGSLKLEDLPTVEAPGDPQEPQNNAHRDKEGDDQSH | 51 |

TABLE 10

Results of the epitope mapping experiments by YSD of c11H9, c12H8 and c2C7 on native peptides covering the hCA-IX ECD PG domain. Anti-CA-IX antibody binding intensity is normalized on CA-IX_MYC expression on cells. −, no binding; +, binding.

| Clone | YSD vector | Fused protein | hCA-IX PG domain Fragment | Peptide length (amino acids) | hCA-IX amino acids | Anti-hCA-IX antibody binding intensity | | | |
|---|---|---|---|---|---|---|---|---|---|
| | | | | | | c11H9 | c12H8 | c2C7 | M75 |
| 1 A + B | PNL6 | Aga2-HA-CA9-MYC | 1 | 15 | 37-51 | − | +++ | − | − |
| 2 A + B | PNL6 | Aga2-HA-CA9-MYC | 2 | 15 | 47-61 | − | − | − | − |
| 3 A + B | PNL6 | Aga2-HA-CA9-MYC | 3 | 15 | 57-71 | − | − | − | ++ |
| 4 A + B | PNL6 | Aga2-HA-CA9-MYC | 4 | 15 | 67-81 | − | − | − | − |
| 5 A + B | PNL6 | Aga2-HA-CA9-MYC | 5 | 15 | 77-91 | + | − | − | + |
| 6 A + B | PNL6 | Aga2-HA-CA9-MYC | 6 | 15 | 87-101 | + | − | − | − |
| 7 A + B | PNL6 | Aga2-HA-CA9-MYC | 7 | 15 | 97-111 | − | − | − | − |
| 8 A + B | PNL6 | Aga2-HA-CA9-MYC | 8 | 15 | 107-121 | − | − | − | − |
| 9 A + B | PNL6 | Aga2-HA-CA9-MYC | 9 | 15 | 117-131 | − | − | − | − |
| 10 A + B | PNL6 | Aga2-HA-CA9-MYC | 10 | 15 | 126-140 | − | − | − | − |
| 11 A + B | PNL6 | Aga2-HA-CA9-MYC | 11 | 35 | 37-71 | − | +++ | − | +++ |
| 12 A + B | PNL6 | Aga2-HA-CA9-MYC | 12 | 45 | 67-111 | ++ | − | − | ++ |
| 13 A + B | PNL6 | Aga2-HA-CA9-MYC | 13 | 34 | 107-140 | − | − | − | − |
| 14 A + B | PNL6 | Aga2-HA-CA9-MYC | 14 | 104 | 37-140 | +++ | +++ | − | +++ |
| 15 A + B | PNL6 | Aga2-HA-X-MYC | Plasmid Ctrl | none | — | − | − | − | − |

Yeast cell ELISA with these YSD tiling peptides showed that c11H9 and M75 share similar, although not identical binding epitopes; the c11H9 epitope contained the repeat GEEDLP (SEQ ID NO:37) sequence, which appeared four times in the PG domain. c12H8 bound to an epitope that was distinguishable in the PG domain from that of c11H9 and M75; specifically, c12H8 bound to an epitope containing the unique sequence PQRLPRMQEDSPLGG (SEQ ID NO:38) located at the N-terminus. These data were in agreement with PepScan and SPR binning experimental results. Taking all experimental results together, the putative epitopes for the antibodies were proposed to be: EEDLPGEE (SEQ ID NO:34) for 11H9, PQRLPRMQEDSPLGG (SEQ ID NO:38) for 12H8, and PSDFSRYFQYEGSL (SEQ ID NO: 36) for 2C7.

Using similar methods, additional fine mapping of the epitope for c12H8 by YSD was carried out by N- and C-terminal deletion of fragment #1 in Table 9 (data not shown). In this manner, the minimal epitope for c12H8 was defined as LPRMQEDSP (SEQ ID NO:52), corresponding to aa 40-48 of CA-IX. Similarly, N- and C-terminal deletion of fragment #5 and #6 in Table 9, the minimal epitope for c11H9 was determined to be EDLPGEED (SEQ ID NO:53), which corresponds to aa 81-88 and aa 87-94 of CA-IX. Epitope mapping of the M75 epitope (data not shown) is in agreement with previous reports (see for example Zavada et al, 2000) that the minimal epitope for this antibody is GEEDLP (SEQ ID NO:37).

Example 7: Functional Characterization of Anti-CA-IX mAb

The ability of the anti-CA-IX mAb obtained in Example 2 to inhibit in vitro enzyme activity was evaluated, the cell line was verified and an ADC assay was performed.

Figure 14:
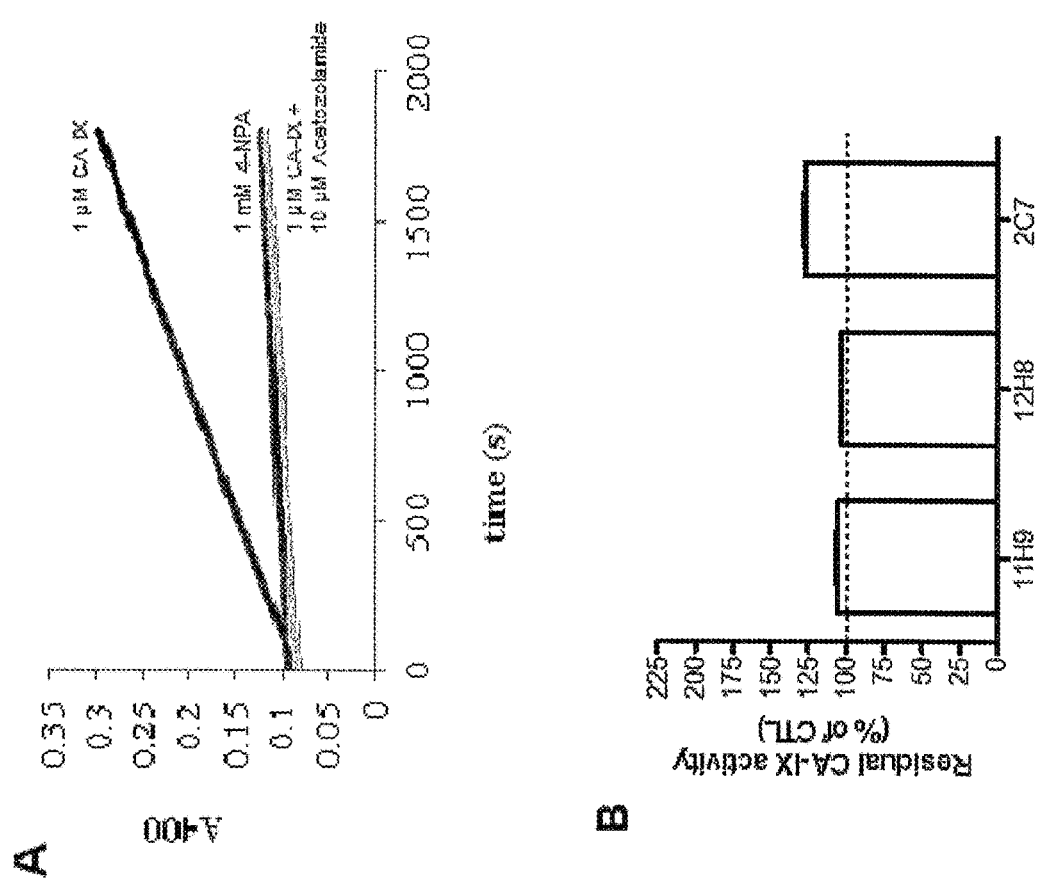
FIG. 14 are graphs used in the evaluation of the enzyme-inhibiting attributes of hybridoma-derived mAb 11H9, 12H8 and 2C7.

In Vitro rhcCA-IX Enzyme Activity Inhibition:

To determine whether the CA-IX mAb can inhibit the enzyme activity of the rhCA-IX ECD protein, an activity assay, detecting the esterase activity of the enzyme using 4-Methylumbelliferyl acetate (Sigma Aldrich) as substrate was performed. The kinetic measurements were carried out in 96-well solid black microplates (Corning) at pH 7.5 in a reaction mixture containing 25 mM MOPS, 15 mM $Na_2SO_4$, 0.5 mM EDTA and 2% (v/v) DMSO (final concentration). A final enzyme concentration of 0.5 µM for the dimer or 1 µM for the monomer was used. The enzyme was pre-incubated for 30 minutes at room temperature with increasing concentration of mAb (0.0625 to 4 µM) diluted in DPBS (Hyclone). Reactions were initiated by the addition of 100 µM 4-Methylumbelliferylacetate. The rate of substrate hydrolysis was determined by monitoring 4-Methylumbelliferone-released fluorescence (excitation A, 380 nm; emission A, 440 nm) as a function of time using the EnVision 2104 plate reader (Perkin Elmer). The substrate autohydrolysis control values were subtracted from the observed total reaction velocities. Acetazolamide (Sigma Aldrich) at a concentration of 10 µM fully inhibited the activity of the rhCA-IX enzyme. Rates were determined in the initial and 'end portion' of each of the curves. Several concentrations of the rhCA-IX ECD mixture of Example 1 were tested and bench-marked against rhCA-IX purchased from R&D (data not shown). Using 1 µM rhCA-IX ECD, enzyme activity of the mAb was measured using a 4:1 (2C7) or 1:1 (11H9, 12H8) molar mAb: rhCA-IX ECD ratio. Results are shown in FIG. 14 and Table 11. None of the tested mAb showed any enzyme inhibition activity.

TABLE 11

Enzyme inhibition data for hybridoma-derived 11H9, 12H8 and 2C7 using the rhCA-IX ECD mixture. For 2C7, a ratio of (mAb:rhCA-IX ECD mixture) of 4:1 was used. For 11H9 and 12H8, a ratio of (mAb:rhCA-IX ECD mixture) of 1:1 was used.

| Clone | Data 1 | Data 2 | % rhCA-IX ECD Activity | STDEV | % rhCA-IX ECD Inhibition | Comments |
|---|---|---|---|---|---|---|
| 2C7 | 125.73 | 128.77 | 127.25 | 2.15 | — | No inhibition |
| 11H9 | 107.08 | 104.47 | 105.77 | 1.84 | — | No inhibition |
| 12H8 | 102.8 | — | 102.8 | — | — | No inhibition |

Figure 15:
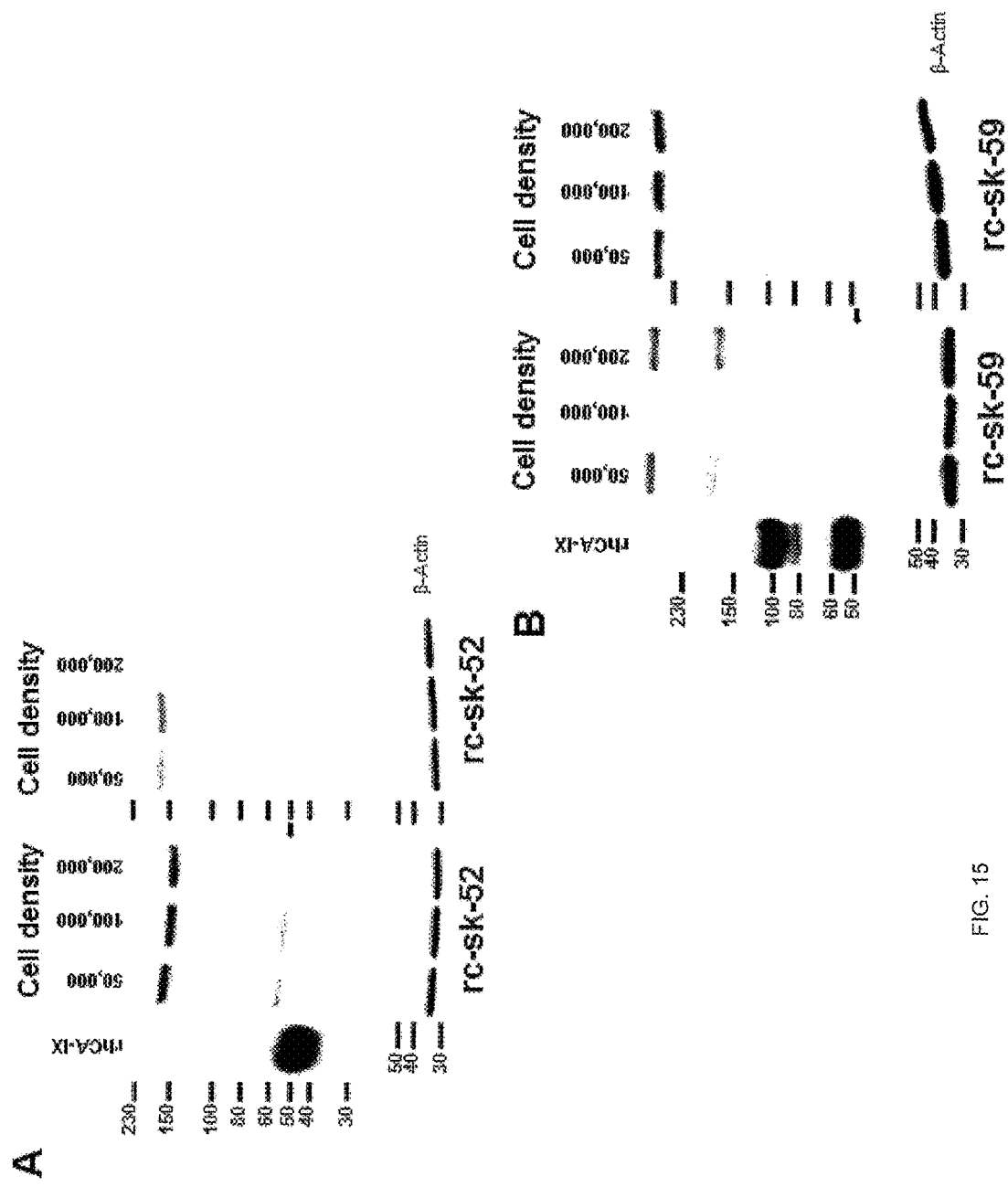
FIG. 15 shows SDS-PAGE evaluation (whole cell lysate) of the non-transfected human renal carcinoma cell lines SK-RC-52 and SK-RC-59 for the expression of hCA-IX under non-reducing (FIG. 15A) and reducing (FIG. 15B) conditions.

Cell Line Verification:

Non-transfected human renal tumor sk-rc-59 and sk-rc-52 cell lines (Dr G Ritter, MSKCC, NY, USA) were obtained to evaluate binding of the anti-CA-IX mAb to cell surface CA-IX. Western blot analysis of these cell lines under non-reducing and reducing conditions (FIG. 15) confirmed the hCA-IX expression levels of the sk-rc-52 cell line (arrow), whereas no CA-IX could be detected in the sk-rc-59 cell line. Equal protein quantities were loaded (BCA protein assay) and confirmed by actin blot.

Figure 16:
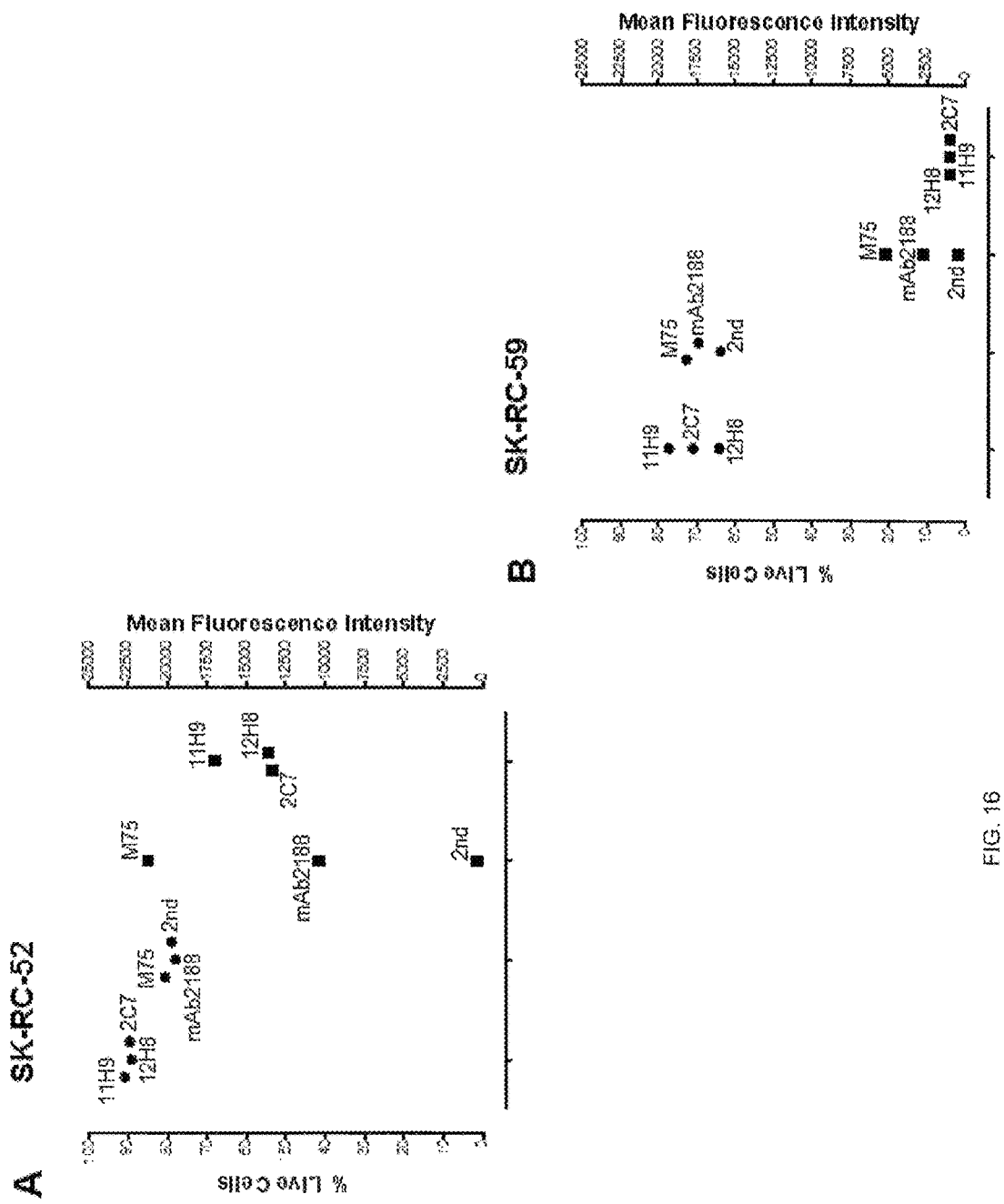
FIG. 16 shows the graphical results of measuring whether the hybridoma-derived mAb 11H9, 12H8 and 2C7 bind to their cognate target expressed by the human renal carcinoma SK-RC-52 (FIG. 16A; high hCA-IX) and SK-RC-59 (FIG. 16B; low hCA-IX) cell lines. The % of live cells in each of the experiments is on the left Y-axis while the mean fluorescent intensity due to mAb binding is on the right Y-axis. The M75 mAb (Zavada et al., 1993) and the commercial hCA-IX mAb (mAb2188) were used as positive controls; the secondary mAb alone (2nd) was used to evaluate non-specific signals.

Flow Cytometry:

mAb were evaluated in a flow cytometry experiment using the sk-rc-59 (low CA-IX expression) and sk-rc-52 (high CA-IX expression) cell lines. Cells were grown to 80% confluency in T75 flasks using MEM/10% FBS medium supplemented with non-essential amino acids (NEAA), washed with dPBS (37° C.) and harvested using non-enzymatic cell dissociation buffer (37° C.). Cells were then transferred to 50 mL tubes, spun down (1100 rpm, RT, 5 min) and re-suspended in cell growth medium. Cells were counted and divided in $10^6$ cell containing aliquots, spun down (1100 rpm, RT, 2 min), re-suspended in ice-cold dPBS/10% FBS containing anti-CA-IX mAb (10 µg/mL final concentration) and incubated (50 min, 4° C.). Cells were then washed with ice-cold dPBS/10% FBS, spun down (1100 rpm, 4° C., 3 min), and re-suspended in 500 µL ice-cold dPBS/10% FBS containing Alexa-488 Goat anti-mouse IgG (10 µg/mL final concentration). After incubation in the dark (25 min, 4° C.), cells were washed with ice-cold dPBS/10% FBS, spun down (1100 rpm, 4° C., 3 min), re-suspended in ice-cold dPBS/10% FBS containing Propidium Iodine (PI; 10 µg/mL final concentration) and finally filtered over a gauze mesh prior to FACS analysis using a BD Biosciences LSR II™ flow cytometer. As controls, a commercially available mAb (R&D, Clone #303123) and the M75 mAb (provided by Dr E Oosterwijk, Radboud University Nijmegen, The Netherlands) were used. Experiments were plotted per cell line and results are shown in FIG. 16. These results showed that mAb 11H9 binds slightly better to hCA-IX expressed by the sk-rc-52 cell line compared to 12H8 and 2C7, whereas virtually no binding was detected on the low hCA-IX expressing sk-rc-59 cells.

Figure 17:
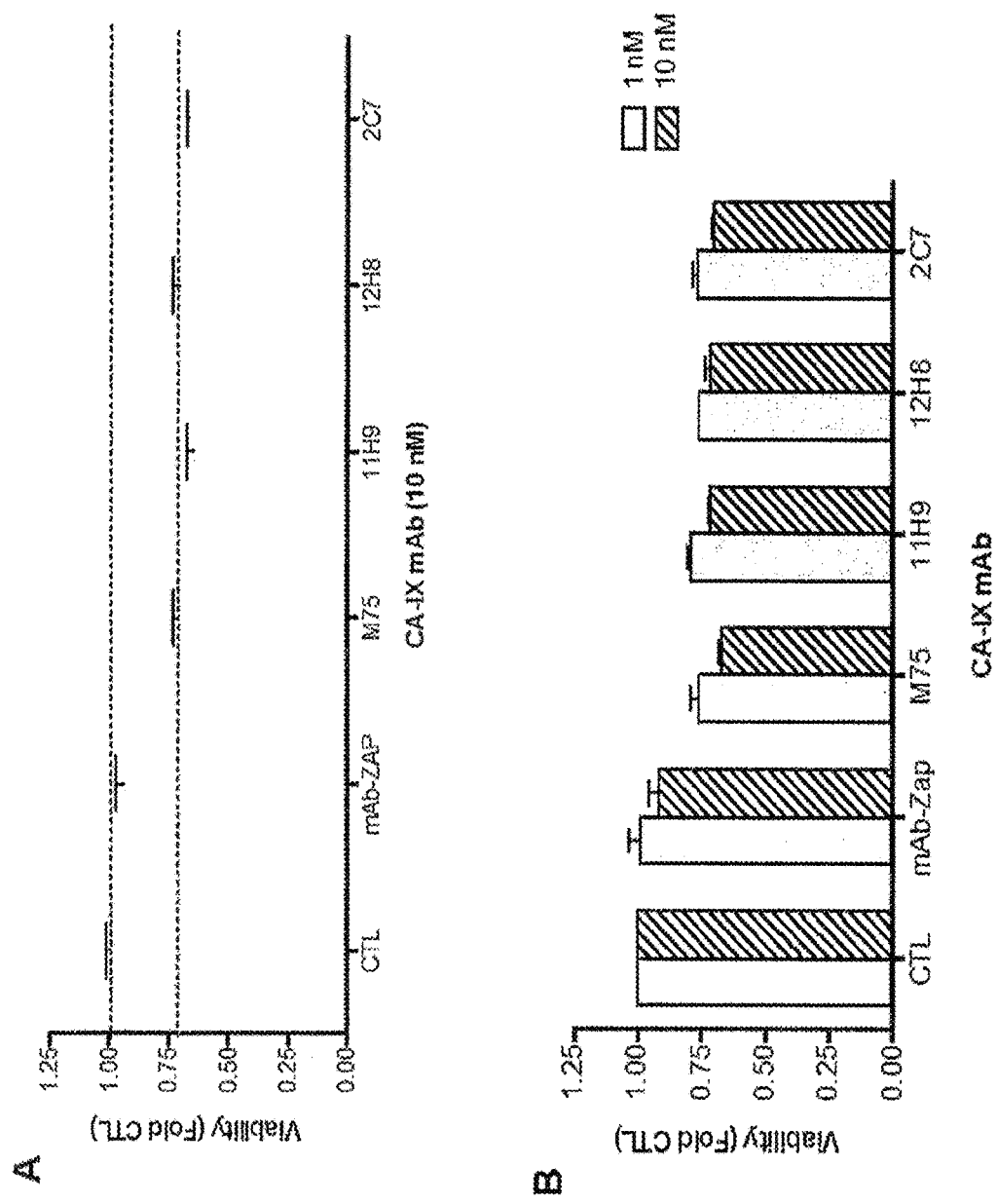
FIG. 17 shows bar charts for evaluating the ADC potential of hybridoma-derived mAb 11H9, 12H8 and 2C7 in a surrogate ADC assay using the sk-rc-52 cells.
Figure 18:
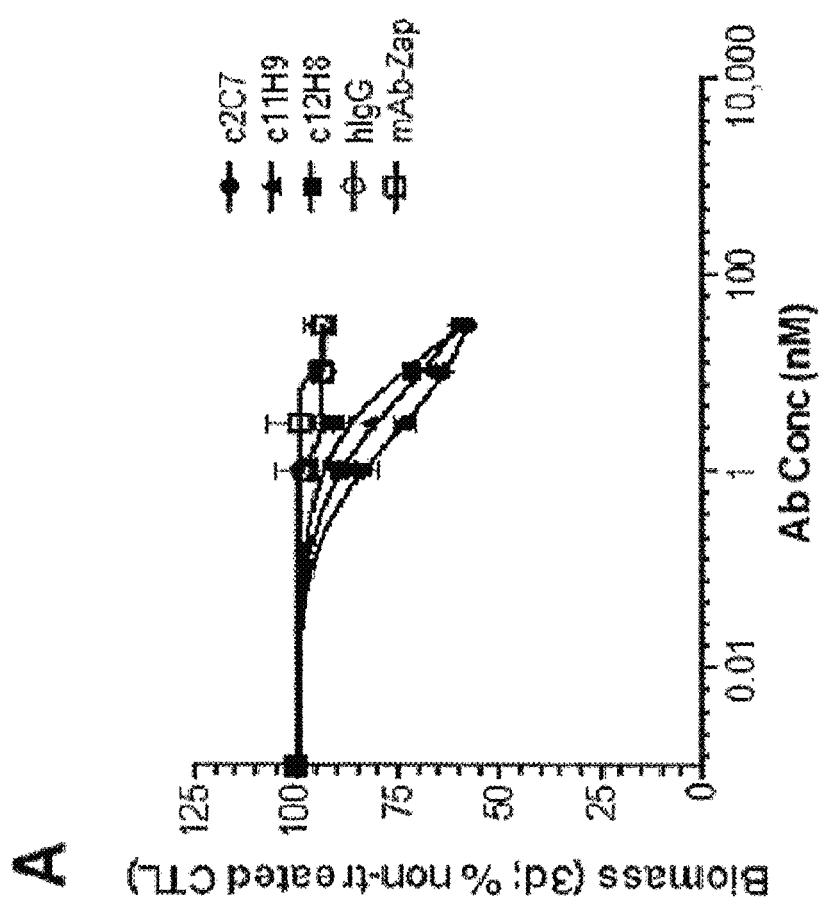
FIG. 18 shows a dose response (0-100 nM) of the potential ADC candidates c11H9, c12H8 and c2C7 in ADC assays using the SK-RC-52 cells.
Figure 18:
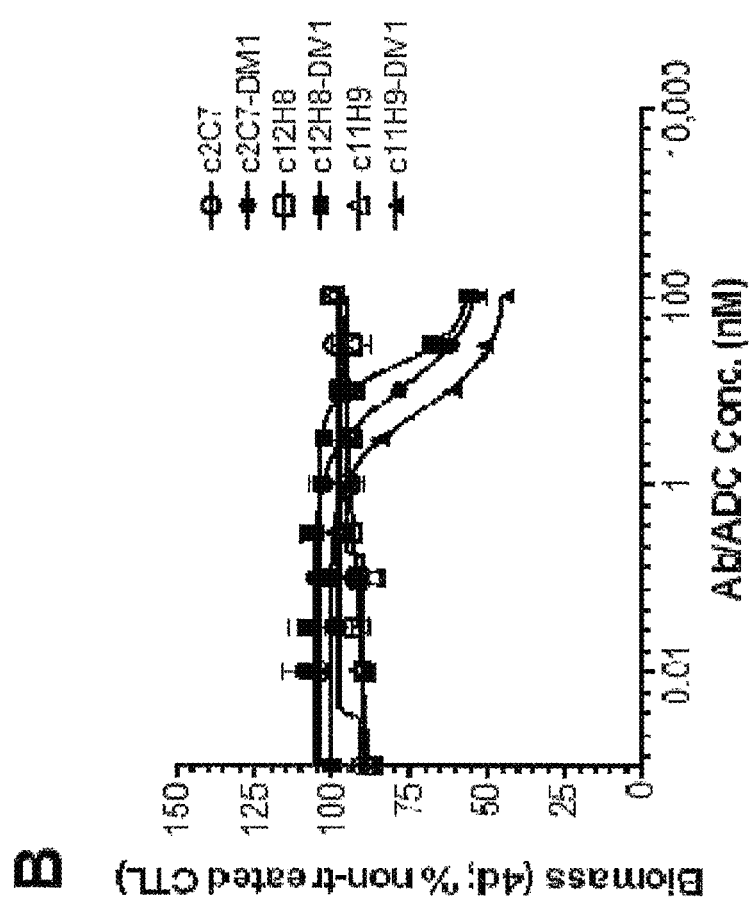

Surrogate ADC Assay:

mAb were evaluated in a surrogate ADC assay using the high hCA-IX-expressing sk-rc-52 cells. The ADC assay was carried out using a commercially available ADC kit (atsbio.com) according to the manufacturer's instructions with some modifications. Briefly, sk-rc-52 (expressing high levels of hCA-IX) and sk-rc-59 (expressing low levels of hCA-IX) cells were seeded in RPMI/5% FBS in 96-well plates at a density of 5000 and 3000 cells/well, respectively. The next day, 10 nM of mAb was mixed with 20 nM of the Mab-Zap secondary antibody from the ADC kit, incubated (30 min, RT) prior to diluting the mixture 11× in RPMI/5% cell growth medium, and 10 µL of these mixtures were added to the cells (experiment carried out in triplicate). After 72 h of incubation (37° C., 5% $CO_2$, humidified incubator), cell viability (bio mass) was determined using Sulforhodamine. For this procedure, 25 µl of 50% TCA was added to each well and plates were incubated (1 h, 4° C.). Plates were then washed 4× with tap water and air-dried at room temp. 100 µl of 0.4% (wt/vol in 1% acetic acid) SRB solution was added to each well and incubated (30 min, RT). Plates were then quickly rinsed 4× with 1% (vol/vol) acetic acid, air-dried at room temp, after which 100 µl of 10 mM Tris base solution (pH 10.5) was added followed by shaking (5 min, RT), and the OD (510 nm/540 nm) was measured. The CA-IX mouse mAb M75 was used as a positive control. Viability of the cells is expressed as the ratio of the mAb-ZAP secondary conjugate alone. Results (FIG. 17) show that mAb 12H8, 11H9 and 2C7 are either equal to or better than the M75 mAb in reducing cell viability. Next serial dilutions (0-100 nM) of recombinantly expressed c11H9, c12H8 and c2C7 were tested in the surrogate ADC assay using sk-rc-52 cells (as described above). The results (FIG. 18A; Table 12) show that the recombinantly expressed chimeric antibodies have retained their ADC potential.

ADC Assay:

Recombinantly expressed chimeric c11H9, c12H8 and c2C7 were conjugated to DM1 (mertansine). Briefly, a 10 mM stock solution of SMCC-DM1 was prepared in dimethylacetamide (DMA) and stored at −20° C. Just prior to use, stock solutions were quickly brought to room temperature and two working stocks prepared (2000 µM and 2660 µM) by diluting concentrated stock into DMA. For small-scale optimization experiments, two aliquots (100 µL) of antibody (2 mg/mL) was mixed 10 µL each of 10-fold conjugation buffer (1000 mM sodium phosphate, 200 mM NaCl, 30 mM EDTA, pH 7.2). To start the reaction, 5 µL of the appropriate working stocks were added to the appropriate tubes and mixed quickly. The reaction was allowed to proceed overnight, protected from light at 25° C. (no agitation). Reactions were stopped by passing the mixture through two desalting columns pre-equilibrated with PBS at pH 6.0, 0.02% w/v Polysorbate-20. Drug antibody ratio (DAR) was determined by UPLC-SEC using ratios of integrated absorbance at 252 nm and 280 nm vs the ratio of the extinction coefficients for the free drug and antibody at these two wavelengths. A linear relationship between DAR and the drug-linker:Ab ratio used in the reaction was determined and used to optimize the reaction ratio to achieve the target DAR of 3.5. The above protocol was repeated using the optimized drug-linker:Ab at large scale. Both the 'naked' non-conjugated c11H9, c12H8 and c2C7 and the c11H9-DM1, c12H8-DM1 and c2C7-DM1 antibodies were tested in an ADC assay (dose response 0-100 nM) using the sk-rc-52 cell line. The results (FIG. 18B, Table 12) show the specificity of these ADCs in terms of killing the cells whereas the 'naked' antibodies had no effect. These results (and the calculated $IC_{50}$) are very similar to those obtained in the surrogate ADC assay.

TABLE 12

$IC_{50}$ values for non-conjugated and DM1 conjugated chimeric anti-CA-IX antibodies.

| Construct | $IC_{50}$ (nM) |
|---|---|
| c11H9 | 6.32 |
| c11H9-DM1 | 5.84 |
| c12H8 | 23.55 |
| c12H8-DM1 | 17.88 |
| c2C7 | 2.20 |
| c2C7-DM1 | 10.11 |

Example 8: Evaluation of Cardiotoxicity in Cardiomyocytes

Both on-target and off-target toxicity relating to the drug payload carried by an ADC is critical information that needs to be evaluated early in an ADC candidate selection. Prior clinical data reported for an anti-CA-IX ADC candidate in Phase I described unresolved issues concerning cardiotoxicity. Human stem-cell derived cardiomyocytes (Cellular Dynamics; Cohen et al, 2011) from Cellular Dynamics were used to evaluate cardiotoxicity of the anti-CA-IX mAb obtained in Example 4, and their derived ADC in an in vitro setting.

Human-induced pluripotent (iPS) cardiomyocytes were obtained from Cellular Dynamics Inc. iPS cardiomyocytes (iCells) were thawed and cultured according to the manufacturers instructions. Briefly, cells were thawed, resuspended in iCell plating media, seeded in 0.1% gelatin-coated 96-well plates (15,000 cells/well) and maintained in a humidified incubator with 5% $CO_2$ at 37° C. for 4 hours. Cells were then washed to remove debris and the plating media was replaced with iCell Maintenance Media which was then changed every other day during the course of the experiment. Cells were treated 4 days post-thaw with either the unconjugated antibodies c2C7 and c12H8 or the corresponding DM1-conjugated ADCs at a concentration of 10 nM, and incubated for an additional 5 days. A non-specific negative control human IgG1 and the corresponding DM1-conjugated ADC were also used for treated the cells using the same protocol. Cell viability was measured 3 and 5 days post-treatment using the CellTiter-Glo Luminescent cell viability Assay (Promega, Madison, Wis.). Briefly, the plates and reagents were equilibrated to room temperature for 30 minutes. A volume of CellTiter-Glo reagent was added to the volume of cell culture medium present in each well and mixed on an orbital shaker for 45 minutes. The luminescence was then recorded using an EnVision plate reader (PerkinElmer Inc.)

Figure 19:
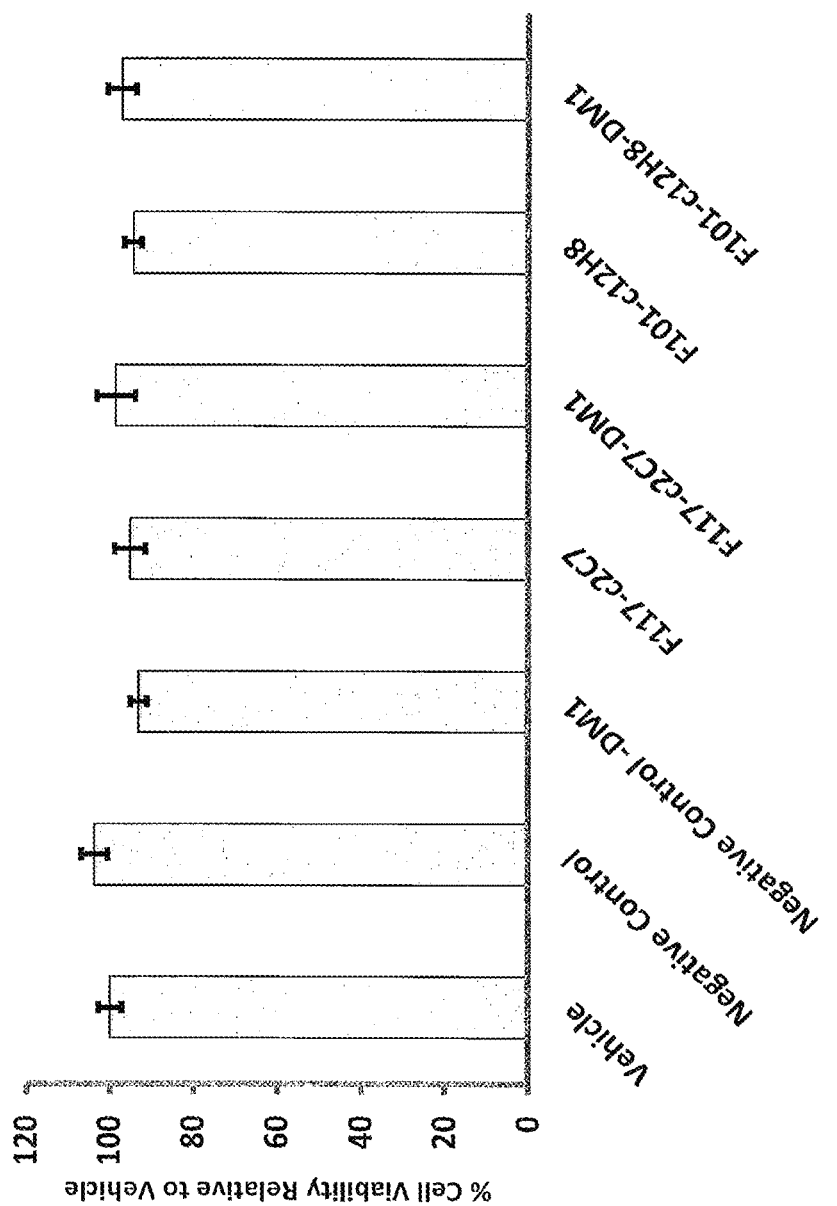
FIG. 19 is a bar graph showing results of the cardiotoxicity evaluation using the surrogate iCell-cardiomyocyte in vitro model. No significant difference in cell viability was observed with the 'naked' CA-IX antibodies or corresponding ADC tested compared to non-specific negative human IgG1 or vehicle controls.

Results are shown in FIG. 19. When compared to a non-specific human IgG1 negative control antibody and corresponding ADC, neither c2C7, c12H8 or their corresponding DM1 conjugate ADCs had any significant impact on cell viability at the concentration tested.

Example 9: CA-IX Species and CA-XII Binding by Surface Plasmon Resonance

For ADC therapeutic development, a clinically relevant non-human primate model is required to evaluate safety. Here SPR using a ProteON XPR36 instrument (BioRad) was used to measure binding of two antibodies (Example 4) to the ECD of mouse, dog and cynomolgus monkey CA-IX.

A ProteON GLC chip was activated with sEDS and sNHS prior to immobilizing approximately 4000 RUs of Goat anti-human Fc (Jackson InnumoResearch) via amine (lysine) coupling in 10 mM acetate buffer pH 4.5. This surface was then used to capture c2C7 and c12H8 on different flow cells. Recombinantly-expressed (CHO cells) SEC purified dimeric CA-IX extracellular domain (ECD) from human, mouse, dog and cynomolgus monkey and human CA-XII, were prepared in PBS with 0.02% Polysorbate-20. These dilutions were then flowed over the captured antibodies at 5 different concentrations from 100 nM to 1.23 nM using a flow rate 50 µL/min. Surfaces were regenerated after each concentration cycle using 0.85% phosphoric acid prior to the next injection. Kinetic association and dissociation rate constants were determined from non-linear fitting of the observed responses to a 1:1 binding mocel. These rate constants were used to calculate the binding constant $K_D$.

Specific binding for the purposes of evaluating the suitability of these animal models was determined as having a binding constant $K_D < 20$ nM.

TABLE 13

Selection of non-human primate models for pre-clinical toxicology. Specific binding of CA-IX antibodies to different species of CA-IX extracellular domains was measured by SPR. Specific binding was based on the criteria of having a measured $K_D < 20$ nM.

| Antibody | Human | Cynomolgus | Dog | Mouse |
|---|---|---|---|---|
| Control | Yes | Yes | No | No |
| c2C7 | Yes | Yes | No | No |
| c12H8 | Yes | Yes | No | No |

Results are shown in Table 13 and FIG. 20. Of the three species tested, cynomolgus monkey was the only one which met the affinity criteria (Table 13). Therefore, cynomolgus monkey will be the clinically-relevant non-human primate model for testing toxicology for c2C7, c12H8 and the corresponding DM1-conjugated ADC. Since CA-XII is often co-expressed with CA-IX in the same tumors, there should be no cross-reactivity between the CA-IX antibodies and CA-XII. Using SPR, there was no observable binding of any of the anti-CA-IX antibodies to CA-XII (FIG. 20).

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

LISTING OF SEQUENCES

| SEQ ID NO: | Sequence | Description |
|---|---|---|
| 1 | RASGNIHNYLA | 2C7 CDR L1 |
| 2 | NTITLAD | 2C7 CDR L2 |
| 3 | QHFWNIPFT | 2C7 CDR L3 |
| 4 | GFTFTSCYIH | 2C7 CDR H1 |
| 5 | WIYPGNGNTKYNEIFKG | 2C7 CDR H2 |
| 6 | GDTTANTMDY | 2C7 CDR H3 |
| 7 | RSSQSLVHSNGNTYLH | 11H9 CDR L1 |
| 8 | KVSNRFS | 11H9 CDR L2 |
| 9 | SQNTHVPPT | 11H9 CDR L3 |
| 10 | GFTFNTYAMY | 11H9 CDR H1 |
| 11 | RIRSKSNNYAIYYADSVKD | 11H9 CDR H2 |
| 12 | GWDWFAY | 11H9 CDR H3 |
| 13 | KSSQSLLDSDGKTYLN | 12H8 CDR L1 |
| 14 | LVSKLDS | 12H8 CDR L2 |
| 15 | CQGTHFPW | 12H8 CDR L3 |
| 16 | GYTFTNYGMN | 12H8 CDR H1 |
| 17 | WINTYTGEPTYADDFKG | 12H8 CDR H2 |
| 18 | GGIATPTSY | 12H8 CDR H3 |
| 19 | DIQMTQSPASLSASVGETVTITCRASGNIHNYLAWYQQKQGKSPQLLVYNTITLADGVPSRFSGSGSGTQYSLKINSLQPEDFGSYYCQHFWNIPFTFGAGTKLELK | mAb 2C7 VL |
| 20 | QVQLQQSGPELVKPGASVRISCKASGFTFTSCYIHWMKQRPGQGLEWIGWIYPGNGNTKYNEIFKGRATLTTDKSSSTAYMQLSSLTSEDSAVYFCARGDTTANTMDYWGQGTSVTVSS | mAb 2C7 VH |
| 21 | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQNTHVPPTFGGGTKLEIK | mAb 11H9 VL |
| 22 | EVQLVESGGRLVQPKGSLKLSCAASGFTFNTYAMYWIRQAPGKGLEWVARIRSKSNNYAIYYADSVKDRFTISRDDSQSMLYLQMNNLKTEDTAMYYCVRGWDWFAYWGQGTPVTVSA | mAb 11H9 VH |

-continued

| SEQ ID NO: | Sequence | Description |
|---|---|---|
| 23 | DVVMTQTPLTLSVTIGQPASISCKSSQSLLDSDGKTYLNWLLQRPGQ SPKRLIYLVSKLDSGVPDRFTGSGSGTDFTLKISRVEAEDLGVYYCCQ GTHFPVVTFGGGTKLEIK | mAb 12H8 VL |
| 24 | QIQLVQSGPELKKPGETVKISCKASGYTFTNYGMNVVVQQAPGKGLK WMGWINTYTGEPTYADDFKGRFAFSLETSASTAYLQINNLKNEDMAT YFCARGGIATPTSYWGQGTTLTVSS | mAb 12H8 VH |
| 25 | DIQMTQSPASLSASVGETVTITCRASGNIHNYLAWYQQKQGKSPQLL VYNTITLADGVPSRFSGSGSGTQYSLKINSLQPEDFGSYYCQHFWNI PFTFGAGTKLELKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC | Chimeric 2C7 Light chain |
| 26 | QVQLQQSGPELVKPGASVRISCKASGFTFTSCYIHWMKQRPGQGLE WIGWIYPGNGNTKYNEIFKGRATLTTDKSSSTAYMQLSSLTSEDSAV YFCARGDTTANTMDYWGQGTSVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSRDELTKNQVSLTCLVKGF YPSDIAVEWESNGQPENNYKTTPPVLDSDGSFFLYSKLTVDKSRWQ QGNVFSCSVMHEALHNHYTQKSLSLSPG | Chimeric 2C7 Heavy Chain |
| 27 | DVVMTQTPLSLPVSLGDQASISCRSSQSLVHSNGNTYLHWYLQKPG QSPKLLIYKVSNRFSGVPDRFSGSGSGTDFTLKISRVEAEDLGVYFCS QNTHVPPTFGGGTKLEIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC | Chimeric 11H9 Light Chain |
| 28 | EVQLVESGGRLVQPKGSLKLSCAASGFTFNTYAMYWIRQAPGKGLE WVARIRSKSNNYAIYYADSVKDRFTISRDDSQSMLYLQMNNLKTEDT AMYYCVRGWDWFAYWGQGTPVTVSAASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSRDELTKNQVSLTCLVKGF YPSDIAVEWESNGQPENNYKTTPPVLDSDGSFFLYSKLTVDKSRWQ QGNVFSCSVMHEALHNHYTQKSLSLSPG | Chimeric 11H9 Heavy chain |
| 29 | DVVMTQTPLTLSVTIGQPASISCKSSQSLLDSDGKTYLNWLLQRPGQ SPKRLIYLVSKLDSGVPDRFTGSGSGTDFTLKISRVEAEDLGVYYCCQ GTHFPVVTFGGGTKLEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC | Chimeric 12H8 Light Chain |
| 30 | QIQLVQSGPELKKPGETVKISCKASGYTFTNYGMNVVVQQAPGKGLK WMGWINTYTGEPTYADDFKGRFAFSLETSASTAYLQINNLKNEDMAT YFCARGGIATPTSYWGQGTTLTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVD GVEVHNAKTKPREEQYNSTYRVVSVLTVLHQDWLNGKEYKCKVSNK ALPAPIEKTISKAKGQPREPQVYTLPPSRDELTKNQVSLTCLVKGFYP SDIAVEWESNGQPENNYKTTPPVLDSDGSFFLYSKLTVDKSRWQQG NVFSCSVMHEALHNHYTQKSLSLSPG | Chimeric 12H8 Heavy chain |
| 31 | MVLQTQVFISLLLWISGAYG | Light chain signal sequence |
| 32 | MDVVTWRILFLVAAATGTHA | Heavy chain signal sequence |
| 33 | MAPLCPSPWLPLLIPAPAPGLTVQLLLSLLLLVPVHPQRLPRMQEDSP LGGGSSGEDDPLGEEDLPSEEDSPREEDPPGEEDLPGEEDLPGEED LPEVKPKSEEEGSLKLEDLPTVEAPGDPQEPQNNAHRDKEGDDQSH WRYGGDPPWPRVSPACAGRFQSPVDIRPQLAAFCPALRPLELLGFQ LPPLPELRLRNNGHSVQLTLPPGLEMALGPGREYRALQLHLHWGAA GRPGSEHTVEGHRFPAEIHVVHLSTAFARVDEALGRPGGLAVLAAFL | Recombinant hCA-IX ECD |

| SEQ ID NO: | Sequence | Description |
|---|---|---|
| | EEGPEENSAYEQLLSRLEEIAEEGSETQVPGLDISALLPSDFSRYFQY EGSLTTPPCAQGVIVVTVFNQTVMLSAKQLHTLSDTLWGPGDSRLQL NFRATQPLNGRVIEASFPAGVDSSPRAAEPVQLNSCLAAGDGSHHH HHHHHHHG | |
| 34 | EEDLPGEE | 11H9 epitope |
| 35 | LPRMQEDSPLGGG | 12H8 epitope |
| 36 | PSDFSRYFQYEGSL | Putative 2C7 epitope |
| 37 | GEEDLP | CA-IX repeat sequence |
| 38 | PQRLPRMQEDSPLGG | hCA-IX amino acid 37-51 |
| 39 | SPLGGGSSGEDDPLG | hCA-IX amino acid 47-61 |
| 40 | DDPLGEEDLPSEEDS | hCA-IX amino acid 57-71 |
| 41 | SEEDSPREEDPPGEE | hCA-IX amino acid 67-81 |
| 42 | PPGEEDLPGEEDLPG | hCA-IX amino acid 77-91 |
| 43 | EDLPGEEDLPEVKPK | hCA-IX amino acid 87-101 |
| 44 | EVKPKSEEEGSLKLE | hCA-IX amino acid 97-111 |
| 45 | SLKLEDLPTVEAPGD | hCA-IX amino acid 107-121 |
| 46 | EAPGDPQEPQNNAHR | hCA-IX amino acid 117-131 |
| 47 | QNNAHRDKEGDDQSH | hCA-IX amino acid 126-140 |
| 48 | PQRLPRMQEDSPLGGGSSGEDDPLGEEDLPSEEDS | hCA-IX amino acid 37-71 |
| 49 | SEEDSPREEDPPGEEDLPGEEDLPEVKPKSEEEGSLKLE | hCA-IX amino acid 67-111 |
| 50 | SLKLEDLPTVEAPGDPQEPQNNAHRDKEGDDQSH | hCA-IX amino acid 107-140 |
| 51 | PQRLPRMQEDSPLGGGSSGEDDPLGEEDLPSEEDSPREEDPPGEE DLPGEEDLPEVKPKSEEEGSLKLEDLPTVEAPGDPQEPQN NAHRDKEGDDQSH | hCA-IX amino acid 37-140 |
| 52 | LPRMQEDSP | 12H8 minimal epitope |
| 53 | EDLPGEED | 11H9 minimal epitope |

REFERENCES

All patents, patent applications and publications referred to throughout the application are listed below.

Abdiche Y N, Lindquist K C, Pinkerton A, Pons J, Rajpal A. Expanding the ProteOn XPR36 biosensor into a 36-ligand array expedites protein interaction analysis. Anal Biochem. 2011 Apr. 1; 411(1):139-51.

Bleumer I, Knuth A, Oosterwijk E, Hofmann R, Varga Z, Lamers C, Kruit W, Melchior S, Mala C, Ullrich S, De Mulder P, Mulders P F, Beck J. A phase II trial of chimeric monoclonal antibody G250 for advanced renal cell carcinoma patients. Br J Cancer. 2004 Mar. 8; 90(5):985-90.

Brouwers A H, van Eerd J E, Frielink C, Oosterwijk E, Oyen W J, Corstens F H, Boerman O C. Optimization of radioimmunotherapy of renal cell carcinoma: labeling of monoclonal antibody cG250 with 131I, 90Y, 177Lu, or 186Re. J Nucl Med. 2004 February; 45(2):327-37.

Chothia C, Lesk A M. Canonical structures for the hypervariable regions of immunoglobulins. J Mol Biol. 1987 Aug. 20; 196(4):901-17.

Chrastina A, Závada J, Parkkila S, Kaluz S, Kaluzova M, Rajcáni J, Pastorek J, Pastoreková S. (2003a) Biodistribution and pharmacokinetics of 125I-labeled monoclonal antibody M75 specific for carbonic anhydrase IX, an intrinsic marker of hypoxia, in nude mice xenografted with human colorectal carcinoma. Int J Cancer 105(6): 873-81.

Chrastina A, Pastoreková S, Pastorek J. (2003b) Immunotargeting of human cervical carcinoma xenograft expressing CA IX tumor-associated antigen by 125I-labeled M75 monoclonal antibody. Neoplasma 50(1):13-21.

de Kruif J, Logtenberg T. Leucine zipper dimerized bivalent and bispecific scFv antibodies from a semi-synthetic antibody phage display library. J Biol Chem. 1996 Mar. 29; 271(13):7630-4.

Dereeper A, Guignon V, Blanc G, Audic S, Buffet S, Chevenet F, Dufayard J F, Guindon S, Lefort V, Lescot M, Claverie J M, Gascuel O. Phylogeny.fr: robust phylogenetic analysis for the non-specialist. Nucleic Acids Res. 2008 Jul. 1; 36(Web Server issue):W465-9. doi: 10.1093/nar/gkn180. Epub 2008 Apr. 19.

Dereeper A, Audic S, Claverie J M, Blanc G. BLAST-EXPLORER helps you building datasets for phylogenetic analysis. BMC Evol Biol. 2010 Jan. 12; 10:8.

Ditte P, Dequiedt F, Svastova E, Hulikova A, Ohradanova-Repic A, Zatovicova M, Csaderova L, Kopacek J, Supuran C T, Pastorekova S, Pastorek J. Phosphorylation of carbonic anhydrase IX controls its ability to mediate extracellular acidification in hypoxic tumors. Cancer Res. 2011 Dec. 15; 71(24):7558-67.

Edgar R C. Local homology recognition and distance measures in linear time using compressed amino acid alphabets. Nucleic Acids Res. 2004 Jan. 16; 32(1):380-5.

Eisenberg, D., Schwarz, E., Komaromy, M., and Wall, R. Analysis of membrane and surface protein sequences with the hydrophobic moment plot. (1984) J. Mol. Biol. 179, 125-142

Feldhaus M J, Siegel R W, Opresko L K, Coleman J R, Feldhaus J M, Yeung Y A, Cochran J R, Heinzelman P, Colby D, Swers J, Graff C, Wiley H S, Wittrup K D. Flow-cytometric isolation of human antibodies from a nonimmune Saccharomyces cerevisiae surface display library. Nat Biotechnol. 2003 February; 21(2):163-70.

Fenner, L., Widmer, A. F., Goy, G., Rudin, S., and Frei, R. Rapid and reliable diagnostic algorithm for detection of Clostridium difficile. (2008) J. Clin. Microbiol. 46, 328-330.

Gietz D, St Jean A, Woods R A, Schiestl R H. Improved method for high efficiency transformation of intact yeast cells. Nucleic Acids Res. 1992 Mar. 25; 20(6):1425.

Gonzales N R, DePascalis R, Schlom J, Kashmiri S V S (2005) Tumor Biol 26, 31-43.

Hulikova A, Zatovicova M, Svastova E, Ditte P, Brasseur R, Kettmann R, Supuran C T, Kopacek J, Pastorek J, Pastorekova S. Intact intracellular tail is critical for proper functioning of the tumor-associated, hypoxia-regulated carbonic anhydrase IX. FEBS Lett. 2009 Nov. 19; 583 (22):3563-8.

Jones P T, Dear P H, Foote J, Neuberger M S, Winter G (1986) Nature 321, 522-525.

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19

Lefranc M P, Pommie C, Ruiz M, Giudicelli V, Foulquier E, Truong L, Thouvenin-Contet V, Lefranc G. IMGT unique numbering for immunoglobulin and T cell receptor variable domains and Ig superfamily V-like domains. Dev Comp Immunol. 2003 January; 27(1):55-77. Review.

Liao-Chan S, Daine-Matsuoka B, Heald N, Wong T., Lin T, Cai A G, Lai M, D'Alessio J A, Theunissen J-W (2015) Quantitative assessment of antibody internalization with novel nomoclonal antibodies against Alexa fluorophores. PLoS ONE 10(4): e0124708. doi:10.1371/journal.pone.0124708

Lou Y, McDonald P C, Oloumi A, Chia S, Ostlund C, Ahmadi A, Kyle A, Auf dem Keller U, Leung S, Huntsman D, Clarke B, Sutherland B W, Waterhouse D, Bally M, Roskelley C, Overall C M, Minchinton A, Pacchiano F, Carta F, Scozzafava A, Touisni N, Winum J Y, Supuran C T, Dedhar S. Targeting tumor hypoxia: suppression of breast tumor growth and metastasis by novel carbonic anhydrase IX inhibitors. Cancer Res. 2011 May 1; 71(9): 3364-76. Erratum in: Cancer Res. 2011 Jun. 15; 71(12): 4325. Cancer Res. 2011 Jul. 1; 71(13):4733.

Musher, D. M., Manhas, A., Jain, P., Nuila, F., Waqar, A., Logan, N., Marino, B., Graviss, E. A. Detection of Clostridium difficile toxin: comparison of enzyme immunoassay results with results obtained by cytotoxicity assay. (2007) J. Clin. Microbiol. 45, 2737-2739.

Nielsen U B, Adams G P, Weiner L M, Marks J D. Targeting of bivalent anti-ErbB2 diabody antibody fragments to tumor cells is independent of the intrinsic antibody affinity. Cancer Res. 2000 Nov. 15; 60(22):6434-40.

Neri D, Supuran C T. Interfering with pH regulation in tumours as a therapeutic strategy. Nat Rev Drug Discov. 2011 Sep. 16; 10(10):767-77. doi: 10.1038/nrd3554. Review.

Nicaise M, Valeio-Lepiniec M, Minard P, Desmadril M. (2004) Affinity transfer by CDR grafting on a nonimmunoglobulin scaffold. Protein Sci. 13(7): 1882-1891.

Oosterwijk E, Ruiter D J, Wakka J C, Huiskens-van der Meij J W, Jonas U, Fleuren G J, Zwartendijk J, Hoedemaeker P, Warnaar S O. Immunohistochemical analysis of monoclonal antibodies to renal antigens. Application in the diagnosis of renal cell carcinoma. Am J Pathol. 1986 May; 123(2):301-9.

Oosterwijk E, Boerman O C, Oyen W J, Old L J, Mulders P F. Antibody therapy in renal cell carcinoma. World J Urol. 2008 April; 26(2):141-6. doi: 10.1007/s00345-008-0236-5. Epub 2008 Feb. 1. Review.

Pacchiano F, Carta F, Vullo D, Scozzafava A, Supuran C T. Inhibition of β-carbonic anhydrases with ureido-substituted benzenesulfonamides. Bioorg Med Chem Lett. 2011 Jan. 1; 21(1):102-5. doi: 10.1016/j.bmcl.2010.11.064

Padlan E A (1991) A possible procedure for reducing the immunogenicity of antibody variable domains while preserving their ligand-binding properties. Mol Immunol 28, 489-498.

Pastorekova S, Parkkila S, Pastorek J, Supuran C T. Carbonic anhydrases: current state of the art, therapeutic applications and future prospects. J Enzyme Inhib Med Chem. 2004 June; 19(3):199-229. Review.

Petrul H M, Schatz C A, Kopitz C C, Adnane L, McCabe T J, Trail P, Ha S, Chang Y S, Voznesensky A, Ranges G, Tamburini P P. Therapeutic mechanism and efficacy of the antibody-drug conjugate BAY 79-4620 targeting human carbonic anhydrase 9. Mol Cancer Ther. 2012 February; 11 (2):340-9. doi: 10.1158/1535-7163.MCT-11-0523. Epub 2011 Dec. 6.

Planche, T., Aghaizu, A., Holliman, R., Riley, P., Poloniecki, J., Breathnach, A., and Krishna, S. (2008) Diagnosis of Clostridium difficile infection by toxin detection kits: a systematic review. Lancet Infect. Dis. 8, 777-784. Ridgway, J. B., Presta, L. G., and Carter, P. 'Knobs-into-holes' engineering of antibody CH3 domains for heavy chain heterodimerization. (1996) Protein Eng. 9, 617-621.

Queen C, Schneider W P, Selick H E, Payne P W, Landolfi N F, Duncan J F, Avdalovic N M, Levitt M, Junghans R P, Waldmann T A (1989) Proc Natl Acad Sci USA 86, 10029-10033.

Riechmann L, Clark M, Waldmann H, Winter G (1988) Nature 332, 323-327.

Rüssmann, H., Panthel, K., Bader, R. C., Schmitt, C., and Schaumann, R. Evaluation of three rapid assays for detection of Clostridium difficile toxin A and toxin B in stool specimens. (2007) Eur. J. Clin. Microbiol. Infect. Dis. 26, 115-119.

Sloan, L. M., Duresko, B. J., Gustafson, D. R., and Rosenblatt, J. E. Comparison of real-time PCR for detection of the tcdC gene with four toxin immunoassays and culture in diagnosis of Clostridium difficile infection. (2008) J. Clin. Microbiol. 46, 1996-2001.

Stillebroer A B, Boerman O C, Desar I M, Boers-Sonderen M J, van Herpen C M, Langenhuijsen J F, Smith-Jones P M, Oosterwijk E, Oyen W J, Mulders P F. Phase 1 radioimmunotherapy study with lutetium 177-labeled anti-carbonic anhydrase IX monoclonal antibody girentuximab in patients with advanced renal cell carcinoma. Eur Urol. 2013 September; 64(3):478-85. doi: 10.1016/j.eururo.2012.08.024. Epub 2012 Aug. 21.

Supuran C T. Diuretics: from classical carbonic anhydrase inhibitors to novel applications of the sulfonamides. Curr Pharm Des. 2008; 14(7):641-8. Review.

Surfus J E, Hank J A, Oosterwijk E, Welt S, Lindstrom M J, Albertini M R, Schiller J H, Sondel P M. Anti-renal-cell carcinoma chimeric antibody G250 facilitates antibody-dependent cellular cytotoxicity with in vitro and in vivo interleukin-2-activated effectors. J Immunother Emphasis Tumor Immunol. 1996 May; 19(3):184-91.

Svastova E, Witarski W, Csaderova L, Kosik I, Skvarkova L, Hulikova A, Zatovicova M, Barathova M, Kopacek J, Pastorek J, Pastorekova S. Carbonic anhydrase IX interacts with bicarbonate transporters in lamellipodia and increases cell migration via its catalytic domain. J Biol Chem. 2012 Jan. 27; 287(5):3392-402. doi: 10.1074/jbc.M111.286062. Epub 2011 Dec. 14.

Tempest P R, Bremmer P, Lambert M, Taylor G, Furze J M, Carr F J, Harris W J (1991) Biotechnology 9, 266-271.

Thiry A, Dogné J M, Masereel B, Supuran C T. Targeting tumor-associated carbonic anhydrase IX in cancer therapy. Trends Pharmacol Sci. 2006 November; 27(11): 566-73. Epub 2006 Sep. 25.

Tsurushita N, Hinton, R P, Kumar S (2005) Design of humanized antibodies: From anti-Tac to Zenapax. Methods 36, 69-83.

Turgeon, D. K., Novicki, T. J., Quick, J., Carlson, L., Miller, P., Ulness, B., Cent, A., Ashley, R., Larson, A., Coyle, M., Limaye, A. P., Cookson, B. T., and Fritsche, T. R. Six rapid tests for direct detection of Clostridium difficile and its toxins in fecal samples compared with the fibroblast cytotoxicity assay. (2003) J. Clin. Microbiol. 41, 667-670.

Wykoff C C, Beasley N J, Watson P H, Turner K J, Pastorek J, Sibtain A, Wilson G D, Turley H, Talks K L, Maxwell P H, Pugh C W, Ratcliffe P J, Harris A L. Hypoxia-inducible expression of tumor-associated carbonic anhydrases. Cancer Res. 2000 Dec. 15; 60(24):7075-83.

Zatovicova M, Sedlakova O, Svastova E, Ohradanova A, Ciampor F, Arribas J, Pastorek J, Pastorekova S. Ectodomain shedding of the hypoxia-induced carbonic anhydrase IX is a metalloprotease-dependent process regulated by TACE/ADAM17. Br J Cancer. 2005 Nov. 28; 93(11): 1267-76.

Zatovicova M, Jelenska L, Hulikova A, Csaderova L, Ditte Z, Ditte P, Goliasova T, Pastorek J, Pastorekova S. (2010) Carbonic anhydrase IX as an anticancer therapy target: preclinical evaluation of internalizing monoclonal antibody directed to catalytic domain. Curr Pharm Des. 16(29):3255-63.

Pastoreková SPastoreková S, Závadová Z, Kostál M, Babusiková O, Závada J. A novel quasi-viral agent, MaTu, is a two-component system. Virology. 1992 April; 187(2):620-6.

Závada J, Závadová Z, Pastorek J, Biesová Z, Jezek J, Velek J. Human tumour-associated cell adhesion protein MN/CA IX: identification of M75 epitope and of the region mediating cell adhesion. Br J Cancer. 2000 June; 82(11):1808-13.

Zhang, J., Tanha, J., Hirama, T., Khiew, N. H., To, R., Tong-Sevinc, H., Stone, E., Brisson, J. R., and MacKenzie, C. R. A pentavalent single-domain antibody approach to tumor antigen discovery and the development of novel proteomics reagents. (2004b) J. Mol. Biol. 335, 49-56.

Zhu X, Wang L, Liu R, Flutter B, Li S, Ding J, Tao H, Liu C, Sun M, Gao B. COMBODY: one-domain antibody multimer with improved avidity. Immunol Cell Biol. 2010 August; 88(6):667-75. doi: 10.1038/icb.2010.21. Epub 2010 Mar. 9. European Patent No. 519596

WO 95/04069

WO/2004/076670

WO2003/046560

The invention claimed is:

1. An isolated or purified antibody or antigen-binding fragment thereof, comprising a) a light chain comprising a complementarity determining region (CDR) L1 sequence selected from the group consisting of:

RASGNIHNYLA; (SEQ ID NO: 1)

RSSQSLVHSNGNTYLH; (SEQ ID NO: 7)
and

KSSQSLLDSDGKTYLN, (SEQ ID NO: 13)

a CDR L2 sequence selected from the group consisting of:

NTITLAD; (SEQ ID NO: 2)

KVSNRFS; (SEQ ID NO: 8)
and

LVSKLDS, (SEQ ID NO: 14)

and
a CDR L3 sequence selected from the group consisting of:

QHFWNIPFT; (SEQ ID NO: 3)

SQNTHVPPT; (SEQ ID NO: 9)
and

CQGTHFPW, (SEQ ID NO: 15)

and
b) a heavy chain comprising a complementarity determining region (CDR) H1 sequence selected from the group consisting of:

GFTFTSCYIH; (SEQ ID NO: 4)

GFTFNTYAMY; (SEQ ID NO: 10)
and

GYTFTNYGMN, (SEQ ID NO: 16)

a CDR H2 sequence selected from the group consisting of:

WIYPGNGNTKYNEIFKG; (SEQ ID NO: 5)

RIRSKSNNYAIYYADSVKD; (SEQ ID NO: 11)
and

WINTYTGEPTYADDFKG, (SEQ ID NO: 17)

and
a CDR H3 sequence selected from the group consisting of:

GDTTANTMDY; (SEQ ID NO: 6)

GWDWFAY; (SEQ ID NO: 12)
and

GGIATPTSY, (SEQ ID NO: 18)

wherein the antibody or antigen-binding fragment thereof specifically binds the extracellular domain of Carbohydrate Anhydrase IX.

2. The isolated or purified antibody or antigen-binding fragment thereof of claim 1, wherein the antibody or antigen-binding fragment thereof is selected from the group consisting of:
- a) a light chain comprising CDR L1 of sequence RASGNIHNYLA (SEQ ID NO:1), CDR L2 of sequence NTITLAD (SEQ ID NO:2), and CDR L3 of sequence QHFWNIPFT (SEQ ID NO:3); and a heavy chain comprising CDR H1 of sequence GFTFTSCYIH (SEQ ID NO:4), CDR H2 of sequence WIYPGNGNTKYNEIFKG (SEQ ID NO:5), and CDR H3 of sequence GDTTANTMDY (SEQ ID NO:6); and wherein the antibody or antigen-binding fragment thereof binds the catalytic domain of CA-IX;
- b) a light chain comprising CDR L1 of sequence RSSQSLVHSNGNTYLH (SEQ ID NO:7), CDR L2 of sequence KVSNRFS (SEQ ID NO:8), CDRL3 of sequence SQNTHVPPT (SEQ ID NO:9); and a heavy chain comprising CDR H1 of sequence GFTFNTYAMY (SEQ ID NO:10), CDR H2 of sequence RIRSKSNNYAIYYADSVKD (SEQ ID NO:11), and CDR H3 of sequence GWDWFAY(SEQ ID NO:12); and wherein the antibody or antigen-binding fragment thereof binds the PG-like domain of CA-IX; and
- c) a light chain comprising CDR L1 of sequence KSSQSLLDSDGKTYLN (SEQ ID NO:13), CDR L2 of sequence LVSKLDS (SEQ ID NO:14), CDRL3 of sequence CQGTHFPW (SEQ ID NO:15); and a heavy chain comprising CDR H1 of sequence GYTFTNYGMN (SEQ ID NO:16), CDR H2 of sequence WINTYTGEPTYADDFKG (SEQ ID NO:17), and CDR H3 of sequence GGIATPTSY (SEQ ID NO:18); and wherein the antibody or antigen-binding fragment thereof binds the PG-like domain of CA-IX.

3. An isolated or purified antibody or antigen-binding fragment thereof, comprising:
- a) a variable light (VL) domain of sequence selected from the group consisting of:

```
                                           (SEQ ID NO: 19)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELK, (SEQ ID NO: 21)
DVVMTQTPLSLPVSLGDQASISCRSSQSLVHSNGNTYLHWYLQKPGQSPK

WYKVSNRFSGVPDRFSGSGSGTDFTLKISRVEAEDLGVYFCSQNTHVPPT

FGGGTKLEIK,
and (SEQ ID NO: 23)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCCQGTHFP

WTFGGGTKLEIK;
``` and
- b) a variable heavy (V$_H$) domain of sequence selected from the group consisting of:

```
                                           (SEQ ID NO: 20)
QVQLQQSGPELVKPGASVRISCKASGFTFTSCYIHWMKQRPGQGLEWIGW

IYPGNGNTKYNEIFKGRATLTTDKSSSTAYMQLSSLTSEDSAVYFCARGD

TTANTMDYWGQGTSVTVSS;

(SEQ ID NO: 22)
EVQLVESGGRLVQPKGSLKLSCAASGFTFNTYAMYWIRQAPGKGLEWVAR

IRSKSNNYAIYYADSVKDRFTISRDDSQSMLYLQMNNLKTEDTAMYYCVR

GWDWFAYWGQGTPVTVSA;
and (SEQ ID NO: 24)
QIQLVQSGPELKKPGETVKISCKASGYTFTNYGMNWVQQAPGKGLKWMGW

INTYTGEPTYADDFKGRFAFSLETSASTAYLQINNLKNEDMATYFCARGG

IATPTSYWGQGTTLTVSS;
``` wherein the antibody or antigen-binding fragment thereof specifically binds to the extracellular domain of CA-IX.

4. The isolated or purified antibody or antigen-binding fragment thereof of claim 1, wherein the isolated or purified antibody or antigen-binding fragment thereof comprises
- a) a variable light (VL) domain of sequence

```
                                           (SEQ ID NO: 19)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELK
``` and a variable heavy (V$_H$) domain of sequence

```
                                           (SEQ ID NO: 20)
QVQLQQSGPELVKPGASVRISCKASGFTFTSCYIHWMKQRPGQGLEWIGW

IYPGNGNTKYNEIFKGRATLTTDKSSSTAYMQLSSLTSEDSAVYFCARGD

TTANTMDYWGQGTSVTVSS;
```

- b) a variable light (V$_L$) domain of sequence

```
                                           (SEQ ID NO: 21)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQNTHVP

PTFGGGTKLEIK
``` and a variable heavy (V$_H$) domain of sequence

```
                                           (SEQ ID NO: 22)
EVQLVESGGRLVQPKGSLKLSCAASGFTFNTYAMYWIRQAPGKGLEWVAR

IRSKSNNYAIYYADSVKDRFTISRDDSQSMLYLQMNNLKTEDTAMYYCVR

GWDWFAYWGQGTPVTVSA;
``` or
- c) a variable light (V$_L$) domain of sequence

```
                                           (SEQ ID NO: 23)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCCQGTHFP

WTFGGGTKLEIK
``` and a variable heavy (V_H) domain of sequence (SEQ ID NO: 24)
QIQLVQSGPELKKPGETVKISCKASGYTFTNYGMNWVQQAPGKGLKWMGW

INTYTGEPTYADDFKGRFAFSLETSASTAYLQINNLKNEDMATYFCARGG

IATPTSYWGQGTTLTVSS.

5. The isolated or purified antibody or antigen-binding fragment thereof claim 1, wherein the antibody or antigen-binding fragment thereof is a full-length IgG, Fv, scFv, Fab, or F(ab')₂, or wherein the antibody or antigen-binding fragment thereof comprises framework regions from IgA, IgD, IgE, IgG, or IgM.

6. The isolated or purified antibody or antigen-binding fragment thereof of claim 1, wherein the antibody or antigen-binding fragment thereof is chimeric.

7. The isolated or purified antibody or antigen-binding fragment thereof of claim 6, wherein the chimeric antibody or antigen-binding fragment thereof comprises constant regions from human IgG1, or wherein the chimeric antibody or antigen-binding fragment thereof comprises constant regions from human kappa 1 light chain and human IgG1 heavy chain.

8. The isolated or purified antibody or antigen-binding fragment thereof of claim 7, wherein the isolated or purified antibody or antigen-binding fragment thereof comprises a) a variable light (V_L) domain comprising the sequence (SEQ ID NO: 25)
DIQMTQSPASLSASVGETVTITCRASGNIHNYLAWYQQKQGKSPQLLVYN

TITLADGVPSRFSGSGSGTQYSLKINSLQPEDFGSYYCQHFWNIPFTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC and a variable heavy (V_H) domain comprising the sequence (SEQ ID NO: 26)
QVQLQQSGPELVKPGASVRISCKASGFTFTSCYIHWMKQRPGQGLEWIGW

IYPGNGNTKYNEIFKGRATLTTDKSSSTAYMQLSSLTSEDSAVYFCARGD

TTANTMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG;

b) a variable light (V_L) domain comprising the sequence (SEQ ID NO: 27)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQNTHVP

PTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC and a variable heavy (V_H) domain comprising the sequence (SEQ ID NO: 28)
EVQLVESGGRLVQPKGSLKLSCAASGFTFNTYAMYWIRQAPGKGLEWVAR

IRSKSNNYAIYYADSVKDRFTISRDDSQSMLYLQMNNLKTEDTAMYYCVR

GWDWFAYWGQGTPVTVSAASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG;
or c) a variable light (V_L) domain comprising the sequence (SEQ ID NO: 29)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCCQGTHFP

WTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC and a variable heavy (V_H) domain comprising the sequence (SEQ ID NO: 30)
QIQLVQSGPELKKPGETVKISCKASGYTFTNYGMNWVQQAPGKGLKWMGW

INTYTGEPTYADDFKGRFAFSLETSASTAYLQINNLKNEDMATYFCARGG

IATPTSYWGQGTTLTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG.

9. The isolated or purified antibody or antigen-binding fragment thereof of claim 1, wherein the antibody or antigen-binding fragment thereof is immobilized onto a surface, or wherein the antibody or antigen-binding fragment thereof is linked to a cargo molecule.

10. The isolated or purified antibody or antigen-binding fragment thereof of claim 9, wherein the cargo molecule is a detectable agent, a therapeutic agent, a drug, a peptide, an enzyme, a growth factor, a cytokine, a receptor trap, an antibody or antigen-binding fragment thereof, a chemical compound, a carbohydrate moiety, DNA-based molecules, a cytotoxic agent, viral vector, one or more liposomes or nanocarriers loaded with any of the previously recited types of cargo molecules, or one or more nanoparticle, nanowire, nanotube, or quantum dots.

11. A composition comprising one or more than one isolated or purified antibody or antigen-binding fragment thereof of claim 1 and a pharmaceutically-acceptable carrier, diluent, or excipient.

12. An in vitro method of detecting CA-IX, comprising
   a) contacting a tissue sample with one or more than one isolated or purified antibody or antigen-binding fragment thereof of claim 1 linked to a detectable agent; and
   b) detecting the detectable agent linked to the antibody or antigen-binding fragment thereof bound to CA-IX in the tissue sample.

13. The method of claim 12, wherein method detects CA-IX in circulating cells and the sample is a serum sample.

14. The method of claim 12, wherein the step of detecting (step b)) is performed using optical imaging, immunohistochemistry, molecular diagnostic imaging, enzyme-linked immunosorbent assay (ELISA).

15. An in vivo method of detecting CA-IX expression in a subject, comprising:
   a) administering one or more than one isolated or purified antibody or antigen-binding fragment thereof of claim 1 linked to a detectable agent to the subject; and
   b) detecting the detectable agent linked to the antibody or antigen-binding fragment thereof bound to CA-IX.

16. A method of transporting a molecule of interest into cells expressing CA-IX, comprising administering one or more than one isolated or purified antibody or antigen-binding fragment thereof of claim 1 linked to the molecule of interest to a subject, wherein the one or more than one isolated or purified antibody or fragment thereof delivers the molecule of interest to the subject's cells expressing CA-IX.

17. The method of claim 16, wherein the step of detecting (step b)) is performed using positron emission tomography (PET), single photon emission computed tomography (SPECT), fluorescence imaging.

18. The method of claim 16, wherein the molecule of interest is selected from the group consisting of a detectable agent, a therapeutic agent, a drug, a peptide, an enzyme, a growth factor, a cytokine, a receptor trap, an antibody or antigen-binding fragment thereof, a chemical compound, a carbohydrate moiety, DNA-based molecules, a cytotoxic agent, viral vector, one or more liposomes or nanocarriers loaded with any of the previously recited types of cargo molecules, or one or more nanoparticle, nanowire, nanotube, or quantum dots.

* * * * *

SEQUENCE LISTING

<160> NUMBER OF SEQ ID NOS: 53

<210> SEQ ID NO 1
<211> LENGTH: 11
<212> TYPE: PRT
<213> ORGANISM: Artificial Sequence
<220> FEATURE:
<223> OTHER INFORMATION: 2C7 CDR L1

<400> SEQUENCE: 1

Arg Ala Ser Gly Asn Ile His Asn Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: 2C7 CDR L2

<400> SEQUENCE: 2

Asn Thr Ile Thr Leu Ala Asp
1               5

<210> SEQ ID NO 3
<211> LENGTH: 9
<212> TYPE: PRT
<213> ORGANISM: Artificial Sequence
<220> FEATURE:
<223> OTHER INFORMATION: 2C7 CDR L3

<400> SEQUENCE: 3

Gln His Phe Trp Asn Ile Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: 2C7 CDR H1

<400> SEQUENCE: 4

Gly Phe Thr Phe Thr Ser Cys Tyr Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: 2C7 CDR H2

<400> SEQUENCE: 5

Trp Ile Tyr Pro Gly Asn Gly Asn Thr Lys Tyr Asn Glu Ile Phe Lys
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: 2C7 CDR H3

<400> SEQUENCE: 6

Gly Asp Thr Thr Ala Asn Thr Met Asp Tyr
1               5                   10

<210> SEQ ID NO 7
<211> LENGTH: 16
<212> TYPE: PRT
<213> ORGANISM: Artificial Sequence
<220> FEATURE:
<223> OTHER INFORMATION: 11H9 CDR L1

<400> SEQUENCE: 7

Arg Ser Ser Gln Ser Leu Val His Ser Asn Gly Asn Thr Tyr Leu His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: 11H9 CDR L2

<400> SEQUENCE: 8

Lys Val Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: 11H9 CDR L3

<400> SEQUENCE: 9

Ser Gln Asn Thr His Val Pro Pro Thr
1               5

<210> SEQ ID NO 10
<211> LENGTH: 10
<212> TYPE: PRT
<213> ORGANISM: Artificial Sequence
<220> FEATURE:
<223> OTHER INFORMATION: 11H9 CDR H1

<400> SEQUENCE: 10

Gly Phe Thr Phe Asn Thr Tyr Ala Met Tyr
1               5                   10

<210> SEQ ID NO 11
<211> LENGTH: 19
<212> TYPE: PRT
<213> ORGANISM: Artificial Sequence
<220> FEATURE:
<223> OTHER INFORMATION: 11H9 CDR H2

<400> SEQUENCE: 11

Arg Ile Arg Ser Lys Ser Asn Asn Tyr Ala Ile Tyr Tyr Ala Asp Ser
1               5                   10                  15

Val Lys Asp

<210> SEQ ID NO 12
<211> LENGTH: 7
<212> TYPE: PRT
<213> ORGANISM: Artificial Sequence
<220> FEATURE:
<223> OTHER INFORMATION: 11H9 CDR H3

<400> SEQUENCE: 12

```
Gly Trp Asp Trp Phe Ala Tyr
1               5

<210> SEQ ID NO 13
<211> LENGTH: 16
<212> TYPE: PRT
<213> ORGANISM: Artificial Sequence
<220> FEATURE:
<223> OTHER INFORMATION: 12H8 CDR L1

<400> SEQUENCE: 13

Lys Ser Ser Gln Ser Leu Leu Asp Ser Asp Gly Lys Thr Tyr Leu Asn
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: 12H8 CDR L2

<400> SEQUENCE: 14

Leu Val Ser Lys Leu Asp Ser
1               5

<210> SEQ ID NO 15
<211> LENGTH: 8
<212> TYPE: PRT
<213> ORGANISM: Artificial Sequence
<220> FEATURE:
<223> OTHER INFORMATION: 12H8 CDR L3

<400> SEQUENCE: 15

Cys Gln Gly Thr His Phe Pro Trp
1               5

<210> SEQ ID NO 16
<211> LENGTH: 10
<212> TYPE: PRT
<213> ORGANISM: Artificial Sequence
<220> FEATURE:
<223> OTHER INFORMATION: 12H8 CDR H1

<400> SEQUENCE: 16

Gly Tyr Thr Phe Thr Asn Tyr Gly Met Asn
1               5                   10

<210> SEQ ID NO 17
<211> LENGTH: 17
<212> TYPE: PRT
<213> ORGANISM: Artificial Sequence
<220> FEATURE:
<223> OTHER INFORMATION: 12H8 CDR H2

<400> SEQUENCE: 17

Trp Ile Asn Thr Tyr Thr Gly Glu Pro Thr Tyr Ala Asp Asp Phe Lys
1               5                   10                  15

Gly

<210> SEQ ID NO 18
<211> LENGTH: 9
<212> TYPE: PRT
<213> ORGANISM: Artificial Sequence
<220> FEATURE:
<223> OTHER INFORMATION: 12H8 CDR H3
```

<400> SEQUENCE: 18

Gly Gly Ile Ala Thr Pro Thr Ser Tyr
1               5

<210> SEQ ID NO 19
<211> LENGTH: 107
<212> TYPE: PRT
<213> ORGANISM: Artificial Sequence
<220> FEATURE:
<223> OTHER INFORMATION: mAb 2C7 VL

<400> SEQUENCE: 19

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Thr Ile Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Asn Ile Pro Phe
                85                  90                  95

Thr Phe Gly Ala Gly Thr Lys Leu Glu Leu Lys
            100                 105

<210> SEQ ID NO 20
<211> LENGTH: 119
<212> TYPE: PRT
<213> ORGANISM: Artificial Sequence
<220> FEATURE:
<223> OTHER INFORMATION: mAb 2C7 VH

<400> SEQUENCE: 20

Gln Val Gln Leu Gln Gln Ser Gly Pro Glu Leu Val Lys Pro Gly Ala
1               5                   10                  15

Ser Val Arg Ile Ser Cys Lys Ala Ser Gly Phe Thr Phe Thr Ser Cys
                20                  25                  30

Tyr Ile His Trp Met Lys Gln Arg Pro Gly Gln Gly Leu Glu Trp Ile
            35                  40                  45

Gly Trp Ile Tyr Pro Gly Asn Gly Asn Thr Lys Tyr Asn Glu Ile Phe
        50                  55                  60

Lys Gly Arg Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asp Thr Thr Ala Asn Thr Met Asp Tyr Trp Gly Gln Gly
            100                 105                 110

Thr Ser Val Thr Val Ser Ser
        115

<210> SEQ ID NO 21
<211> LENGTH: 112
<212> TYPE: PRT
<213> ORGANISM: Artificial Sequence
<220> FEATURE:
<223> OTHER INFORMATION: mAb 11H9 VL

<400> SEQUENCE: 21

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
                35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Gly Gly Thr Lys Leu Glu Ile Lys
                100                 105                 110
```

<210> SEQ ID NO 22
<211> LENGTH: 118
<212> TYPE: PRT
<213> ORGANISM: Artificial Sequence
<220> FEATURE:
<223> OTHER INFORMATION: mAb 11H9 VH

<400> SEQUENCE: 22

```
Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
                35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Trp Asp Trp Phe Ala Tyr Trp Gly Gln Gly Thr
                100                 105                 110

Pro Val Thr Val Ser Ala
        115
```

<210> SEQ ID NO 23
<211> LENGTH: 112
<212> TYPE: PRT
<213> ORGANISM: Artificial Sequence
<220> FEATURE:
<223> OTHER INFORMATION: mAb 12H8 VL

<400> SEQUENCE: 23

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
                35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
```

```
                65                  70                  75                  80
Ser Arg Val Glu Ala Glu Asp Leu Gly Val Tyr Tyr Cys Cys Gln Gly
                    85                  90                  95

Thr His Phe Pro Trp Thr Phe Gly Gly Gly Thr Lys Leu Glu Ile Lys
                100                 105                 110

<210> SEQ ID NO 24
<211> LENGTH: 118
<212> TYPE: PRT
<213> ORGANISM: Artificial Sequence
<220> FEATURE:
<223> OTHER INFORMATION: mAb 12H8 VH

<400> SEQUENCE: 24

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Gly Ile Ala Thr Pro Thr Ser Tyr Trp Gly Gln Gly Thr
                100                 105                 110

Thr Leu Thr Val Ser Ser
            115

<210> SEQ ID NO 25
<211> LENGTH: 214
<212> TYPE: PRT
<213> ORGANISM: Artificial Sequence
<220> FEATURE:
<223> OTHER INFORMATION: Chimeric 2C7 Light chain

<400> SEQUENCE: 25

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Thr Ile Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Asn Ile Pro Phe
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 26
<211> LENGTH: 448
<212> TYPE: PRT
<213> ORGANISM: Artificial Sequence
<220> FEATURE:
<223> OTHER INFORMATION: Chimeric 2C7 Heavy Chain

<400> SEQUENCE: 26

```
Gln Val Gln Leu Gln Gln Ser Gly Pro Glu Leu Val Lys Pro Gly Ala
1               5                   10                  15

Ser Val Arg Ile Ser Cys Lys Ala Ser Gly Phe Thr Phe Thr Ser Cys
            20                  25                  30

Tyr Ile His Trp Met Lys Gln Arg Pro Gly Gln Gly Leu Glu Trp Ile
        35                  40                  45

Gly Trp Ile Tyr Pro Gly Asn Gly Asn Thr Lys Tyr Asn Glu Ile Phe
    50                  55                  60

Lys Gly Arg Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asp Thr Thr Ala Asn Thr Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 27
<211> LENGTH: 219
<212> TYPE: PRT
<213> ORGANISM: Artificial Sequence
<220> FEATURE:
<223> OTHER INFORMATION: Chimeric 11H9 Light Chain

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 28
<211> LENGTH: 447
<212> TYPE: PRT
<213> ORGANISM: Artificial Sequence
<220> FEATURE:
<223> OTHER INFORMATION: Chimeric 11H9 Heavy chain

<400> SEQUENCE: 28

```
Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Trp Asp Trp Phe Ala Tyr Trp Gly Gln Gly Thr
            100                 105                 110

Pro Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
            435                 440                 445
```

<210> SEQ ID NO 29
<211> LENGTH: 219
<212> TYPE: PRT
<213> ORGANISM: Artificial Sequence
<220> FEATURE:
<223> OTHER INFORMATION: Chimeric 12H8 Light Chain

<400> SEQUENCE: 29

```
Asp Val Val Met Thr Gln Thr Pro Leu Thr Leu Ser Val Thr Ile Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Cys Gln Gly
                85                  90                  95
Thr His Phe Pro Trp Thr Phe Gly Gly Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 30
<211> LENGTH: 447
<212> TYPE: PRT
<213> ORGANISM: Artificial Sequence
<220> FEATURE:
<223> OTHER INFORMATION: Chimeric 12H8 Heavy chain

<400> SEQUENCE: 30

-continued

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Gly Ile Ala Thr Pro Thr Ser Tyr Trp Gly Gln Gly Thr
                100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
        435                 440                 445

<210> SEQ ID NO 31
<211> LENGTH: 20
<212> TYPE: PRT
<213> ORGANISM: Artificial Sequence
<220> FEATURE:
<223> OTHER INFORMATION: Light chain signal sequence

<400> SEQUENCE: 31

Met Val Leu Gln Thr Gln Val Phe Ile Ser Leu Leu Trp Ile Ser
 1               5                  10                  15

Gly Ala Tyr Gly
            20

<210> SEQ ID NO 32
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 32

Met Asp Trp Thr Trp Arg Ile Leu Phe Leu Val Ala Ala Thr Gly
 1               5                  10                  15

Thr His Ala

<210> SEQ ID NO 33
<211> LENGTH: 427
<212> TYPE: PRT
<213> ORGANISM: Artificial Sequence
<220> FEATURE:
<223> OTHER INFORMATION: Recombinant hCA-IX ECD

<400> SEQUENCE: 33

Met Ala Pro Leu Cys Pro Ser Pro Trp Leu Pro Leu Leu Ile Pro Ala
 1               5                  10                  15

Pro Ala Pro Gly Leu Thr Val Gln Leu Leu Ser Leu Leu Leu Leu
                20                  25                  30

Val Pro Val His Pro Gln Arg Leu Pro Arg Met Gln Glu Asp Ser Pro
                35                  40                  45

Leu Gly Gly Gly Ser Ser Gly Glu Asp Pro Leu Gly Glu Glu Asp
        50                  55                  60

Leu Pro Ser Glu Glu Asp Ser Pro Arg Glu Glu Asp Pro Pro Gly Glu
 65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
               100                 105                 110

Leu Pro Thr Val Glu Ala Pro Gly Asp Pro Gln Glu Pro Gln Asn Asn
            115                 120                 125

Ala His Arg Asp Lys Glu Gly Asp Asp Gln Ser His Trp Arg Tyr Gly
        130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175
```

```
Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
            195                 200                 205

Gly Leu Glu Met Ala Leu Gly Pro Gly Arg Glu Tyr Arg Ala Leu Gln
210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
            275                 280                 285

Tyr Glu Gln Leu Leu Ser Arg Leu Glu Glu Ile Ala Glu Glu Gly Ser
290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
            355                 360                 365

Ser Arg Leu Gln Leu Asn Phe Arg Ala Thr Gln Pro Leu Asn Gly Arg
370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Gly Ser
                405                 410                 415

His His His His His His His His Gly
            420                 425

<210> SEQ ID NO 34
<211> LENGTH: 8
<212> TYPE: PRT
<213> ORGANISM: Artificial Sequence
<220> FEATURE:
<223> OTHER INFORMATION: 11H9 epitope

<400> SEQUENCE: 34

Glu Glu Asp Leu Pro Gly Glu Glu
1               5

<210> SEQ ID NO 35
<211> LENGTH: 13
<212> TYPE: PRT
<213> ORGANISM: Artificial Sequence
<220> FEATURE:
<223> OTHER INFORMATION: 12H8 epitope

<400> SEQUENCE: 35

Leu Pro Arg Met Gln Glu Asp Ser Pro Leu Gly Gly Gly
1               5                   10

<210> SEQ ID NO 36
<211> LENGTH: 14
<212> TYPE: PRT
```

```
<213> ORGANISM: Artificial Sequence
<220> FEATURE:
<223> OTHER INFORMATION: Putative 2C7 epitope

<400> SEQUENCE: 36

Pro Ser Asp Phe Ser Arg Tyr Phe Gln Tyr Glu Gly Ser Leu
1               5                   10

<210> SEQ ID NO 37
<211> LENGTH: 6
<212> TYPE: PRT
<213> ORGANISM: Artificial Sequence
<220> FEATURE:
<223> OTHER INFORMATION: CA-IX repeat sequence

<400> SEQUENCE: 37

Gly Glu Glu Asp Leu Pro
1               5

<210> SEQ ID NO 38
<211> LENGTH: 15
<212> TYPE: PRT
<213> ORGANISM: Artificial Sequence
<220> FEATURE:
<223> OTHER INFORMATION: hCA-IX amino acid 37-51

<400> SEQUENCE: 38

Pro Gln Arg Leu Pro Arg Met Gln Glu Asp Ser Pro Leu Gly Gly
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: hCA-IX amino acid 47-61

<400> SEQUENCE: 39

Ser Pro Leu Gly Gly Gly Ser Ser Gly Glu Asp Asp Pro Leu Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: hCA-IX amino acid 57-71

<400> SEQUENCE: 40

Asp Asp Pro Leu Gly Glu Glu Asp Leu Pro Ser Glu Glu Asp Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: hCA-IX amino acid 67-81

<400> SEQUENCE: 41

Ser Glu Glu Asp Ser Pro Arg Glu Glu Asp Pro Pro Gly Glu Glu
1               5                   10                  15

<210> SEQ ID NO 42
<211> LENGTH: 15
<212> TYPE: PRT
<213> ORGANISM: Artificial Sequence
```

```
<220> FEATURE:
<223> OTHER INFORMATION: hCA-IX amino acid 77-91

<400> SEQUENCE: 42

Pro Pro Gly Glu Glu Asp Leu Pro Gly Glu Glu Asp Leu Pro Gly
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: hCA-IX amino acid 87-101

<400> SEQUENCE: 43

Glu Asp Leu Pro Gly Glu Glu Asp Leu Pro Glu Val Lys Pro Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: hCA-IX amino acid 97-111

<400> SEQUENCE: 44

Glu Val Lys Pro Lys Ser Glu Glu Gly Ser Leu Lys Leu Glu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: hCA-IX amino acid 107-121

<400> SEQUENCE: 45

Ser Leu Lys Leu Glu Asp Leu Pro Thr Val Glu Ala Pro Gly Asp
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: hCA-IX amino acid 117-131

<400> SEQUENCE: 46

Glu Ala Pro Gly Asp Pro Gln Glu Pro Gln Asn Asn Ala His Arg
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: hCA-IX amino acid 126-140

<400> SEQUENCE: 47

Gln Asn Asn Ala His Arg Asp Lys Glu Gly Asp Asp Gln Ser His
1               5                   10                  15

<210> SEQ ID NO 48
<211> LENGTH: 35
<212> TYPE: PRT
<213> ORGANISM: Artificial Sequence
<220> FEATURE:
```

<223> OTHER INFORMATION: hCA-IX amino acid 37-71

<400> SEQUENCE: 48

Pro Gln Arg Leu Pro Arg Met Gln Glu Asp Ser Pro Leu Gly Gly Gly
1               5                   10                  15

Ser Ser Gly Glu Asp Asp Pro Leu Gly Glu Glu Asp Leu Pro Ser Glu
            20                  25                  30

Glu Asp Ser
        35

<210> SEQ ID NO 49
<211> LENGTH: 45
<212> TYPE: PRT
<213> ORGANISM: Artificial Sequence
<220> FEATURE:
<223> OTHER INFORMATION: hCA-IX amino acid 67-111

<400> SEQUENCE: 49

Ser Glu Glu Asp Ser Pro Arg Glu Glu Asp Pro Pro Gly Glu Glu Asp
1               5                   10                  15

Leu Pro Gly Glu Glu Asp Leu Pro Gly Glu Glu Asp Leu Pro Glu Val
            20                  25                  30

Lys Pro Lys Ser Glu Glu Glu Gly Ser Leu Lys Leu Glu
        35                  40                  45

<210> SEQ ID NO 50
<211> LENGTH: 34
<212> TYPE: PRT
<213> ORGANISM: Artificial Sequence
<220> FEATURE:
<223> OTHER INFORMATION: hCA-IX amino acid 107-140

<400> SEQUENCE: 50

Ser Leu Lys Leu Glu Asp Leu Pro Thr Val Glu Ala Pro Gly Asp Pro
1               5                   10                  15

Gln Glu Pro Gln Asn Asn Ala His Arg Asp Lys Glu Gly Asp Asp Gln
            20                  25                  30

Ser His

<210> SEQ ID NO 51
<211> LENGTH: 104
<212> TYPE: PRT
<213> ORGANISM: Artificial Sequence
<220> FEATURE:
<223> OTHER INFORMATION: hCA-IX amino acid 37-140

<400> SEQUENCE: 51

Pro Gln Arg Leu Pro Arg Met Gln Glu Asp Ser Pro Leu Gly Gly Gly
1               5                   10                  15

Ser Ser Gly Glu Asp Asp Pro Leu Gly Glu Glu Asp Leu Pro Ser Glu
            20                  25                  30

Glu Asp Ser Pro Arg Glu Glu Asp Pro Pro Gly Glu Glu Asp Leu Pro
        35                  40                  45

Gly Glu Glu Asp Leu Pro Gly Glu Glu Asp Leu Pro Glu Val Lys Pro
    50                  55                  60

Lys Ser Glu Glu Glu Gly Ser Leu Lys Leu Glu Asp Leu Pro Thr Val
65                  70                  75                  80

Glu Ala Pro Gly Asp Pro Gln Glu Pro Gln Asn Asn Ala His Arg Asp
                85                  90                  95

Lys Glu Gly Asp Asp Gln Ser His

```
                       100

<210> SEQ ID NO 52
<211> LENGTH: 9
<212> TYPE: PRT
<213> ORGANISM: Artificial Sequence
<220> FEATURE:
<223> OTHER INFORMATION: 12H8 minimal epitope

<400> SEQUENCE: 52

Leu Pro Arg Met Gln Glu Asp Ser Pro
1               5

<210> SEQ ID NO 53
<211> LENGTH: 8
<212> TYPE: PRT
<213> ORGANISM: Artificial Sequence
<220> FEATURE:
<223> OTHER INFORMATION: 11H9 minimal epitope

<400> SEQUENCE: 53

Glu Asp Leu Pro Gly Glu Glu Asp
1               5
```